(12) United States Patent
Traynor et al.

(10) Patent No.: US 11,724,134 B2
(45) Date of Patent: *Aug. 15, 2023

(54) COMPOSITIONS CONTAINING A CELLULOSE DERIVED CAPSULE WITH A SUNSCREEN ACTIVE AGENT

(71) Applicant: CoLabs International Corporation, Las Vegas, NV (US)

(72) Inventors: Daniel H. Traynor, Sarasota, FL (US); Laura E. Cohen, Huntington Beach, CA (US)

(73) Assignee: CoLabs International Corporation, Las Vegas, NV (US)

( * ) Notice: Subject to any disclaimer, the term of this patent is extended or adjusted under 35 U.S.C. 154(b) by 46 days.

This patent is subject to a terminal disclaimer.

(21) Appl. No.: 16/435,347

(22) Filed: Jun. 7, 2019

(65) Prior Publication Data

US 2019/0290940 A1 Sep. 26, 2019

Related U.S. Application Data

(63) Continuation-in-part of application No. 15/430,416, filed on Feb. 10, 2017, now Pat. No. 10,322,301, which is a continuation-in-part of application No. 14/702,615, filed on May 1, 2015, now Pat. No. 9,592,184, which is a continuation of application No. 14/072,926, filed on Nov. 6, 2013, now Pat. No. 9,456,966.

(60) Provisional application No. 62/293,703, filed on Feb. 10, 2016, provisional application No. 61/769,758, filed on Feb. 27, 2013, provisional application No. 61/722,870, filed on Nov. 6, 2012.

(51) Int. Cl.

| | | |
|---|---|---|
| A61K 6/60 | (2020.01) |
| A61Q 17/04 | (2006.01) |
| A61K 8/06 | (2006.01) |
| A61Q 5/02 | (2006.01) |
| A61Q 19/10 | (2006.01) |
| A61Q 19/00 | (2006.01) |
| A61Q 5/06 | (2006.01) |
| A61K 8/35 | (2006.01) |
| A61K 8/73 | (2006.01) |
| C09B 67/02 | (2006.01) |
| A61K 8/11 | (2006.01) |
| A61K 8/37 | (2006.01) |
| A61K 8/19 | (2006.01) |
| A61K 8/44 | (2006.01) |
| A61K 8/46 | (2006.01) |
| A61K 8/49 | (2006.01) |
| A61Q 17/02 | (2006.01) |
| C09B 69/10 | (2006.01) |
| A61Q 5/12 | (2006.01) |
| A61Q 17/00 | (2006.01) |

(52) U.S. Cl.
CPC .............. *A61Q 17/04* (2013.01); *A61K 8/062* (2013.01); *A61K 8/11* (2013.01); *A61K 8/19* (2013.01); *A61K 8/35* (2013.01); *A61K 8/37* (2013.01); *A61K 8/445* (2013.01); *A61K 8/466* (2013.01); *A61K 8/494* (2013.01); *A61K 8/498* (2013.01); *A61K 8/4926* (2013.01); *A61K 8/731* (2013.01); *A61Q 5/02* (2013.01); *A61Q 5/06* (2013.01); *A61Q 5/12* (2013.01); *A61Q 17/02* (2013.01); *A61Q 19/007* (2013.01); *A61Q 19/10* (2013.01); *C09B 67/0097* (2013.01); *C09B 69/109* (2013.01); *A61K 2800/21* (2013.01); *A61K 2800/412* (2013.01); *A61K 2800/60* (2013.01); *A61Q 17/005* (2013.01)

(58) Field of Classification Search
None
See application file for complete search history.

(56) References Cited

U.S. PATENT DOCUMENTS

| | | |
|---|---|---|
| 1,478,208 A | 12/1923 | Duddleson et al. |
| 3,462,479 A | 8/1969 | Strobel et al. |
| 3,691,270 A | 9/1972 | Charle et al. |
| 4,402,977 A | 9/1983 | Grollier et al. |
| 4,540,507 A | 9/1985 | Grollier |
| 4,542,125 A | 9/1985 | Gorman et al. |
| 4,663,155 A | 5/1987 | Murray et al. |
| 4,663,156 A | 5/1987 | Clum et al. |

(Continued)

FOREIGN PATENT DOCUMENTS

| | | |
|---|---|---|
| CN | 1341012 A | 3/2002 |
| EP | 0025379 B1 | 6/1984 |

(Continued)

OTHER PUBLICATIONS

Boissiere, et al. Turning Biopolymer Particles into Hybrid Capsules: the Example of Silica/Alginate Nanocomposites, J. Mater. Chem. 16: 1178-1182 (2006).

(Continued)

*Primary Examiner* — Susan T Tran
(74) *Attorney, Agent, or Firm* — UltimatEdge IP Law Group, P.C.; Dean G. Stathakis

(57) ABSTRACT

A sunscreen composition comprised of one or more sunscreen active agents encapsulated in a cellulose derived capsule wherein the composition can contain one or more additional agents. A sunscreen composition can be mixed with a body wash, an after shower body lotion, a shampoo, a conditioner, a soap, a gel, a hand sanitizer, a cream, a spray, a mouse, a lotion, an ointment, a make-up product, a lip balm, a hair spray product, an arachnid/insect repellent or a medicinal product.

19 Claims, 3 Drawing Sheets

(56) References Cited

U.S. PATENT DOCUMENTS

| | | |
|---|---|---|
| 4,683,134 A | 7/1987 | Palinczar |
| 4,686,099 A | 8/1987 | Palinczar |
| 4,699,779 A | 10/1987 | Palinczar |
| 4,701,321 A | 10/1987 | Bernstein |
| 4,749,501 A | 6/1988 | Nakagawa et al. |
| 4,803,195 A | 2/1989 | Holzner |
| 4,874,538 A | 10/1989 | Dawson et al. |
| 4,904,524 A | 2/1990 | Yoh |
| 4,933,174 A | 6/1990 | Bernstein |
| 4,985,170 A | 1/1991 | Dawson et al. |
| 5,071,706 A | 12/1991 | Soper et al. |
| 5,089,269 A | 2/1992 | Noda et al. |
| 5,132,117 A | 7/1992 | Speaker et al. |
| 5,169,624 A | 12/1992 | Ziegler et al. |
| 5,292,801 A | 3/1994 | Avnir et al. |
| 5,300,564 A | 4/1994 | Avnir et al. |
| 5,306,485 A | 4/1994 | Robinson et al. |
| 5,455,048 A | 10/1995 | Lahmani et al. |
| 5,476,660 A | 12/1995 | Somasundaran et al. |
| 5,508,259 A | 4/1996 | Holzner et al. |
| 5,543,136 A | 8/1996 | Aldous |
| 5,589,177 A | 12/1996 | Herb et al. |
| 5,614,217 A | 3/1997 | Chiprich et al. |
| 5,599,555 A | 4/1997 | El-Nokaly |
| 5,620,692 A | 4/1997 | Potter et al. |
| 5,643,341 A | 7/1997 | Hirsch et al. |
| 5,661,189 A | 8/1997 | Grieveson et al. |
| 5,674,912 A | 10/1997 | Martin |
| 5,683,716 A | 11/1997 | Hata et al. |
| 5,716,920 A | 2/1998 | Glenn et al. |
| 5,733,531 A | 3/1998 | Mitchnick et al. |
| 5,759,524 A | 6/1998 | Tanner et al. |
| 5,770,556 A | 6/1998 | Farrell et al. |
| 5,783,174 A * | 7/1998 | Deckner .................. A61K 8/19 424/400 |
| 5,785,979 A | 7/1998 | Wells |
| 5,849,273 A | 12/1998 | Bonda et al. |
| 5,876,755 A | 2/1999 | Perring et al. |
| 5,900,394 A | 5/1999 | Goel et al. |
| 5,904,917 A | 5/1999 | Mattai et al. |
| 5,914,101 A | 6/1999 | Tapley et al. |
| 5,948,416 A | 9/1999 | Wagner et al. |
| 5,955,409 A | 9/1999 | Farrell et al. |
| 5,989,529 A | 11/1999 | Kaplan |
| 5,989,536 A | 11/1999 | Deckner et al. |
| 6,024,942 A | 2/2000 | Tanner et al. |
| 6,043,204 A | 3/2000 | Kaufman et al. |
| 6,057,275 A | 5/2000 | Fair et al. |
| 6,074,630 A | 6/2000 | Devillez et al. |
| 6,096,697 A | 8/2000 | Wells |
| 6,110,888 A | 8/2000 | Lupo, Jr. et al. |
| 6,159,453 A | 12/2000 | Avnir et al. |
| 6,217,852 B1 | 4/2001 | Gildengerg et al. |
| 6,224,852 B1 | 5/2001 | Morgan et al. |
| 6,238,650 B1 | 5/2001 | Lapidot et al. |
| 6,248,364 B1 | 6/2001 | Sengupta et al. |
| 6,248,703 B1 | 6/2001 | Finucane et al. |
| 6,255,264 B1 | 7/2001 | Fleurot et al. |
| 6,303,149 B1 | 10/2001 | Magdassi et al. |
| 6,348,218 B1 | 2/2002 | Hed et al. |
| 6,362,146 B1 | 3/2002 | Macaulay |
| 6,391,287 B1 | 5/2002 | Baldo et al. |
| 6,395,269 B1 | 5/2002 | Fuller et al. |
| 6,399,045 B1 | 6/2002 | Morgan et al. |
| 6,412,658 B1 | 7/2002 | Bartholomew et al. |
| 6,436,375 B1 | 8/2002 | Lapidot et al. |
| 6,468,509 B2 | 10/2002 | Lapidot et al. |
| 6,471,975 B1 | 10/2002 | Banovetz et al. |
| 6,485,713 B1 | 11/2002 | Bonda et al. |
| 6,491,902 B2 | 12/2002 | Shefer et al. |
| 6,500,791 B2 | 12/2002 | Pereira et al. |
| 6,524,594 B1 | 2/2003 | Santora et al. |
| 6,555,095 B1 | 4/2003 | Garrison |
| 6,576,228 B1 | 6/2003 | Crookham et al. |
| 6,607,713 B1 | 8/2003 | Chodorowski et al. |
| 6,696,067 B2 | 2/2004 | Brandt et al. |
| 6,699,824 B1 | 3/2004 | Dawson et al. |
| 6,740,631 B2 | 5/2004 | Shefer et al. |
| 6,770,270 B2 | 8/2004 | Bonda |
| 6,825,161 B2 | 11/2004 | Shefer et al. |
| 6,855,335 B2 | 2/2005 | Seok et al. |
| 6,913,825 B2 | 7/2005 | Ostafin et al. |
| 6,998,113 B1 | 2/2006 | Traynor et al. |
| 7,001,592 B1 | 2/2006 | Traynor et al. |
| 7,025,952 B1 | 4/2006 | Traynor et al. |
| 7,037,513 B1 | 5/2006 | Traynor et al. |
| 7,053,034 B2 | 5/2006 | Shefer et al. |
| 7,074,747 B1 | 7/2006 | Lukenbach et al. |
| 7,098,032 B2 | 8/2006 | Trubetskoy et al. |
| 7,138,382 B2 | 11/2006 | Wolff et al. |
| 7,226,582 B2 | 6/2007 | Traynor et al. |
| 7,226,607 B2 | 6/2007 | Uchiyama et al. |
| 8,039,015 B2 | 10/2011 | Speaker |
| 2002/0028235 A1 | 3/2002 | Reed et al. |
| 2002/0034487 A1 | 3/2002 | Maubru et al. |
| 2002/0064541 A1 | 5/2002 | Lapidot et al. |
| 2002/0077256 A1 | 6/2002 | Niemiec et al. |
| 2002/0131939 A1 | 9/2002 | Djerassi et al. |
| 2002/0167404 A1 | 11/2002 | Jordan |
| 2003/0032593 A1 | 2/2003 | Wender et al. |
| 2003/0059382 A1 | 3/2003 | Brandt et al. |
| 2003/0059383 A1 | 3/2003 | SaNogueira et al. |
| 2003/0108580 A1 | 6/2003 | Hasenzahl et al. |
| 2003/0134761 A1 | 7/2003 | Sebillotte-Arnaud et al. |
| 2003/0147818 A1 | 8/2003 | Dubief et al. |
| 2003/0171230 A1 | 9/2003 | Shana'a et al. |
| 2003/0176303 A1 | 9/2003 | Niemiec et al. |
| 2003/0187665 A1 | 10/2003 | Boyd |
| 2004/0005278 A1 | 1/2004 | Reinhart et al. |
| 2004/0028709 A1 | 2/2004 | Dueva et al. |
| 2004/0047826 A1 | 3/2004 | Brown |
| 2004/0101498 A1 | 5/2004 | Koshti et al. |
| 2004/0120905 A1 | 6/2004 | Gall et al. |
| 2004/0167046 A1 | 8/2004 | Lukenbach et al. |
| 2004/0169298 A1 | 9/2004 | Fukasawa et al. |
| 2004/0234558 A1 | 11/2004 | O'Conner et al. |
| 2004/0247536 A1 | 12/2004 | Chaudhuri |
| 2004/0247543 A1 | 12/2004 | Huerta et al. |
| 2005/0065047 A1 | 3/2005 | Shefer et al. |
| 2005/0123611 A1 | 6/2005 | Barbe et al. |
| 2005/0255055 A1 | 11/2005 | Wagner et al. |
| 2006/0018966 A1 | 1/2006 | Lin et al. |
| 2006/0073106 A1 | 4/2006 | Berg-Schultz et al. |
| 2006/0135645 A1 | 6/2006 | Glassel et al. |
| 2007/0028400 A1 | 2/2007 | Wolber et al. |
| 2007/0292676 A1 | 12/2007 | Naigertsik et al. |
| 2008/0112904 A1 | 5/2008 | Traynor et al. |
| 2008/0317795 A1 | 12/2008 | Traynor et al. |
| 2009/0280149 A1 | 11/2009 | Tajima et al. |
| 2009/0324655 A1 | 12/2009 | Polonka et al. |
| 2010/0015188 A1 | 1/2010 | Izu et al. |
| 2010/0092410 A1 | 4/2010 | Cockerell et al. |
| 2010/0135936 A1 | 6/2010 | Dueva-Koganov et al. |
| 2011/0020253 A1 | 1/2011 | Doyle et al. |
| 2011/0150795 A1 | 6/2011 | Loing et al. |
| 2011/0206793 A1 | 8/2011 | Hines et al. |
| 2012/0141395 A1 | 6/2012 | Chaudhuri et al. |
| 2012/0148644 A1 | 6/2012 | Popplewell et al. |
| 2012/0207804 A1 | 8/2012 | Traynor et al. |
| 2013/0089507 A1 * | 4/2013 | Milora .................. A61K 8/87 424/59 |
| 2014/0127275 A1 | 5/2014 | Cohen |
| 2014/0242131 A1 | 8/2014 | Cohen |
| 2014/0242132 A1 | 8/2014 | Cohen |
| 2014/0255456 A1 | 9/2014 | Cohen |
| 2015/0231046 A1 | 8/2015 | Cohen |
| 2017/0000697 A1 | 1/2017 | Cohen |
| 2017/0000698 A1 | 1/2017 | Cohen |
| 2017/0157021 A1 | 6/2017 | Traynor et al. |
| 2017/0216164 A1 | 8/2017 | Traynor et al. |
| 2017/0216165 A1 | 8/2017 | Traynor et al. |
| 2018/0042828 A1 | 2/2018 | Cohen |

(56) References Cited

U.S. PATENT DOCUMENTS

| | | |
|---|---|---|
| 2018/0042829 A1 | 2/2018 | Cohen |
| 2018/0055748 A1 | 3/2018 | Cohen |
| 2018/0125980 A1 | 5/2018 | Finley et al. |

FOREIGN PATENT DOCUMENTS

| | | |
|---|---|---|
| EP | 0254447 B1 | 3/1993 |
| EP | 0399911 B1 | 7/1993 |
| EP | 1162942 B1 | 6/2004 |
| WO | 1992016195 A1 | 10/1992 |
| WO | 199845036 A1 | 10/1998 |
| WO | 199943296 A2 | 11/1999 |
| WO | 200042985 A1 | 7/2000 |
| WO | 200057850 A1 | 10/2000 |
| WO | 2005009602 A2 | 2/2005 |
| WO | 2008144734 A1 | 11/2008 |
| WO | 2010000587 A2 | 1/2010 |
| WO | 2012074250 A2 | 6/2012 |
| WO | 2013087548 A2 | 6/2013 |
| WO | 2013107354 A1 | 7/2013 |
| WO | 2014074555 A1 | 5/2014 |
| WO | 2014132261 A2 | 9/2014 |
| WO | 2017139701 A1 | 8/2017 |

OTHER PUBLICATIONS

Business Wire, Leading Cosmetics Industry Chemist Joins Skin Innovator; Performance Brands Names Michael Dulak to Board of Directors (1999) Best Availabe Copy.

Copyrightkids.org, http://web.archive.org/web/20030919013921/http://www.copyrightkids.org/definitions.html, Retrieved via WayBack Machine with archive date of Sep. 19, 2003.

Datachem Software Developers of CertiStep, License Agreements, http://web.archive.org/web/20031109074418/http://www.datachemsoftware.com/licenses.htm, retrieved via Wayback Machine with archive date of Nov. 9, 2003.

Donahue, Intellectual Property Licensing: A Crib Sheet for Deal Makers, http://teklaw.com/iplicens.htm (1998).

Donaldson, et al., Ultrafine Particles, Occup. Environ. Med., 58(3): 211-216 (2001).

Earth Supplied Products, LLC, Esp Kerabead™ Avo/Octo Encap Product Specification.

Earth Supplied Products, LLC, Esp Kerabead™ Shea Oil-20 Product Specification.

Earth Supplied Products, LLC, Esp Kerabead™ Silicone-20 Product Specification.

Earth Supplied Products, LLC, Esp Vegabead™ OMC 40 Product Specification.

EMD Chemicals Inc., Eusolex® UV-Pearls™ Product Information.
EPO, Supplemental Search Report, dated Apr. 15, 2016.

Ford, Sunscreen How Products Are Made, Find Articles at BNET, vol. 2, (1994), Retrieved from http://www.findarticles.com.

Ghosh, Functional Coatings and Microencapsulation: A General Perspective, In Functional Coatings, pp. 1-28 (Wiley-VCH Verlag GmbH & Co KgaA, Weinheim) 2006.

Karr, et al., A Novel Encapsulation of N,N-diethyl-3-methylbenzamide (DEET) Facorably Modifies Skin Absorption while Maintaining Effective Evaporation Rates, J. Controlled Release 160:502-508 (2012).

Klykken, et al., Silicone Film-Forming Technologies for Health Care Applications, Dow Corning [online] (2009).

Merck KGaA, Eusolex® T-AVO, website description page (2005).

Merck KGaA, Eusolex® UV-Pearls™, website description page (2005).

Parsol® 1789 Product Page.

PCT Form ISA 210, International Search Report, PCT/US2006/003365, dated May 24, 2006.

PCT Form ISA 237, Written Opinion, PCT/US2006/003365, dated May 24, 2006.

PCT Form ISA 210, International Search Report, PCT/US2013/068651, dated Mar. 5, 2014.

PCT Form ISA 237, Written Opinion, PCT/US2013/068651, dated Mar. 5, 2014.

PCT Form IB 373, International Preliminary Report on Patentability, PCT/US2013/068651, dated May 12, 2015.

PCT Form ISA 210, International Search Report, PCT/US2017/017556, dated Feb. 10, 2017.

PCT Form ISA 237, Written Opinion, PCT/US2017/017556, dated Feb. 10, 2017.

PCT Form ISA 210, International Search Report, PCT/US2018/017720, dated May 14, 2018.

PCT Form ISA 210, International Search Report, PCT/US2018/017722, dated Jun. 5, 2018.

PCT Form ISA 237, Written Opinion, PCT/US2018/017720, dated May 14, 2018.

PCT Form ISA 237, Written Opinion, PCT/US2018/017722, dated Jun. 5, 2018.

Sanar, website (2016).

Specos, et al., Microencapsulated Citronella Oil for Mosquito Repellent Finishing of Cotton Textiles, Trans. R. Soc. Trop. Med. Hyg. 104: 653-658 (2010).

UCLA Trademarks and Licensing, http://web.archive.org/web/20030811091818/http://www.asucla.ucla.edu/licensing/index.asp, Retrieved via Wayback Machine with archive date of Aug. 11, 2003.

Xiong, et al., Complex Coacervation of Ovalbumin-Carboxymethylcellulose Assessed by Isothermal Titration Calorimeter and Rheology: Effect of Ionic Strength and Charge Density of Polysaccharides, Food Hydrocolloids 73:41-50 (2017).

Yeh, et al. Synthesis of Hollow Silica Spheres with Mesostructed Shell Using Cationic-Anionic-Neutral Block Copolymer Ternary Surfactants, Langmuier22(1): 6-9 (2006).

Mcpartland, Cannabis as Repellent and Pesticide, pp. 17 (1997).

* cited by examiner

FIG. 3A
FIG. 3B
FIG. 3C
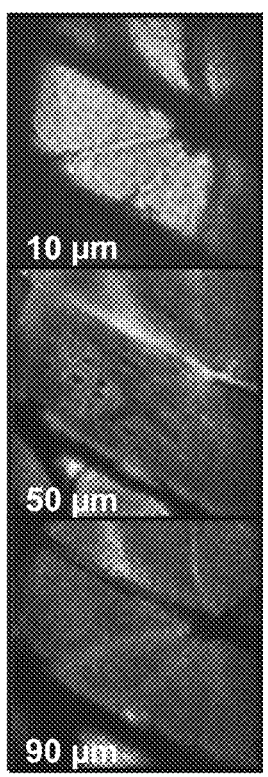
FIG. 3D
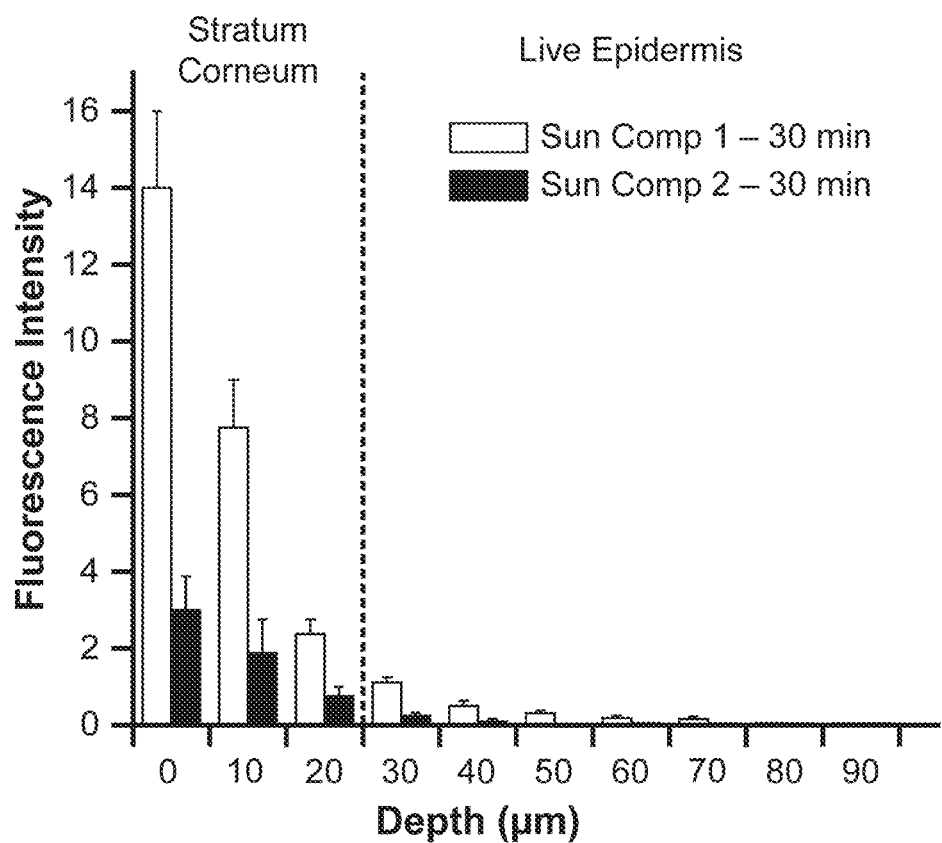

COMPOSITIONS CONTAINING A CELLULOSE DERIVED CAPSULE WITH A SUNSCREEN ACTIVE AGENT

This continuation claims the benefit of priority and the filing date pursuant to 35 U.S.C. § 120 to U.S. Non-Provisional Ser. No. 15/430,416, filed Feb. 10, 2017, a continuation-in-part application that claims priority to U.S. Non-Provisional Ser. No. 14/702,615, filed May 1, 2015, now U.S. Pat. No. 9,592,184, a continuation application that claims priority to U.S. Non-Provisional Ser. No. 14/072,926, filed Nov. 6, 2013, now U.S. Pat. No. 9,456,966, which claims priority pursuant to 35 U.S.C. § 119(e) to U.S. Provisional Patent Application 61/769,758, filed Feb. 27, 2013 and U.S. Provisional Patent Application 61/722,870, filed Nov. 6, 2012; and U.S. Non-Provisional Ser. No. 15/430,416, filed Feb. 10, 2017, claims the benefit of priority and the filing date pursuant to 35 U.S.C. § 119(e) to U.S. Provisional Patent Application 62/293,703, filed Feb. 10, 2016, each of which is hereby incorporated by reference in its entirety.

BACKGROUND

Overexposure to ultraviolet ("UV") radiation produced by the sun can result in deleterious effects to individuals, including, sunburn, premature aging of skin, premature wrinkling, and for many individuals, an increase in the risk of skin cancer. To avoid these adverse effects, it is common for individuals prior to exposure to sunlight to apply a sunscreen product to their skin. Such products are widely available and relatively inexpensive. However, many individuals fail to use them on a regular basis for reasons that include, without limitation, convenience of use and the feel of the product after application. Additionally, these products suffer from other issues such as uneven application and their inability to provide adequate protection due to loss of coverage suffered from such activities as swimming, exercise that results in perspiration and dermal penetration and subsequent excretion through the urine of the active agents incorporated in the sunscreen product that protects an individual from the sun's harmful UV radiation.

To provide more convenient, consistent and even sunscreen protection, several products that are used by individuals on a regular basis have been developed that incorporate sunscreen active agents that protect an individual from the sun's harmful UV radiation. In the United States, it is common for individuals to bathe or shower on a regular basis, in most instances, every day. It is also common for those same individuals to use a body wash, shampoo, conditioner, lotion or cream while they shower. Therefore, products have been developed that include sunscreen active agents in bodywashes and shampoos. Other products that have been developed to include sunscreen active agents are make-up, lip balm and even hair spray products. Though the use of these products adds convenience, they generally have not overcome some of the other issues related to the use of sunscreen products.

Nevertheless, in spite of all the above attempts, there remains an unmet need for an effective sunscreen product that provides an effective level of sun protection, particularly a level of sun block or sunscreen that is higher than existing formulations and remains effective even after rinsing one or more times following application as well as having a gentle or acceptable feel on the human skin, as opposed to an oily feel. The present invention addresses one or more of these needs by utilizing encapsulation technologies, milder surfactant systems, and good adhesive polymers that provide a strong binding capability, making it more efficient for deposition of sunscreen. The present invention adds cellulose derived capsules that contain one or more sunscreen active agents, resulting in an increase in SPF in the formulation as compared to free sunscreen or non-encapsulated material. The cellulose derived capsules of the present invention also lay down on the skin surface in a manner that result in packing and spreading of the sunscreen active agent over the skin of an individual. The cellulose derived capsules of the present invention also provide a means for formulating a sunscreen active agent that can result in a greater amount of sunscreen active agent after application through such products as shampoo, body wash, conditioner, lotion, mousse, spray, hand sanitizer, cream and gel.

SUMMARY

Aspects of the present specification disclose compositions sunscreen composition comprising one or more flexible cellulose-derived encapsulates comprising one or more sunscreen active agents and one or more photostabilizing agents. The disclosed compositions can further comprise one or more flexible cellulose-derived encapsulates comprising one or more oils, one or more emollients, one or more thickening agents, one or more film formers, one or more polyquaterniums, one or more surfactants, one or more flexible cellulose-derived encapsulates comprising one or more arachnid/insect repellents, one or more polymers, one or more fragrances, one or more plant oils, and/or one or more additional agents.

Other aspects of the present specification disclose methods of preventing exposure to UV radiation. The UV radiation may be a naturally-occurring UV radiation or a man-made UV radiation.

BRIEF DESCRIPTION OF THE FIGURES

FIG. 3A shows a fluorescent image of dye penetration into human skin at 10 µm from the skin surface; FIG. 3B shows a fluorescent image of dye penetration into human skin at 50 µm from the skin surface; FIG. 3C shows a fluorescent image of dye penetration into human skin at 90 µm from the skin surface; FIG. 3D shows a bar graph of dye penetration into human skin using fluorescence intensity of dye versus penetration depth of dye.

DETAILED DESCRIPTION

Figure 1:
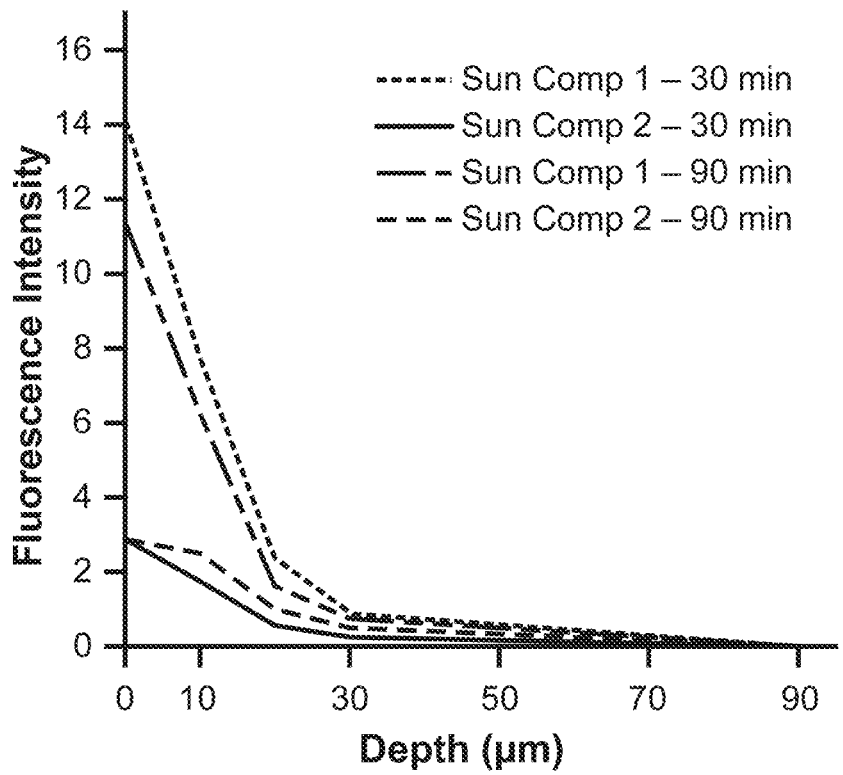
FIG. 1 shows a graph of dye penetration into human skin using fluorescence intensity of dye verus penetration depth of dye. Measurements were taken 30 minutes and 90 minutes after application of a composition.

The present specification encompasses compositions comprising one or more sunscreen active agents enclosed in a cellulose derived capsule (also referred to as "an encapsulated sunscreen agent"). The sunscreen compositions are formulated with cationic polymer in a manner that causes the encapsulated sunscreen agent to adhere or be trapped in a polymer complex to a skin surface, hair shaft, or any substrate which can accept an opposing charge forming a protective layer that shields an individual from the deleterious effects of harmful UV radiation due to sun exposure. The adhesive nature of the encapsulated sunscreen agent and its film forming embodiment enables the sunscreen composition to remain on the skin's surface for longer periods of time relative to conventional sunscreen compositions without the encapsulates and its packing capability, even after exposure to water or other liquids, thereby extending its protective time-frame. In addition, because the sunscreen active agent remained encapsulated, protection is not lost due to absorption of the sunscreen agent into the skin. Therefore, the disclosed sunscreen compositions provide significantly longer sunscreen protection relative to conventional sunscreen compositions. A sunscreen composition disclosed herein can be manufactured as a solid, a liquid, a colloidal, or an aerosol. In addition, a sunscreen composition disclosed herein can be manufactured into, without limitation, a body wash, an after shower body lotion, a shampoo, a conditioner, a soap, a gel, a hand sanitizer, a cream, a spray, a mouse, a lotion, an ointment, a make-up product, a lip balm, a hair spray product, an arachnid/insect repellent or a medicinal product. As such, the disclosed compositions may be easily and conveniently applied during normal hygienic activities, such as, e.g., washing, showering, bathing, after bathing or showering while the skin is still wet, or during routine moisturizing or other hygiene activities, resulting in the application of an effective level of an encapsulated sunscreen agent to a skin surface that will provide excellent solar protection of an individual's body even after activities that would remove conventional sunscreen protections, such as, e.g., washing, rinsing, or swimming.

Aspects of the present specification, disclose a sunscreen active agent. A sunscreen active agent is an ultraviolet (UV) ray-blocking compound that absorbs, blocks and/or reflects UV radiation. A sunscreen active agent disclosed herein absorbs, blocks and/or reflects UV radiation given off by a natural source, such as, e.g., sunlight, and/or man-made source, such as, e.g., a fluorescent light bulb. In an aspect of this embodiment, a sunscreen active agent exhibits absorptive and/or reflective properties within the wavelength region of between about 290 to about 420 nm. Any sunscreen active agent known in the art or apparent to a skilled artisan may be used. A sunscreen active agent disclosed herein may be an organic molecule or inorganic molecule. In addition, a sunscreen active agent may be a UVA absorber, a UVA blocker, a UVA reflector, a UVB absorber, a UVB blocker, a UVB reflector, a broad spectrum UVA and UVB absorber, a broad spectrum UVA and UVB blocker, a broad spectrum UVA and UVB reflector, a physical blocker, a physical reflector, or any combination thereof. A UVA absorber can be a UVA I absorber and/or UVA II absorber.

Sunscreen active agents commonly contain one or more of the following ingredients: 1) a chemical sunscreen active agent, typically an organic compound that absorb UV light; 2) a physical sunscreen active agent, typically an inorganic particulates that reflect, scatter, and absorb UV light; and 3) a hybrid sunscreen active agent, typically an organic particulate that absorbs UV light like an organic chemical compound, but also contain multiple chromophores that may reflect and scatter UV light like an inorganic particulate.

Organic sunscreen active agents can be grouped based upon their chemical structure. Such groups include, without limitation: 1) a para-amino benzoate or derivative or salt thereof; 2) a salicylate or derivative or salt thereof; 3) a cinnamate or derivative or salt thereof; 4) a benzophenone or derivative or salt thereof; 5) an anthralinate or derivative or salt thereof; 6) dibenzoylmethane or derivative or salt thereof; 7) a camphor or derivative or salt thereof; 8) a naphtholsulfonate or derivative or salt thereof; 9) a coumarin or derivative or salt thereof; 10) a diazole or derivative or salt thereof; 11) a biphenyldisulfonate or derivative or salt thereof; 12) a hydrocarbon or derivative or salt thereof; 13) a quinolone or derivative or salt thereof; 14) a quinine salt; 15) a miscellaneous organic sunscreen active agent.

A para-amino benzoate derivative includes, without limitation, ethylbenzoic acid, isobutylbenzoic acid, benzoic acid glyceryl ester, p-dimethylaminobenzoic acid or a salt thereof.

A salicylate derivative includes, without limitation, amyl salicylate, phenyl salicylate, benzyl salicylate, menthy salicylate, octyl salicylate (2-ethylhexyl salicylate, glyceryl salicylate, a salicylate dipropylene glycol ester or a salt thereof.

A cinnamate derivative includes, without limitation, cinnamic acid derivative, such as, e.g., methyl cinnamic ester and benzyl cinnamic ester, alpha-phenyl or cinnamonitrile; a butyl cinnamoyl pyruvate; a dihydroxycinnamic acid derivatives, such as, e.g., umbelliferone, methylumbelliferone, or methylaceto-umbelliferone; a trihydroxycinnamic acid derivative, such as, e.g., esculetin, methylesculetin, daphnetin, a glucoside, such as, e.g., esculin and daphnin; octyl methoxycinnamate (Octinoxate); and a p-methoxycinnamic acid ester, such as, e.g., amyl p-methoxycinnamate, 2-ethylhexyl p-methoxycinnamate, 2-ethoxyethyl p-methoxycinnamate, diethanolamine p-methoxycinnamate, n-octyl p-methoxycinnamate (ethyl hexyl methoxycinnamate PARSOL MCX), isoamyl p-methoxycinnamate and propyl p-methoxycinnamate or a salt thereof.

A benzophenone derivative includes, without limitation, a hydroxyl-substituted benzophenone, a methoxy-substituted benzophenone, Oxybenzene (also called benzophenone-3 or 2-Hydroxy4-Methoxybenzophenone), Sulisobenzone (also called benzophenone-4), Dioxybenzone, Benzoresorcinol, 2,2',4,4'-Tetrahydroxybenzophenone, 2,2'-Dihydroxy4,4'-dimethoxpenzophenone, Octabenzone, 4-Isopropyhldibenzoylmethane or a salt thereof.

An anthranilate derivative includes, without limitation, o-aminobenzoate; methyl anthranilate, menthyl anthranilate, phenyl anthranilate, benzyl anthranilate, phenylethyl anthranilate, linalyl anthranilate, terpinyl anthranilate, ethyl-[bis (hydroxypropyl)]aminobenzoate, glyceryl aminobenzoate, a cyclohexenyl anthranilate ester or a salt thereof.

A dibenzoylmethane derivative includes, without limitation, Avobenzone (also called butylmethoxydibenzoylmethane, 4-tert-Butyl-4'-methoxydibenzoylmethane or PARSOL 1789), 4-isopropyl-dibenzoylmethane or a salt thereof.

A camphor derivative includes, without limitation, camphor benzalkonium methosulfate, terephthalidene dicamphor sulfonic acid, benzylidene camphor sulfonic acid, polyacrylamidomethyl benzylidene camphor, 4-methylbenzylidene camphor, 3-benzylidene camphor, terephthalylidene dicamphor sulfonic acid or a salt thereof.

A naphtholsulfonate derivative includes, without limitation, 2-naphthol-3,3-disulfonic, 2-naphthol-6,8-disulfonic acid or a salt thereof. A coumarin derivative includes, without limitation, 7-hydroxy coumarin, 7-methyl coumarin, 3-phenlyll coumarin or a salt thereof. A diazole derivative includes, without limitation, 2-acetyl-3-bromoindazole, phenyl benzoxazole, methyl naphthoxalole, an aryl benzothiazole or a salt thereof.

A biphenyldisulfonate derivative includes, without limitation, o-hydroxybiphenyldisulfonate, p-hydroxybiphenyldisulfonate or a salt thereof. A hydrocarbon derivative includes, without limitation, diphenylbutadiene, stilbene or a salt thereof. A quinoline derivative includes, without limitation, 8-hydroxyquinoline salts, 2-phenylquinoline or a salt thereof. A quinine salt includes, without limitation, bisulfate, sulfate, chloride, oleate, and tannate.

A miscellaneous organic sunscreen active agent includes, without limitation, octocrylene (2-ethylhexyl 2-cyano-3,3-diphenylacrylate), digalloyl trioleate, etocrylene, dibenzylideneacetone (or dibenzalacetone), dihydroxyacetone, benzalacetophenone, dihydroxynaphthoic acid, disodium phenyl dibenzimidazole tetrasulfon, butyl carbityl (6-propyl piperonyl) ether, hydroquinone, a hexaethylether, tannic acid, uric acid and vilouric acid.

Many organic and inorganic compounds can contain organic and inorganic molecules which exhibit absorption, refractive or both properties as a property of the said above and as an example can be synthesized on a surfactant, to exhibit UV absorption characteristics and furthermore be classified without being a UV absorber recognized in the current monograph.

An inorganic sunscreen active agent includes, without limitation, a metal oxide, a metal alkoxide and a polymer. Non-limiting examples of a metal oxide include an iron oxide, a titanium dioxide and a zinc oxide (e.g., Z-COTE™ HP 1, SkinCeuticals). A polymer includes, without limitation, a polyethylene polymer, a polyamide polymer and a silicone polymer. A silicone polymer includes long-chain silicone polymer linked with chromophore. For example, benzyl malonate chromophores attached to specific points on a polysiloxane chain (PARASOL SLX).

A metal oxide, either alone or in combination with other sunscreen active agents disclosed herein, can have an anatase, rutile, or amorphous structure. Metal oxide particles can be uncoated or coated with a variety of materials including, without limitation, aluminium compounds such as aluminium oxide, aluminium stearate, aluminium laurate and the like; phospholipids such as lecithin; silicone compounds; and mixtures thereof. Various grades and forms of metal oxides are described in CTFA Cosmetic Ingredient Dictionary, Third Edition (1982), U.S. Pat. No. 4,820,508; and PCT Patent Application WO 1990/011067; each of which is hereby incorporated by reference in its entirety. Suitable grades of metal oxides for use in a composition disclosed herein can be purchased from commercial suppliers, including, without limitation, the MT micronized series from Tri-K Industries (Emerson, N.J.).

Micronized metal oxide compounds generally have a mean particle size ranging from about 10 nm to about 50 nm. For example, the titanium dioxide has a mean particle size of about 15 nm and this sunscreen active agent is available under the trade designation T-AVO (silica-coated titanium dioxide), MT-100F (modified with stearic acid and iron hydroxide), MT-100S (treated with lauric acid and aluminium hydroxide) and MT-100T (coated with stearic acid and aluminium compounds). Uncoated titanium dioxide compounds have a mean particle size of about 35 nm to about 50 nm are available under the trade designations MT-500B, MT-600B, MT-150W, respectively. Mixtures of two or more types and particle size variations of metal oxide compounds can be used in a composition disclosed herein. In a further embodiment, metal oxide compounds include, without limitation, Tioveil (Tioxide Group), 40% dispersions of surface-treated titanium dioxide in a range of cosmetic vehicles and Spectraveil (Tioxide Group), 60% dispersions of zinc oxide in a range of cosmetic vehicles.

A sunscreen active agent can be a UVA sunscreen active agent, a UVB sunscreen active agent, or a UVA/UVB or "broad spectrum" sunscreen active agent. A UVA sunscreen active agent exhibits absorptive, blocking and/or reflective properties within the wavelength region of between about 290 nm to about 320 nm. A UVA sunscreen active agent exhibits absorptive, blocking and/or reflective properties within the wavelength region of between about 320 nm to about 420 nm. A broad spectrum UVA/UVB sunscreen active agent exhibits absorptive, blocking and/or reflective properties within the wavelength region of between about 290 to about 420 nm. Non-limiting examples of a UVA sunscreen active agent include Avobenzone (butyl methoxydibenzoylmethane or Parsol 1789), bisdisulizole disodium (Neo Heliopan AP), diethylamino hydroxybenzoyl hexyl benzoate (Uvinul A Plus), ecamsule (Mexoryl SX) and menthyl anthranilate. Non-limiting examples of a UVB sunscreen active agent include amiloxate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), Padimate O (Escalol 507), phenylbenzimidazole sulfonic acid (Ensulizole), polysilicone-15 (Parsol SLX) and trolamine salicylate. Non-limiting examples of a broad spectrum UVA/UVB sunscreen active agent include bemotrizinol (Tinosorb S), benzophenones 1-12, dioxybenzone, drometrizole trisiloxane (Mexoryl XL), Iscotrizinol (Uvasorb HEB), octocrylene, oxybenzone (Eusolex 4360), sulisobenzone, bisoctrizole (Tinosorb M), titanium dioxide, and zinc oxide.

A sunscreen active agent disclosed herein can have a log P value indicating that the compound is soluble in an organic solvent. As used herein, the term "log P value" refers to the logarithm (base 10) of the partition coefficient (P) for a compound and is a measure of lipophilicity. It is a partition coefficient expressed as the log ratio of the concentrations of the solute in the solvent and is a measure of differential solubility of a compound in two solvents. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In an embodiment, a sunscreen active agent disclosed herein has a log P value of at least 4.0. In aspects of this embodiment, a sunscreen active agent disclosed herein has a log P value of, e.g. 1.1 or more, 1.2 or more, 1.3 or more, 1.4 or more, 1.5 or more, 1.6 or more, 1.7 or more, 1.8 or more, 1.9 or more, 2.0 or more, 2.1 or more, 2.2 or more, 2.3 or more, 2.4 or more, 2.5 or more, 2.6 or more, 2.7 or more, 2.8 or more, 2.9 or more, 3.0 or more, 3.1 or more, 3.2 or more, 3.3 or more, 3.4 or more, 3.5 or more, 3.06 or more, 3.7 or more, 3.8 or more, 3.9 or more 4.0 or more. In other aspects of this embodiment, a sunscreen active agent disclosed herein has a log P value of between, e.g., 1.8 to 4.0, 2.0 to 4.0, 2.1 to 4.0, 2.2 to 4.0, 2.3 to 4.0, 2.4 to 4.0, 2.5 to 4.0, 2.6 to 4.0, 2.8 to 4.0, 3.0 to 4.0, 3.1 to 4.0, 3.2 to 4.0, 3.3 to 4.0, 3.4 to 4.0, 3.5 to 4.0, 3.6 to 4.0.

A sunscreen active agent disclosed herein can be a FDA-approved sunscreen active agent or a European Union sunscreen active agent. In an embodiment, a sunscreen active agent marketed in the United States, preferred cosmetically-acceptable sunscreen active agents and concentrations (reported as a percentage by weight of the total cosmetic sunscreen composition, and referring to the final percentage of the sunscreen active agent after addition to the bodywash) include: aminobenzoic acid (also called para-aminobenzoic acid and PABA; 15% or less; a UVB absorbing organic sunscreen), avobenzone (also called butyl methoxy dibenzoylmethane; 3% or less, a UVA I absorbing organic sunscreen), cinoxate (also called 2-ethoxyethyl p-methoxycinnamate; 3% or less, a UVB absorbing organic sunscreen), decamsule, dioxybenzone (also called benzophenone-8; 3% or less, a UVB and UVA II absorbing organic sunscreen), homosalate (15% or less, a UVB absorbing organic sunscreen), menthyl anthranilate (also called menthyl 2-aminobenzoate; 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (7.5% or less, a UVB absorbing organic sunscreen), octyl salicylate (also called 2-ethylhexyl salicylate; 5% or less, a UVB absorbing organic sunscreen), oxybenzone (also called benzophenone-3; 6% or less, a UVB and UVA II absorbing organic sunscreen), padimate 0 (also called octyl dimethyl PABA; 8% or less, a UVB absorbing organic sunscreen), phenylbenzimidazole sulfonic acid (water soluble; 4% or less, a UVB absorbing organic sunscreen), sulisobenzone (also called benzophenone-4; 10% or less, a UVB and UVA II absorbing organic sunscreen), titanium dioxide (25% or less, an inorganic physical blocker of UVA and UVB), trolamine salicylate (also called triethanolamine salicylate; 12% or less, a UVB absorbing organic sunscreen), zinc oxide (25% or less, an inorganic physical blocker of UVA and UVB) and Tineubin (a UVA absorber manufactured by BASF).

In another embodiment, a second sunscreen active agent recognized as safe and effective by the US Food and Drug Administration includes, without limitation, p-aminobenzoic acid, Cinoxate, Avobenzone, digalloyl trioleate, dioxybenzone, ethyl 4-[bis(hydroxypropyl)]aminobenzoate, glyceryl aminobenzoate, homosalate, lawsone with dihydroxyacetone, menthyl anthranilate, octocrylene (ethyl 2-cyano-3,3-diphenyl acrylate), octyl salicylate, oxybenzone, Padimate O, phenylbenzimidazole sulfonic acid, red petrolatum, sulisobenzone, titanium dioxide, zinc oxide, including regular grades and grades of such fine particle size as enable the composition to be translucent or transparent, and triethanolamine salicylate. Additional sunscreen compounds recognized by European authorities include N,N,N-trimethyl-4-(2-oxoborn-3-ylidene methyl)anilinium methyl sulfate, 3-imidazol-4-ylacrylic acid and its ethyl ester, 2-phenylbenzimidazole-5-sulfonic acid and its salts, ethoxylated 4-aminobenzoic acid, amyl 4-dimethylaminobenzoate, 3,3,5-trimethylcyclohexyl-2-acetamidobenzoate, potassium cinnamate, 4-methoxycinnamic acid salts, propyl 4-methoxycinnamate, salicylic acid salts, amyl 4-methoxycinnamate, mexenone, sulisobenzone, 2-ethylhexyl 2-(4-phenylbenzoyl)-benzoate, 5-methyl-2-phenylbenzoxazole, sodium 3,4-dimethoxyphenylglyoxylate, 1,3-bis(4-methoxyphenyl)propane-1,3-dione, 5-(3,3-dimethyl-2-norbornylidene)-3-penten-2-one, alpha-(2-oxoborn-3-ylidene)-p-xylene-2-sulfonic acid, alpha-(2-oxoborn-3-ylidene) toluene-4-sulfonic acid and its salts, 3-(4-methylbenzylidene)bornan-2-one, 3-benzylidenebornan-2-one, alpha-cyano-4-methoxycinnamic acid and its hexyl ester, 1-p-cumenyl-3-phenylpropane-1,-3-dione, 4-isopropylbenzyl salicylate, cyclohexyl 4-methoxycinnamate, and 1-(4-t-butylphenyl)-3-(4-methoxyphenyl)propane-1,3-dione.

In another embodiment, a sunscreen active agent marketed in the European Union, preferred cosmetically-acceptable sunscreen active agents and concentrations (reported as a percentage by weight of the total cosmetic sunscreen composition, and referring to the final percentage of the sunscreen active agent after addition to the bodywash) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), Mexoryl XL, Neo heliopan AP, Benzophenone-9, Uvinul T 150, Uvinul A Plus, Uvasorb HEB, Parsol SLX, benzylidene camphor sulfonic acid (6% or less, expressed as acid), octocrylene (10% or less, expressed as acid), polyacrylamidomethyl benzylidene camphor (6% or less), octyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB® M), and bisethylhexyloxyphenol methoxyphenyl triazine. (10% or less, also called TINOSORB® S).

A sunscreen active agent useful for a composition disclosed herein are also described in, e.g., U.S. Pat. Nos. 5,169,624; 5,543,136; 5,849,273; 5,904,917; 6,224,852; 6,217,852; and Segarin et al., chapter Vil, pages 189 of Cosmetics Science and Technology, and Final Over-the-Counter Drug Products Monograph on Sunscreens (Federal Register, 1999:64:27666 27963), each of which are incorporated herein by reference in its entirety.

The sun protection factor (SPF) of a sunscreen active agent is a laboratory measure of the effectiveness of sunscreen. The SPF is the amount of UV radiation required to cause sunburn on the skin with the sunscreen on, as a multiple of the amount required without the sunscreen. SPF is determined by measuring the Minimal Erythemal Dose ("MED") and is defined as the threshold dose that produces skin erythema. The MED indicates the amount of energy irradiating the skin and the responsiveness of the skin to the radiation. In order to determine the MED, the reaction of the skin is recorded 24 hours after exposure to UV radiation. The minimal dose that induces any visible reddening at that point is defined as one MED. Redness that occurs immediately after exposure, however, and disappears during the following three to five hours is mainly caused by heat and is not comparable with real UV erythema. The SPF of a particular sunscreen active agent is obtained by dividing the MED of skin that has been protected by an active agent by the MED of unprotected skin. The higher the SPF, the more effective the active agent is in preventing an individual from skin erythema, which is on an individual is recognized as constituting a sunburn. SPF is generally measured in numerical increments that identify how long an individual can be exposed to UV radiation from the sun before that same individual will experience 1 MED. For example, utilizing a sunscreen with an SPF of 6 will allow an individual to be exposed to the sun six times longer than an SPF of 1 before that individual receives 1 MED. As the SPF value of a sunscreen increases, the less chance exists for development UV erythema of the skin. Methods for measuring SPF are described in, e.g., FDA monograph C.F.R. 21. A method for applying the sunscreen prior to measurement is as follows: Wet 50 cm² square area of testing site with 10 ml of water delivered with a syringe. Apply test sample as per FDA monograph to area. Work lather on the subject for 3 minutes to allow the product to absorb into the skin. Rinse area after 2 additional minutes with 20 ml of water. Pat dry and allow 15 minutes before exposure to radiation as per FDA monograph.

In an embodiment, a composition comprising one or more sunscreen active agents as disclosed herein may have an average SPF value ranging from about 2 to about 100. In aspects of this embodiment, a composition comprising one or more sunscreen active agents as disclosed herein may have an average SPF value of, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, a composition comprising one or more sunscreen active agents as disclosed herein may have an average SPF value of, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In yet other aspects of this embodiment, a composition comprising one or more sunscreen active agents as disclosed herein may have an average SPF value of, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

In other aspects of this embodiment, a composition comprising one or more sunscreen active agents as disclosed herein provides an average SPF value of, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100 for an average time period of, e.g., at least 4 hours, at least 8 hours, at least 12 hours, at least 16 hours, at least 20 hours, at least 24 hours, at least 36 hours, at least 48 hours, at least 60 hours, at least 72 hours, at least 4 days, at least 5 days, at least 6 days, at least 7 days, at least 8 days, at least 9 days, at least 10 days, at least 11 days, at least 12 days, at least 13 days or at least 14 days.

In yet other aspects of this embodiment, a composition comprising one or more sunscreen active agents as disclosed herein provides an average SPF value of, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100 for an average time period of, e.g., at about 4 hours to about 8 hours, about 4 hours to about 12 hours, about 4 hours to about 16 hours, about 4 hours to about 20 hours, about 4 hours to about 24 hours, about 4 hours to about 36 hours, about 4 hours to about 48 hours, about 4 hours to about 60 hours, about 4 hours to about 72 hours, about 8 hours to about 12 hours, about 8 hours to about 16 hours, about 8 hours to about 20 hours, about 8 hours to about 24 hours, about 8 hours to about 36 hours, about 8 hours to about 48 hours, about 8 hours to about 60 hours, about 8 hours to about 72 hours, about 12 hours to about 16 hours, about 12 hours to about 20 hours, about 12 hours to about 24 hours, about 12 hours to about 36 hours, about 12 hours to about 48 hours, about 12 hours to about 60 hours, about 12 hours to about 72 hours, about 16 hours to about 20 hours, about 16 hours to about 24 hours, about 16 hours to about 36 hours, about 16 hours to about 48 hours, about 16 hours to about 60 hours, about 16 hours to about 72 hours, about 20 hours to about 24 hours, about 20 hours to about 36 hours, about 20 hours to about 48 hours, about 20 hours to about 60 hours, about 20 hours to about 72 hours, about 24 hours to about 36 hours, about 24 hours to about 48 hours, about 24 hours to about 60 hours, about 24 hours to about 72 hours, about 36 hours to about 48 hours, about 36 hours to about 60 hours, about 36 hours to about 72 hours, about 48 hours to about 60 hours, about 48 hours to about 72 hours, about 60 hours to about 72 hours, about 3 days to about 4 days, about 3 days to about 5 days, about 3 days to about 6 days, about 3 days to about 7 days, about 3 days to about 8 days, about 3 days to about 9 days, about 3 days to about 10 days, about 4 days to about 5 days, about 4 days to about 6 days, about 4 days to about 7 days, about 4 days to about 8 days, about 4 days to about 9 days, about 4 days to about 10 days, about 5 days to about 6 days, about 5 days to about 7 days, about 5 days to about 8 days, about 5 days to about 9 days, about 5 days to about 10 days, about 6 days to about 7 days, about 6 days to about 8 days, about 6 days to about 9 days, about 6 days to about 10 days, about 7 days to about 8 days, about 7 days to about 9 days or about 7 days to about 10 days.

In other aspects of this embodiment, a composition comprising one or more sunscreen active agents as disclosed herein provides an average SPF value of, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100 for an average time period of, e.g., at least 4 hours, at least 8 hours, at least 12 hours, at least 16 hours, at least 20 hours, at least 24 hours, at least 36 hours, at least 48 hours, at least 60 hours, at least 72 hours, at least 4 days, at least 5 days, at least 6 days, at least 7 days, at least 8 days, at least 9 days, at least 10 days, at least 11 days, at least 12 days, at least 13 days or at least 14 days.

In yet other aspects of this embodiment, a composition comprising one or more sunscreen active agents as disclosed herein provides an average SPF value of, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100 for an average time period of, e.g., at least 4 hours to about 8 hours, about 4 hours to about 12 hours, about 4 hours to about 16 hours, about 4 hours to about 20 hours, about 4 hours to about 24 hours, about 4 hours to about 36 hours, about 4 hours to about 48 hours, about 4 hours to about 60 hours, about 4 hours to about 72 hours, about 8 hours to about 12 hours, about 8 hours to about 16 hours, about 8 hours to about 20 hours, about 8 hours to about 24 hours, about 8 hours to about 36 hours, about 8 hours to about 48 hours, about 8 hours to about 60 hours, about 8 hours to about 72 hours, about 12 hours to about 16 hours, about 12 hours to about 20 hours, about 12 hours to about 24 hours, about 12 hours to about 36 hours, about 12 hours to about 48 hours, about 12 hours to about 60 hours, about 12 hours to about 72 hours, about 16 hours to about 20 hours, about 16 hours to about 24 hours, about 16 hours to about 36 hours, about 16 hours to about 48 hours, about 16 hours to about 60 hours, about 16 hours to about 72 hours, about 20 hours to about 24 hours, about 20 hours to about 36 hours, about 20 hours to about 48 hours, about 20 hours to about 60 hours, about 20 hours to about 72 hours, about 24 hours to about 36 hours, about 24 hours to about 48 hours, about 24 hours to about 60 hours, about 24 hours to about 72 hours, about 36 hours to about 48 hours, about 36 hours to about 60 hours, about 36 hours to about 72 hours, about 48 hours to about 60 hours, about 48 hours to about 72 hours, about 60 hours to about 72 hours, about 3 days to about 4 days, about 3 days to about 5 days, about 3 days to about 6 days, about 3 days to about 7 days, about 3 days to about 8 days, about 3 days to about 9 days, about 3 days to about 10 days, about 4 days to about 5 days, about 4 days to about 6 days, about 4 days to about 7 days, about 4 days to about 8 days, about 4 days to about 9 days, about 4 days to about 10 days, about 5 days to about 6 days, about 5 days to about 7 days, about 5 days to about 8 days, about 5 days to about 9 days, about 5 days to about 10 days, about 6 days to about 7 days, about 6 days to about 8 days, about 6 days to about 9 days, about 6 days to about 10 days, about 7 days to about 8 days, about 7 days to about 9 days or about 7 days to about 10 days.

A composition comprising one or more sunscreen active agents as disclosed herein can maintain the SPF value relative to the initial application, even after exposure to water or other liquids, such as, e.g., by washing, rinsing, or swimming. In aspects of this embodiment, a composition comprising one or more sunscreen active agents as disclosed herein can maintain the SPF value relative to the initial application, even after exposure to water or other liquids by, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, a composition comprising one or more sunscreen active agents as disclosed herein can maintain the SPF value relative to the initial application, even after exposure to water or other liquids by, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In yet other aspects of this embodiment, a composition comprising one or more sunscreen active agents as disclosed herein can maintain the SPF value relative to the initial application, even after exposure to water or other liquids by, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

Multiple applications of a composition comprising one or more sunscreen active agents as disclosed herein can result in an increase in the SPF value relative to the initial application, even after exposure to water or other liquids, such as, e.g., by washing, rinsing, or swimming. For example, two or more, three or more, four or more, five or more, six or more, seven or more, eight or more, nine or more, or ten or more applications of a composition comprising one or more sunscreen active agents as disclosed herein can result in an increased in the SPF value relative to the initial application, even after exposure to water or other liquids.

In aspects of this embodiment, multiple applications of a composition comprising one or more sunscreen active agents as disclosed herein can increase the SPF value relative to the initial application, even after exposure to water or other liquids by, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, multiple applications of a composition comprising one or more sunscreen active agents as disclosed herein can increase the SPF value relative to the initial application, even after exposure to water or other liquids by, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In yet other aspects of this embodiment, multiple applications of a composition comprising one or more sunscreen active agents as disclosed herein can increase the SPF value relative to the initial application, even after exposure to water or other liquids by, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

In an embodiment, a composition comprising one sunscreen active agents. In another embodiment, a composition comprising a plurality sunscreen active agents. In aspects of this embodiment, a composition comprises, e.g., one or more, two or more, three or more, four or more, five or more, six or more, seven or more, eight or more, nine or more or ten or more different sunscreen active agents. In aspects of this embodiment, a composition comprises, e.g., about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10 different sunscreen active agents.

A composition disclosed herein comprises a sunscreen active agent in an amount sufficient to confer absorptive, blocking and/or reflective properties within the wavelength region of between about 290 to about 420 nm. In aspects of this embodiment, a composition disclosed herein comprises a sunscreen active agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a sunscreen active agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a sunscreen active agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In aspects of this embodiment, a composition disclosed herein comprises a sunscreen active agent in an amount sufficient to absorb, block and/or reflect, e.g., at least 10%, at least 20%, at least 30%, at least 40%, at least 50%, at least 60%, at least 70, at least 80%, at least 90%, or at least 95% of UVA radiation. In other aspects of this embodiment, a composition disclosed herein comprises a sunscreen active agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of UVA radiation.

In other aspects of this embodiment, a composition disclosed herein comprises a sunscreen active agent in an amount sufficient to absorb, block and/or reflect, e.g., at least 10%, at least 20%, at least 30%, at least 40%, at least 50%, at least 60%, at least 70, at least 80%, at least 90%, or at least 95% of incident radiation at wave lengths of about 290 nm to about 320 nm. In other aspects of this embodiment, a composition disclosed herein comprises a sunscreen active agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of incident radiation at wave lengths of about 290 nm to about 320 nm.

In aspects of this embodiment, a composition disclosed herein comprises a sunscreen active agent in an amount sufficient to absorb, block and/or reflect, e.g., at least 10%, at least 20%, at least 30%, at least 40%, at least 50%, at least 60%, at least 70, at least 80%, at least 90%, or at least 95% of UVB radiation. In other aspects of this embodiment, a composition disclosed herein comprises a sunscreen active agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of UVB radiation.

In other aspects of this embodiment, a composition disclosed herein comprises a sunscreen active agent in an amount sufficient to absorb, block and/or reflect, e.g., at least 10%, at least 20%, at least 30%, at least 40%, at least 50%, at least 60%, at least 70, at least 80%, at least 90%, or at least 95% of incident radiation at wave lengths of about 320 nm to about 420 nm. In other aspects of this embodiment, a composition disclosed herein comprises a sunscreen active agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of incident radiation at wave lengths of about 320 nm to about 420 nm.

In aspects of this embodiment, a composition disclosed herein comprises a sunscreen active agent in an amount sufficient to absorb, block and/or reflect, e.g., at least 10%, at least 20%, at least 30%, at least 40%, at least 50%, at least 60%, at least 70, at least 80%, at least 90%, or at least 95% of UVA/UVB radiation. In other aspects of this embodiment, a composition disclosed herein comprises a sunscreen active agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of UVA/UVB radiation.

In other aspects of this embodiment, a composition disclosed herein comprises a sunscreen active agent in an amount sufficient to absorb, block and/or reflect, e.g., at least 10%, at least 20%, at least 30%, at least 40%, at least 50%, at least 60%, at least 70, at least 80%, at least 90%, or at least 95% of incident radiation at wave lengths of about 290 nm to about 420 nm. In other aspects of this embodiment, a composition disclosed herein comprises a sunscreen active agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of incident radiation at wave lengths of about 290 nm to about 420 nm.

A composition disclosed herein comprises a cationic polymer to enhance the overall positive charge of the one or more sunscreen active agents and/or additional agents encapsulated in a cellulose derived capsule. The overall net positive charge of encapsulates promote and facilitate an electrostatic binding or attachment of encapsulates to a negatively charged molecule or surface, such as, e.g., charged components of skin and/or hair. A cationic polymer disclosed herein is not encapsulated by a cellulose derived capsule disclosed herein.

A cationic polymer useful in a composition disclosed herein include, without limitation, POLYMER JR (Union Carbide Corp.), a cationic cellulose ether derivative, JAGUAR® (Celanese-Stein Hall), cationic guar gums, GAFQUA™ (GAF Corporation), quaternary vinylpyrrolidone copolymer, CAE (Anjinomoto Co., Inc.), a DL-pyrrolidone carboxylic acid salt of L-cocoyl arginine ethyl ester, and MERQUAT™ (Merck & Co.), including MERQUAT™ 100, a highly charged cationic polymer prepared with dimethyldiallylammonium chloride homopolymer, and MERQUAT™ 550, a highly charged cationic copolymer prepared with dimethyldiallylammonium chloride and acrylamide.

In an embodiment, a cationic polymer includes, without limitation, a quaternium or a polyquaternium. Non-limiting examples of a polyquaternium-1, polyquaternium-2, polyquaternium-4 (CELQUAT L-200), polyquaternium-5, polyquaternium-6, polyquaternium-7, polyquaternium-10, polyquaternium-11, polyquaternium-15, polyquaternium-16, polyquaternium-22, polyquaternium-28, polyquaternium-32, polyquaternium-37, polyquaternium-39, polyquaternium-40, polyquaternium-41, polyquaternium-42, polyquaternium-44, polyquaternium-45, polyquaternium-46, polyquaternium-47 and polyquaternium-64.

A cationic polymer useful in a composition disclosed herein are also described in, e.g., U.S. Pat. Nos. 6,224,852; 3,816,616; 4,272,515; 4,298,494; 4,080,310; 4,048,301; 4,009,256; and 3,186,911, each of which is hereby incorporated by reference in its entirety.

A composition disclosed herein comprises a cationic polymer in an amount sufficient to confer an overall positive charge of the one or more sunscreen active agents and/or additional agents encapsulated in a cellulose derived capsule that promotes and facilitates an electrostatic binding or attachment of the encapsulates to a negatively charged molecule or surface, such as, e.g., charged components of skin and/or hair. In aspects of this embodiment, a composition disclosed herein comprises a cationic polymer in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a cationic polymer in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a cationic polymer in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition disclosed herein comprises a film former. As used herein, a film former creates a hydrophobic layer on a skin surface and/or hair that acts as a barrier which promotes and enhances the retention of the one or more encapsulated sunscreen active agents and/or additional agents, even after exposure to water or other liquids, such as, e.g., by washing, rinsing, or swimming. A film former disclosed herein is not encapsulated by a cellulose derived capsule disclosed herein. Non-limiting examples of a film former include an acrylic co-polymer, butylated hydroxytoluene (BHT), dimethicone, a lanolin derivative, petrolatum, a polyethylene, a polymer, a silicon derivative, a superfatted oil, a water-insoluble emollient, and a keratin or other protein derivative in an amino acid complex such as cysteine.

Non-limiting examples of a lanolin derivative include an acetylated lanolin.

Non-limiting examples of a water-insoluble emollient includes, fatty acids such as, e.g., oleic and stearic; fatty alcohols such a as, e.g., s cetyl, and hexadecyl (ENJAY); cocoa butter; shea oil; emollient esters such as, e.g., diisopropyl adipate, benzoic acid esters of $C_9$-$C_{15}$ alcohols, and isononyl iso-nonanoate; alkanes such as, e.g., mineral oil; silicones; such as, e.g., dimethyl polysiloxane and emollient ethers such as, e.g., polyoxypropylene butyl ethers and polyoxypropylene cetyl ethers.

Non-limiting examples of a polyethylene including, without limitation, PERFORMALENE® 400 (New Phase Technologies), a polyethylene having a molecular weight of 400 and PERFORMALENE® 2000 (New Phase Technologies) a polyethylene having a molecular weight of 2000.

Additional non-limiting examples of a film former include acacia gum, cellulose derivatives, guar derivatives, acrylamides copolymer, acrylamide/sodium aciylate copolymer, acrylate/acrylamide copolymer, acrylate/ammonium methacrylate copolymer, acrylates copolymer, acrylates/diacetoneacrylamide copolymer, acrylic/acrylate copolymer, adipic acid/dimethylaminohydroxypropyl diethlenetnamine copolymer, adipic acid/epoxypropyl/diethlenetriamine copolymer, albumen, allyl stearate/VA copolymer, aminoethylacrylate phosphate/acrylate copolymer, ammonium acrylates copolymer, ammonium alginate, ammonium vinyl acetate/acrylates copolymer, AMP acrylates/diacetoneacrylamide copolymer, balsam canada, balsam oregon, balsam peru, balsam tolu, benzoi acid/phthalic anhydride/pentaerythritol/neopentyl glycol/palmitic acid copolymer, benzoin extract, butadiene/acrylonitrile copolymer, butylated urea-formaldehyde resin, butyl benzoic acid/phthalic anhydride trimethylolethane copolymer, butyl ester of ethylene maleic anhydride copolymer, butyl ester of PVM/MA copolymer, calcium carrageenean, calcium/sodium PVM/MA copolymer, carboxymethyl hydroxyethyl cellulose, cellulose gum, collodion, copal, corn starch/aciylainide/sodium acrylate copolymer, damar, diethylene glycolamine/epichlorohydrin/piperazine copolymer, DMJ-IF, dodecanedoic acid/cetearyl alcoholglycol copolymer, ethylcellulose, ethylene/acrylate copolymer, ethylene/maleic anhydride copolymer, ethylene/vinyl acetate copolymer, ethyl ester of PVM/fvIA copolymer, flexible collodian, gum benzoin, gutta percha, hydroxybutyl methylceflulose, hydroxyethylcellulose, hydroxyethyl ethyl cellulose, hydroxypropylceilulose, hydroxypropyl guar, hydroxypropyl methylcellulose, isopropyl ester of PVM/MA copolymer, maltodextrin, melamine/formaldehyde resin, methacryloyl ethyl betainelmethacrylates copolymer, nitrocellulose, octylacrylamide/acrylates/butylaminoethylmethaciylate copolymer, octylacrylamide/acrylates copolymer, phthalic anhydride/glycerin/gycidyl decanoate copolymer, phthalic/trimellitic/glycols copolymer, polyacrylamide, polyaciylamidomethylpropane sulfone acid, polyacrylic acid, polybutylene terephthalate, polychlorotrifluoroethylene, polyethylacrylate, polyethylene, polyethylene terephthalate, polyisobutene, polystyrene, polyvinyl acetate, polyvinyl alcohol, polyvinyl butyral, polyvinyl imidazolinium acetate, polyvinyl laurate, polyvinyl methyl ether, potassium carrageenan, PVM/MA copolymer, PVP, PVP/dimethylaminoethymethacrylate copolymer, PVP/eicosene copolymer, PVP/ethyl methacrylate/methacrylic acid copolyerm, PVP/hexadecene copolymer, PVP/VA copolymer, PVP/vinyl acetate/itaconic acid copolymer, rosin, serum albumin, shellac, sodium acrylate/vinyl alcohol, copolymer, sodium carrageen, sodium polymethacrylate, sodium polystyrene sulfonate, starch/ acrylates/acrylamide copolymer, starch diethylaminoethyl ether, steaxyvinyl ether/maleic anhydride copolymer, styrene/acrylate/acrylonitrile copolymer, styrene/acrylate/ammonium methacrylate copolymer, styrene/maleic anhydride copolymer, styrene/PVP copolymer, sucrose benzoate/sucrose acetate isobutyrate/butyl benzyl phthalate copolymer, sucrose benzoate/sucrose acetate isobutyrate/butyl benzyl phthalate/methyl methaciylate copolymer, sucrose benzoate/sucrose acetate isobutyrate copolymer, toluenesulfonamide/formaldehyde resin, tragacath gum, vinyl acetate/crotonates copolymer, vinyl acetate/crotonic acid copolymer, vinyl acetate/crotonic acid/methacryloxybenzophenon-1 copolymer, vinyl acetate/crotonic aid/vinyl neodecanoate copolymer, and zein.

A film former useful in a composition disclosed herein include, without limitation, petroleum, an acrylate copolymer (DERMACRYL® 2.0, DERMACRYL® 79, DERMACRYL® AQF, DERMACRYL® C, DERMACRYL® E), a synthetic wax of branched polyalpha olefin polymers (PERFORMA® V 103, 260, 343, 825, 6038), a $C_{28}$-$C_{52}$ olefin/undecylenic acid copolymer (PERFORMA® V 6112) or MOISTUREGUARD™ (Engelhard), a film former comprising petrolatum, dimethicone, stearamidopropyl dimethylamine, stearate and tocopheryl acetate. A film former useful in a composition disclosed herein are also described in, e.g., U.S. Pat. Nos. 6,838,419, 6,838,088, 6,780,422, 6,531,118, and 5,916,541, each of which is incorporated herein by reference in its entirety.

A composition disclosed herein comprises a film former in an amount sufficient to create a hydrophobic layer on a skin surface and/or hair that acts as a barrier which promotes and enhances the retention of the one or more encapsulated sunscreen active agents and/or additional agents, even after exposure to water or other liquid. In aspects of this embodiment, a composition disclosed herein comprises a film former in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25%, at least 30%, at least 35% or at least 40% of the total weight of the composition. In other aspects of this embodiment, a composition disclosed herein comprises a film former in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25%, at most 30%, at most 35% or at most 40% of the total weight of the composition.

In other aspects of this embodiment, a composition disclosed herein comprises a film former in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35% or about 20% to about 40% of the total weight of the composition.

In an embodiment, a composition disclosed herein comprises can further comprise a surfactant metal complex to enhance the reflective property of a sunscreen composition disclosed herein. A surfactant metal complex disclosed herein is not encapsulated by a cellulose derived capsule disclosed herein.

A composition disclosed herein comprises a surfactant metal complex in an amount sufficient to promote or facilitate the reflection of UV light. In aspects of this embodiment, a composition disclosed herein comprises a surfactant metal complex in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a surfactant metal complex in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a surfactant metal complex in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition comprising one or more sunscreen active agents may further include one or more photostabilizing agents. Generally, a sunscreen active agent is photosensitive and is susceptible to photochemically-initiated degradation reactions. A photostabilizing agent stabilizes against light-induced degradation and help prevent a sunscreen agent disclosed herein from losing its effectiveness in absorbing, blocking and/or reflecting UV radiation. Photostabilizing agents do not absorb UV radiation, but act to inhibit degradation of a sunscreen active agent disclosed herein.

One type of photostabilizing agent helps stabilize a sunscreen agent disclosed herein structurally and geometrically through electrostatic and van der Waals interactions, which insulate the sunscreen active agent from being altered during the chemical reaction. Another type of photostabilizing agent protects a sunscreen active agent disclosed herein by dissipating the energy from UV radiation more quickly, thus reducing or even eliminating the possibility of a chemical reaction. This process is called energy transfer, and it can take place when a sunscreen agent disclosed herein and photostabilizing agent exchange electrons. In this way, a sunscreen agent disclosed herein is freed up to protect the skin by absorbing, blocking and/or reflecting harmful UV radiation, while the photostabilizing agent dissipates the energy.

A photostabilizing agent enables the use of less sunscreen active agent which increases the safety of a composition disclosed herein by reducing the amount of sunscreen active agent is used, thereby reducing the amount of sunscreen active agent that can be absorbed into the body and systemically distributed. In addition, reducing the amount of sunscreen active agent also reduces the overall cost of making a composition disclosed herein. Non-limiting examples of a photostabilizing agent include 4-methylbenzylidene camphor (MBC), an alpha olefin copolymer, Bemotrizinol (BTZ), Galangal extract, ethylhexyl methoxycrylene (SOLASTAY® 51), a hindered amine light stabilizer [HALS, 2,2,6,6-tetramethyl piperidine-based compounds including TINUVIN® compounds (BASF), CHIMASSORB® compounds (BASF) and LA compounds (Amfine)], hexylresorcinol, Polyester-25 (a bis-Methoxycrylene/octyldodecyl adipic acid/methylpropanediol copolymer)(SOLASTAY® P1), octasalicyalte (octasalate), trimethoxybenzylidene pentanedione (SYNOXYL® HSS, Sytheon, Ltd.), polyester-8. Photostabilizing agents useful in a composition disclosed herein are also described in, e.g., U.S. Pat. No. 5,801,244 and U.S. Patent Publications 2009/0074684 and 2013/0059924, each of which is incorporated herein by reference in its entirety.

Use of one or more photostabilizing agents increases the SPF of a composition disclosed herein. In aspects of this embodiment, a composition disclosed herein that further comprises one or more photostabilizing agents can increase the SPF value relative to a composition disclosed herein without the one or more photostabilizing agents by, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, a composition disclosed herein that further comprises one or more photostabilizing agents can increase the SPF value relative to a composition disclosed herein without the one or more photostabilizing agents by, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In aspects of this embodiment, a composition disclosed herein that further comprises one or more photostabilizing agents can increase the SPF value relative to a composition disclosed herein without the one or more photostabilizing agents by, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

In other aspects of this embodiment, a composition disclosed herein that further comprises one or more photostabilizing agents can increase the SPF value relative to a composition disclosed herein without the one or more photostabilizing agents by, e.g., at least 10%, at least 20%, at least 30%, at least 40%, at least 50%, at least 60%, at least 70, at least 80%, at least 90%, or at least 95%. In yet other aspects of this embodiment, a composition disclosed herein that further comprises one or more photostabilizing agents can increase the SPF value relative to a composition disclosed herein without the one or more photostabilizing agents by, e.g., at most 10%, at most 20%, at most 30%, at most 40%, at most 50%, at most 60%, at most 70, at most 80%, at most 90%, or at most 95%. In still other aspects of this embodiment, a composition disclosed herein that further comprises one or more photostabilizing agents can increase the SPF value relative to a composition disclosed herein without the one or more photostabilizing agents by, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100%.

A composition disclosed herein comprises a photostabilizing agent in an amount sufficient to help prevent a sunscreen agent disclosed herein from losing its effectiveness in absorbing, blocking and/or reflecting UV radiation. In aspects of this embodiment, a composition disclosed herein comprises a photostabilizing agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a photostabilizing agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a photostabilizing agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition comprising one or more sunscreen active agents may further include one or more other additional agents. Generally, an additional agents disclosed herein does not protect an individual against UV radiation or does so in a minimal manner.

An additional agent disclosed herein includes, without limitation, an analgesic agent, an aesthetic agent, an anti-acne agent, an anti-allergenic agent, an anti-cellulite agent, an anti-inflammatory agent, an antioxidant, an anti-pruritic agent, an anti-skin aging agent, an anti-skin wrinkling agent, an anti-microbial agent (e.g., antifungals, antibacterials, and antiparasitics), an anti-viral agent, a jellyfish repellent agent, a chelating agent, a deodorant, a dye, an essential oil, a hair growth promoter, a hair growth inhibitor, a hair bleaching agent, an anti-lice agent, an arachnid/insect repellent, a lipid, a medicinal agent (e.g., a biologic, a pharmaceutically active ingredient), a moisturizing agent, a pest repellent, a preservative, a silicone containing compound, a liquid hydrocarbon, a fragrance, a camouflage agent, a colorant, soothing agent (e.g. a cooling agent or a heating agent), skin whitening agent (e.g., a skin bleaching agent and a skin lightening agent), a skin nourishing agent, a structuring agent, a sunless tanning agent, a thickening agent, a vitamin, (e.g., skin rash, skin disease and dermatitis medications) or other molecule useful in protecting, moisturizing or otherwise enhancing the health and appearance of a skin surface or hair.

An aesthetic agent includes, without limitation, benzalkonium chloride, butamben picrate, benzocaine, bupivacaine, calamine, chlorprocaine, cocaine, dibucaine, dyclonine, etidocaine, hexylcaine, ketamine, lidocaine, mepivacaine, menthol, procaine, pramoxine, prilocaine, phenol, pramoxine, tetracaine, xylocalne, and pharmaceutically acceptable salts thereof.

An analgesic agent includes, without limitation, dyclonine hydrochloride, aloe vera, fentanyl, capsaicin, and the like.

An anti-acne actives include, without limitation, 5,7-dichloro-8-hydroxyquinoline, adapalene, azaleic acid, benzoyl peroxide, clindamycin, dapsone, erythromycin, long chain dicarboxylic acids, hydrocortisone, resorcinol, resorcinol acetate, salicylic acid, sulphur, tretinoin, urea, zinc, various natural agents such as those derived from green tree, and more. Other non-limiting examples of suitable anti-acne actives for use herein are described in U.S. Pat. No. 5,607,980, which is hereby incorporated by reference in its entirety.

An anti-allergenic agent includes, without limitation, antihistamines. In a further embodiment, antihistamines are, without limitation, $H_1$ or $H_2$ antagonists or other types of histamine release inhibitors. In an additional embodiment, $H_1$ antagonists are sedating or non-sedating, including, without limitation, diphenhydramine (Benadryl), chlorpheniramine, tripelennamine, promethazine, clemastine, doxylamine, benadryl and more. In a further embodiment, $H_1$-non-sedating antihistamines include, without limitation, astemizole, terfenadine, loratadine etc. Examples of $H_2$ antagonists include cimetadine, famotidine, nizatidine, and ranitidine. In an additional embodiment, histamine-release-inhibitors include, without limitation, cromolyn.

An anticellulite agent includes, without limitation, isobutylmethylxanthine, caffeine, theophylline, theobromine, aminophylline, yohimbine, and mixtures thereof. In an embodiment, examples of actives suitable for treating hair loss include, without limitation, potassium channel openers or peripheral vasodilators such as minoxidil, diazoxide, and compounds such as N*-cyano-N-(tert-pentyl)-N'-3-pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin EI and prostaglandin F2-alpha; fatty acids, such as oleic acid; diruretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical extracts including sandlewood, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof. Preferred hair loss treatment agents include minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

An anti-inflammatory agent includes, without limitation, steroidal, non-steroidal, and other compounds. In a further embodiment, steroidal anti-inflammatory agents include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradnelone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. In an additional embodiment, a steroidal anti-inflammatory for use is hydrocortisone.

A nonsteroidal anti-inflammatory agent includes, without limitation, oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (Astrazeneca and NicOx), Celecoxib (Pharmacia Corp.) (4-[5-(4-methylphenyl)-3-(trifluoromethyl)-1H-pyrazol-1-yl] benzenesulfonamide), Meloxicam (Boehringer Ingelheim Pharmaceuticals) (4-hydroxy-2-methyl-N-(5-methyl-2-thiazolyl)-2H-1,2GW-406381 (Glaxosmithkline), Etoricoxib (Merck & Co.), Rofecoxib (MERCK & Co.) (4-[4-(methylsulfonyl) phenyl]-3-phenyl-2(5H)-furanone), Lumiracoxib (Novartis Pharma AG), Valdecoxib (Pharmacia Corp.) (4-(5-methyl-3-phenyl-4-isox-azolyl) benzenesulfonamide), and Etodolac (Wyeth Ayerst Laboratories) ((±) 1,8-diethyl-1,3,4,9-tetrahydropyrano-[3,4-b]acid).

An anti-inflammatory agent also includes, without limitation, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, anise oil, garlic oil, ginger extract, vasoconstrictors such as phenylephrine hydrochloride, compounds of the Licorice (the plant *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific non-limiting examples of the foregoing include oil soluble licorice extract, the glycyrrhizic and glycyrrhetic acids themselves, mono ammonium glycyrrhizinate, monopotassium glycyrrhizinate, dipotassium glycyrrhizinate, 1-beta-glycyrrhetic acid, stearyl glycyrrhetinate, 3-stearyloxy-glycyrrhetinic acid, disodium 3-succinyloxy-beta-glycyrrhetinate, and combinations thereof.

An anti-microbial agent includes, without limitation, antifungal, antibacterial, and antiseptic compounds. Antifungal compounds include, but are not limited to, imidazole antifungals. Specific antifungals include, without limitation, butocouazole nitrate, miconazole, econazole, ketoconazole, oxiconizole, haloprogin, clotrimazole, and butenafine HCl, naftifine, terbinafine, ciclopirox, and tolnaftate. Antibacterials include, without limitation, an aminoglycoside, a tetracycline, a glycylcycline, a fluorocycline, an oxazolidinone, a peptidyl transferase (like an amphenicol and a pleuromutilin), a macrolide, a lincosamide, a streptogramin, a steroid antibacterial, a β-lactam (like a penicillin, a penem, a carbapenem, a cephem, a monobactam and a β-lactamase inhibitor), an antifolates (like a dihydrofolate reductase (DHFR) inhibitor, a sulphonamide, a topoisomerase inhibitor and a quinolone), an anaerobic DNA inhibitor (like a nitroimidazole derivative, a nitrofuran derivative and a rifamycin). Antiseptics include, without limitation, an acridine compound (like ethacridine lactate, 9-Aminoacridine and euflavine), a biguanide compound, an amidine compound (like 1,8-Diazabicyco[5.4.0]Undec-7-ene (DBU), diminazene, and benzamidine, chlorhexidine, dibrompropamidine, propamidine and hexamidine), a phenol compound (like hexachlorophene, policresulen, phenol, triclosan, triclocarban, chloroxylenol, biphenylol and fenticlor), a nitrofuran compound (like nitrofurazone), an iodine compound (iodine/octylphenoxypolyglycolether, povidone-iodine, and diiodohydroxypropane), a quinoline compound (like dequalinium, chlorquinaldol, qxyquinoline and clioquinol), a quaternary ammonium compound (like benzalkonium, benzethonium chloride, betrimonium, cetylpyridinium, cetrimide, benzoxonium chloride and didecyldimethylammonium chloride), a mercurial compound (like mercuric amidochloride, phenylmercuric borate, mercuric chloride, merbromin, thiomersal, mercuric iodide), a silver compound (like silver nitrate), an alcohol (like propanol, isopropanol, ethanol and other antiseptics like potassium permanganate, sodium hypochlorite, hydrogen peroxide, eosin, tosylchloramide and octenidine dihydrochloride.

Other antibacterial and antiseptic compounds include, without limitation, butocouazole phenol-TEA complex, mupirocin, triclosan, chlorocresol, chlorbutol, iodine, clindamycin, CAE (Anjinomoto Co., Inc., containing DL-pyrrolidone carboxylic acid salt of L-Cocoyl Arginine Ethyl Ester), povidone-iodine, polyhexanide, polyhexamethylene biguanide, polymyxin b sulfate-bacitracin, zinc-neomycin sulfate-hydrocortisone, chloramphenicol, methylbenzethonium chloride, manuka honey and erythromycin and antiseptics (e.g., benzalkonium chloride, benzethonium chloride, chlorhexidine gluconate, mafenide acetate, nitrofurazone, nitromersol), antimicrobial deodorant compounds, antiparasitics, including, without limitation, lindane and the like may be included in a composition disclosed herein.

In a further embodiment, antimicrobial with antifungal actives include, without limitation, β-lactam drugs, quinolone drugs, 2,4,4'-trichloro-2'-hydroxy diphenyl ether, 3,4,4'-trichlorocarbanilide, amanfadine, amanfadine hydrochloride, amanfadine sulfate, amikacin, amikacin sulfate, benzoic acid, butenafine, capreomycin, capreomycin sulfate, chlorhexidine, chlorhexidine gluconate, chlorhexidine hydrochloride, chlortetracycline, chlortetracycline hydrochloride, ciclopirox, ciprofloxacin, clindamycin hydrochloride, clotrimazole, doxycycline, doxycycline hydrochloride, econazole, efinaconazole, erythromycin, erythromycin estolate, erythromycin stearate, ethambutol, ethambutol hydrochloride, gentamicin, gentamicin sulfate, hexamidine isethionate, kanamycin, kanamycin sulfate, ketoconazole, lineomycin, lineomycin hydrochloride, luliconazole, methacycline, methacycline hydrochloride, methenamine, methenamine hippurate, methenamine mandelate, metronidazole, metronidazole hydrochloride, miconazole, miconazole hydrochloride, minocycline, minocycline hydrochloride, naftifine, neomycin, neomycin sulfate, netilmicin, netilmicin sulfate, norfloxacin, nystatin, octopirox, oxiconazole, oxytetracycline, parachlorometa xylenol, paromomycin, paromomycin sulfate, phenoxyethanol, phenoxy propanol, phenoxyisopropanol, pentamidine, pentamidine hydrochloride, paromomycin, salicylic acid, sertaconazole, streptomycin, streptomycin sulfate, sulconazole, tavaborole, terbinafine, tetracycline, tetracycline hydrochloride, tobramycin, tobramycin sulfate, tolnaftate, undecylenic acid, zinc oxytetracycline hydrochloride and zinc pyrithione.

An antioxidant includes, without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, vitamin E, coenzyme Q-10, ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, tocotrienols and their esters, and 6-hydroxy-2,5,7,8-tetramethylchroman-2-carboxylic acid (commercially available under the tradename TROLOX). Other suitable antioxidants include uric acid and its salts and alkyl esters, sorbic acid and its salts, lipoic acid, amines (e.g., N,N-diethylhydroxylamine, amino-guanidine), sulfhydryl compounds (e.g., glutathione, N-acetyl cysteine), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts, and a cascading antioxidant, such as, e.g., EMBLICA (EMD Chemicals) and synovia.

An anti-pruritic agent includes, without limitation, alclometasone dipropionate, betamethasone valerate, and isopropyl myristate MSD.

An anti-skin aging agent or anti-wrinkling agent includes, without limitation, a variety of agents, often in combination, that prevent or treat wrinkling through a variety of actions, including, without limitation, cosmetic products that contain hydroxy acids, retinol, retinoic, retinol palmitate, a derivative of vitamin A, (or its stronger, prescribed version Retin-A and Renova), bicyclic aromatic compounds with retinoid-type activity, including, without limitation, those described in EP 679 630. An anti-skin aging agent or anti-wrinkling agent includes, without limitation, bicyclic aromatic compounds, compounds which have retinoid-type activity, free-radical scavengers, a hydroxy acid, a keto acid or derivatives thereof. A "free-radical scavenger" includes, without limitation, α-tocopherol, superoxide dismutase, ubiquinol or certain metal-chelating agents. A hydroxy acid includes, without limitation, α-hydroxy acids such as lactic acid and glycolic acid or β-hydroxy acids such as salicylic acid and salicylic acid derivatives such as the octanoyl derivative; other hydroxy acids and keto acids include, without limitation, malic, citric, mandelic, tartaric or glyceric acids or the salts, amides or esters thereof. An anti-wrinkling agent and anti-skin aging agent include, without limitation, sulfur-containing D and L amino acids and their derivatives and salts, particularly the N-acetyl derivatives, a preferred example of which is N-acetyl-L-cysteine; thiols, e.g. ethane thiol; fat-soluble vitamins, ascorbyl palmitate, ceramides, pseudoceramides (e.g., pseudoceramides described in U.S. Pat. Nos. 5,198,210; 4,778,823; 4,985,547; 5,175,321, each of which is hereby incorporated by reference in its entirety), phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof. A fatty acid and/or fatty acid alcohol include, without limitation, straight or branched alkyl chains containing 12-20 carbon atoms and linoleic acid. In a further embodiment, anti-wrinkle actives include, without limitation, those described in U.S. Pat. No. 6,217,888, which description is incorporated herein by reference.

An anti-viral agents includes, without limitation, acyclovir, peniciclovir, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent application Ser. No. 09/421,084 (Beerse et al.); Ser. No. 09/421,131 (Biedermann et al.); Ser. No. 09/420,646 (Morgan et al.); and Ser. No. 09/421,179 (Page et al.), which were each filed on Oct. 19, 1999.

In an embodiment, quencher actives are used for singlet and triplet excited electron stabilization caused from photons of energy and to reduce or eliminate degradation. In an embodiment, quencher actives include, without limitation, electron receptors, including, without limitation, polycrylene. In an embodiment, an infrared reflective coating comprises an agent that reflects infrared radiation, for instance, without limitation, at a wavelength between about 0.74 μm to about 300 μm. In a further embodiment, an infrared reflective coating includes, without limitation, coatings which produce different amounts of gloss and reflection. In a further embodiment, a sunscreen composition with an infrared reflective coating is used by a soldier, police, national guard, governmental agent, including, without limitation, an individual working for the Federal Bureau of Investigation, Alcohol, and Tobacco & Firearms, Secret Service, Central Intelligence Agency, Department of Justice or any other governmental agent, whether located in the United States or outside the United States or other individuals who requires an infrared reflective coating.

A deodorant includes, without limitation, aluminium bromohydrate, potassium alum, sodium aluminium chlorohydroxy lactate, aluminium sulfate, aluminium chlorohydrate, aluminium-zirconium tetrachlorohydrate, an aluminium-zirconium polychlorohydrate complexed with glycine, aluminium-zirconium trichlorohydrate, aluminium-zirconium octachlorohydrate, aluminium sesquichlorohydrate, aluminium sesquichlorohydrex PG, aluminium chlorohydrex PEG, aluminium zirconium octachlorohydrex glycine complex, aluminium zirconium pentachlorohydrex glycine complex, aluminium zirconium tetrachlorohydrex glycine complex, aluminium zirconium trichlorohydrex glycine complex, aluminium chlorohydrex PG, zirconium chlorohydrate, aluminium dichlorohydrate, aluminium dichlorohydrex PEG, aluminium dichlorohydrex PG, aluminium sesquichlorohydrex PG, aluminium chloride, aluminium chloride hexahydrate, aluminium zirconium pentachlorohydrate, methylbenzethonium chloride, chlorophyllin copper complex and numerous other useful antiperspirant compounds listed in the CTFA Handbook at p. 56, incorporated herein by reference, and mixtures thereof.

A deodorant also includes, without limitation, astringent salts and bioactive compounds. An astringent salt includes, without limitation, organic and inorganic salts of aluminium, zirconium, zinc, and mixtures thereof. Anions of the astringent salt include, without limitation, sulfate, chloride, chlorohydroxide, alum, formate, lactate, benzyl sulfonate or phenyl sulfonate. An antiperspirant astringent salt includes, without limitation, aluminium halides, aluminium hydroxyhalides, zirconyl oxyhalides, zirconyl hydroxyhalides, and mixtures thereof. An aluminium salt includes, without limitation, aluminium chloride and the aluminium hydroxyhalides having the general formula $Al_2(OH)_xQ_yXH_2O$, wherein Q is chlorine, bromine or iodine; x is about 2 to about 5; x+y is about 6, wherein x and y are not necessarily integers; and X is about 1 to about 6. A zirconium compound includes, without limitation, zirconium oxy salts and zirconium hydroxy salts, also referred to as zirconyl salts and zirconyl hydroxy salts, and represented by the general empirical formula $ZrO(OH)_2 2\text{-}nz\, L_z$, wherein z varies from about 0.9 to about 2 and is not necessarily an integer; n is the valence of L; 2-nz is greater than or equal to 0; and L is selected, without limitation, from the group consisting of halides, nitrate, sulfamate, sulfate, and mixtures thereof.

A deodorant also includes, without limitation, a bacteriostatic quaternary ammonium compound, such as, e.g., cetyl trimethyl ammonium bromide, cetyl pyridinium chloride, benzethonium chloride, diisobutylbenzoxyethoxyethyldimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetralkylammonium carbonates and bicarbonates.

A hair bleaching agent includes, without limitation, a perborate salt or a persulfate salt. A hair growth inhibiting includes, without limitation, serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; imipramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. Preferred hair growth inhibitory agents include serine proteases, retinol, isotretinoin, betamethoisone, alpha-tocophenol and derivatives thereof, or mixtures thereof.

An anti-lice agent includes, without limitation, include organochlorines, such as, e.g., lindane, organophosphates, such as, e.g., malathion, carbamates, such as, e.g., carbaryl, pyrethrins, such as, e.g., pyrethrum, pyrethroids, such as, e.g., permethrin, phenothrin, bioallethrin, and spinosad, such as, e.g., spinosyn A and spinosyn D, bactrim, benzyl alcohol, crotamiton, dimeticone and ivermectin.

An arachnid/insect repellent includes, without limitation, a synthetic chemical compound or a compound purified from a natural source. Non-limiting examples of an arachnid/insect repellent that is a synthetic chemical compound, include, without limitation, N,N-Diethyl-m-toluamide (DEED, dimethyl phthalate, ethyl hexanediol, indalone, di-n-propylisocinchoronate, bicycloheptene, dicarboximide, dimethyl carbate, dimethyl phthalate, metofluthrin, indalone, permethrin, icaridin, nepetalactone, tetrahydrofuraldehyde ethyl butylacetylaminopropionate (IR-3535), p-menthane-3,8-diol (PMD), tricyclodecenyl allyl ether, ethylhexanediol, SS220 ((15,2'5)-Methylpiperidinyl-3-cyclohexen-1-carboxamide), an anthranilate-based arachnid/insect repellent, such as, e.g., methyl anthranilate, N,N-dimethylanthranilic acid (DMA), ethyl anthranilate (EA), and butyl anthranilate (BA) and hydroxyethyl isobutyl piperidine carboxylate.

Non-limiting examples of an arachnid/insect repellent that is a compound purified from a natural source includes plant-derived materials and sea-life including fish. Plant-derived materials with arachnid/insect repellent activity include, without limitation, plant oils derived from, e.g., achillea, Andrographis paniculata, anise, basil, bay, bergamot (e.g., Monardia fistulosa, Monarda didyma, Citrus bergamia, Monarda punctata), bitter orange peel, black pepper, calamus, camphor, cananga (e.g., java), cardamom, carnation (e.g., dianthus caryophyllus), cassia, castor, cedar (e.g., hinoki), cedarwood, celery, chamomile, cinnamon, Citrus aurantium amara, Citrus aurantium dulcis, Citrus unshiu, clary sage, clove (e.g., eugenia caryophyllus), clove bud, coriander, corn, cotton seed, Cymbopogon martini, eucalyptus, lemon eucalyptus, evening primrose, fennel, garlic, geranium, ginger, grapefruit, guaiacwood, gurjun balsam, hiba, jasmine, jojoba, juniper berry, lavender, lemon grass, lemon, lime, linseed, Litsea cubeba, marigold, marjoram, mint, mustard, neem, nutmeg, orange, orris root (e.g., iris florentina), patchouli (e.g., Pogostemon cablin), pepper, peppermint (e.g., *Mentha piperita*), pimento berry, pimento leaf, pine needle, pine, rose, rosemary (e.g., *Rosmarinus officinalis*), ryu, sage, sandalwood (e.g., santalum album), sassafras, sesame, soybean, spearmint, spice, spike lavender, starflower, tangerine, tea seed, tea tree, thyme, thulasi, tomato, turmeric, white cedar, white grapefruit, wintergreen and yellow nightshade.

A plant oil or derivative thereof may be extracted from a natural source or synthetically made and include racemic mixtures, enantiomers, diastereomers, hydrates, salts, solvates and metabolites, etc. Such oils generally contains as a major constituent an acyclic monoterpene alcohol or aldehyde, a benzenoid aromatic compound containing at least one oxygenated substituent or side chain, or a monocarbocyclic terpene generally having a six membered ring bearing one or more oxygenated substituents. Examples of suitable plant oils disclosed herein include, without limitation, α- or β-pinene; α-campholenic aldehyde; α-citronellol; α-isoamyl-cinnamic; α-pinene oxide; α-cinnamic terpinene; α-terpineol (e.g., 1-methyl-4-isopropyl-1-cyclohexen-8-ol); α-terpinene; A-terpinene; aldehyde C16 (pure); α-phellandrene; amyl cinnamic aldehyde; amyl salicylate; anethole; anisic aldehyde; benzyl acetate; benzyl alcohol; borneol; callicarpenal; carvacrol; carveol; cineole; cinnamaldehyde; cinnamic alcohol; cis-pinane; citral (e.g., 3,7-dimethyl-2,6-octadienal); citronella; citronellal; citronellol, citronellol dextro (e.g., 3-7-dimethyl-6-octen-1-ol); citronellol; citronellyl acetate; citronellyl nitrile; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin, 3-ethoxy-4-hydrobenzaldehyde; p-menthane-3,8-diol; eucalyptol (e.g., cineole); eucalyptus citriodora; eucalyptus globulus; eugenol (e.g., 2-methoxy-4-allyl phenol); fenchol; ferniol; florazon (e.g., 4-ethyl-α, α-dimethyl-benzenepropanal); galaxolide; geraniol (e.g., 2-trans-3,7-dimethyl-2,6-octadien-8-ol); geranyl acetate; geranyl nitrile; guaiacol; heliotropin; herbanate (e.g., 3-(1-methyl-ethyl) bicyclo(2,2,1) hept-5-ene-2-carboxylic acid ethyl ester); hydroxycitronellal; i-carvone; i-methyl acetate; ionone; isobutyl quinoleine (e.g., 6-secondary butyl quinoline); isobornyl acetate; isobornyl methylether; isoeugenol; isolongifolene; lavandin; limonene; linallol oxide; linallol; linalool; linalyl acetate; l-methyl acetate; longifolene; mandarin; mentha; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; methyl salicylate, mineral; musk ambrette; musk ketone; musk xylol; allylisothio-cyanate); myrcene; nerol; neryl acetate; nonyl aldehyde; myristica fragrans; para-cymene; para-hydroxy phenyl butanone crystals (e.g., 4-(4-hydroxyphenyl)-2-butanone); passion palmarosa oil; p-cymene; pennyroyal oil; perillaldehyde; petitgrain; phenyl ethyl alcohol (e.g., 1-phenyl ethyl alcohol and 2-phenyl ethyl alcohol); phenyl ethyl propionate (e.g., 1-phenyl ethyl propionate and 2-phenyl ethyl propionate); phenyl ethyl-2-methylbutyrate; pinane hydroperoxide; pinanol; pine ester; pinene; piperonal; piperonyl acetate; piperonyl alcohol; plinol; plinyl acetate; pseudo ionone; pyrethrum; rhodinol; rhodinyl acetate; rosalinsandenol; spirantol; terpinen-4-ol, terpenoid; terpineol; terpinolene; terpinyl acetate; tert-butylcyclohexyl acetate; tetrahydrolinalool; tetrahydrolinalyl acetate; tetrahydromyrcenol; thymol; trans-2-hexenol; trans-anethole and metabolites thereof; turpentine; vanillin (e.g., 4-hydroxy-3-methoxy benzaldehyde); vetiver; vitalizair; and the like.

A moisturizing agent prevents loss of moisture and/or hydrates the skin. A moisturizing agent includes, without limitation, an occulusive, which works by forming a thin film on the surface of the skin to prevent moisture loss, a humectant, which attracts water vapor from the air to moisturize the skin, and a restoration agent, which restore natural moisturizing factors to the skin. A moisturizing agent can be used as an after-care treatment of excessive sun exposure or sunburn. A moisturizing agent includes, without limitation, glycerin, chamomile, aloe, cetyl alcohol, grape seed oil, dimethicone, an alpha hydroxy acid, a silicone-based agent, a petrolatum-based agent and an antioxidant. A silicone-based agent includes, without limitation, cyclopentasiloxane, cyclohexasiloxane, cyclomethicone, dimethicone and phenyl trimethicone.

An alpha hydroxy acid includes, without limitation, glycolic acid, lactic acid, malic acid, citric acid and tartaric acid. An antioxidant includes, without limitation, 6-Hydroxymelatonin, acetyl-L-carnitine, a carotene, curcumin, edaravone, glutathione, hydroxytyrosol, L-carnitine, ladostigil, a lipoic acid like alpha-lipoic acid, melatonin, mofegiline, N-acetylcysteine, N-acetylserotonin, oleocanthal, oleuropein, a polyphenol, rasagiline, resveratrol, selegiline, selenium, tirlazad, tyrosol, uric acid, ubiquinol, ubiquinone, a vitamin A like a carotenoid, a vitamin C like an ascorbic acid, and a vitamin E like a tocopherol and a tocotrienol.

A fragrance includes, without limitation, alcohols (e.g., furaneol, 1-hexanol, cis-3-hexen-l-ol, menthol, or the like); aldehydes (e.g., acetaldehyde, hexanal, cis-3-hexenal, furfural, or the like); esters (e.g., fructone, hexyl acetate, ethyl methylphenylglycidate, methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin, black, cajuput oil, caraway, carrot seed, coriander, cypress, dill, fennel, helichyrsum, lavandin, lemon verena, bee balm, niaouli, palmarosa, petitgrain, tagetes, vetiver, or the like); ketones (e.g., dihydrojasmone, oct-1-en-3-one, 2-acetyl-1-pyrroline, 6-acetyl-2,3,4,5-tetrahydropyridine, or the like); lactones (e.g., γ-decalactone, γ-nonalactone, δ-octalactone, massoia lactone, sotolon, or the like); thiols (e.g., ethanethiol, grapefruit mercaptan, methanethiol, 2-methyl-2-propanethiol, or the like); linear terpenes (e.g., myrcene, geraniol, nerol, citral, lemonal, geranial, neral, citronellal, citronellol, linalool, nerolidol, or the like); cyclic terpenes (e.g., limonene, camphor, terpincol, ionone, thujuon, or the like); aromatic species (e.g., benzaldehyde, eugenol, cinnamaldehyde, ethyl maltol, vanillin, anisole, anethole, estragole, thymol, or the like); amines (e.g., thiethylamine, trimethylamine, cadaverine, pyridine, indole, skatole, or the like); or the like, or a combination comprising at least one of the foregoing fragrant molecules.

Further examples of fragrant molecules are geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenylcarbinyl acetate, p-tert-butyl-cyclohexyl acetate, isononyl acetate, vetiveryl acetate, vetiverol, alpha-n-amylcinammic aldehyde, alpha-hexylcinammic aldehyde, 2-methyl-3-(p-tert-butylphenyl)-propanol, 2-methyl-3-(p-isopropylphenyl)-propanal, 3-(p-tert-butylphenyl)-propanal, tricyclodecenyl acetate, tricyclodecenyl propionate, 4-(4-hydroxy-4-methyl-pentyl)-3-cyclohexene carbaldehyde, 4-(4-methyl-3-pente-nyl)-3-cyclohexene carbaldehyde, 4-acetoxy-3-pentyletetra-hydropyran, methyl-dihydrojasmonate, 2-n-heptylcyclopentanone, 3-methyl-2-pentylcyclopentanone, n-decanal, 9-decenol-I, phenoxyethyl isobutyrate, phenylacetaldehyde dimethyl acetal, phenylacetaldehyde diethyl acetal, geranonitrile, citronellonitrile, cedryl acetate, 3-isocamphycyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylioniones, irones, cis-3-hexenol and esters thereof, indane musk, tetralin musk, isochroman musk, macrocyclic ketones, macrolactone musk, ethylene brassylate, aromatic nitro-musk. Exemplary fragrant molecules include bergamot oil, coriander oil, dimethyl heptanol, dimethyl benzyl carbinyl acetate, geranyl acetate, citronellyl acetate, rose synthetic, geranium bourbon, hedione, iso eugenol, methyl eugenol styrallyl acetate, stemone, rose oxide laevo, aldehyde C-II undecyclic, derivatives of 2,6-dimethyl-2-alkoxy octan-7-ol, vertivert oil, vetiverol, vetiveryl, acetate, quaiac wood oil, esters ol-anthranilic acid, benzyl salicylate, benzyl benzoate, oak moss, eugenol, p-tert-butyl cyclohexyl acetate and coumarin.

A colorant, includes, without limitation, an agent used to color skin, nail, hair or other surface. A colorant, includes, without limitation, aluminum powder, annatto, bismuth citrate, bismuth oxychloride, bronze powder, caramel, carmine, β-carotene, chromium hydroxide green, chromium oxide green, copper powder, dihydroxyacetone, disodium EDTA-copper, ferric ammonium, ferrocyanide, ferric ferrocyanide, guaiazulene, guanine, henna, iron oxide, lead acetate, luminescent zinc sulfide, manganese violet, mica, potassium sodium copper chlorophyllin (chlorophyllin-copper complex), pyrophyllite, silver, titanium dioxide, ultramarine, zinc oxide, D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10 and D&C Yellow No. 11.

A camouflage agent, includes, without limitation, a UV reflector, a UV absorber, an infrared (IR) reflector and an IR absorber. A UV reflector reflects wavelengths from about 10 nm to about 400 nm.

An UV absorber aborbs wavelengths from about 10 nm to about 400 nm. Non-limiting examples of a UV absorber include an acrylate dye, a benzotriazole dye, a benzophenone dye and a phosphite dye. Specific UV absorber compounds include, without limitation, 2,4-dihydroxy benzophenone, 2,4-dihydroxybenzophenone, 2-hydroxy-4-methoxybenzophenone, 2,2'-dihydroxy-4,4'-dimethoxybenzophenone, 2,2',4,4'-tetrahydroxybenzophenone, 2-hydroxy-4-dodecyloxybenzophenone, 2-hydroxy-4-octyloxybenzophenone, 2-hydroxy-4-methoxybenzophenone, ethyl-2-cyano-3,3-diphenylacrylate, 2-ethylhexyl-2-cyano-3,3-diphenylacrylate, 2-ethylhexyl-2-cyano-3,3-diphenylacrylate, 2-hydroxy-4-methyoxy-benzophenone-5-sulfonic acid, 2,2'-dihydroxy-4,4'dimethoxy-5-sulfobenzophenone, 2-(2-hydroxy-5-methyl-phenyl)-2H-benzotriazole, 2-(2-hydroxy-5-carboxy-phenyl)-2H-benzotriazole, N-(p-ethoxycarbonylphenyl)-N'-ethyl-N'-phenylformamidine, poly-phenolic phosphite and tris (2,4-di-t-butylphenyl) phosphite.

An IR reflector reflects wavelengths from about 700 nm to about 1500 nm. Non-limiting examples of an IR reflector include a metal oxide. Specific IR reflector compounds include, without limitation, an iron oxide, a titanium dioxide and a zinc oxide.

An IR absorber absorbs wavelengths from about 700 nm to about 1500 nm. Non-limiting examples of an IR absorber include an azo dye, a croconium dye, a diphenylmethane dye, a heptamethinecyanine dye, a metal complex dye, a naphthalocyanine dye, a photchromic dye, a phthalocynine dye, a polymethine dye, a pyrylium dye, a quinone dye, a squarylium dye and a triphenylmethane dye. A metal complex dye includes, without limitation, a dithiolene metal complex, an indoanilinetype metal complex and a phenylenediamine metal complex. Specific IR absorber compounds include, without limitation, 2-[2-[2-Chloro-3-[(1,3-dihydro-1,3,3-trimethyl-2H-indol-2-ylidene)ethylidene]-1-cycloxen-1-yl]ethenyl]-1,3,3-trimethyl-1H indolium iodide, 2-[2-[2-Chloro-3-[(1,3-dihydro-1,3,3-trimethyl-2H-indol-2-ylidene)ethylidene]-1-cycloxen-1-yl]ethenyl]-1,3,3-trimethyl-1H indolium perchlorate, 2-[2-[2-Chloro-3-[(1,3-dihydro-3,3-dimethyl-1-propyl-2H-indol-2-ylidene)ethylidene]-1-cycloxen-1-yl]ethenyl]-3,3-dimethy-1-propyl-1H-indolium iodide, 2-[2-[2-Chloro-3-[(1,3-dihydro-3,3-dimethyl-1-propyl-2H-indol-2-ylidene)ethylidene]-1-cycloxen-1-yl]ethenyl]-3,3-dimethy-1-propyl-1H-indolium perchlorate, 2-[2-[2-Chloro-3-[(1,3-dihydro-3,3-dimethyl-1-(2-hydroxyethyl)-2H-indol-2-ylidene)ethylidene]-1-cycloxen-1-yl]ethenyl]-3,3-dimethy-1-(2-hydroxyethyl)-1H-indolium perchlorate, 2-[2-[3-[2-(1, 3-Dihydro-1,3,3-trimethyl-2H-indol-2-ylidene)-ethylidene]-2-(1-phenyl-1H-tetrazol-5-ylsulfanyl)-1-cyclohexen-1-yl]ethenyl]-1,3,3-trimethyl-3H-indolium chloride, 2-[2-[2-(4-Methylbenzeneoxy)-3-[2-(1,3-dihydro-1,1,3-trimethyl-2H-benz[e]indol-2-ylidene)ethylidene]-1-cylohexen-1-yl]ethenyl]-1,1,3-trimethyl-1H-benz[e]indolium 4-methylbenzenesulfonate, 2-[2-[2-chloro-3-[2-(1,3-dihydro-3,3-dimethyl-1-ethyl-2H-benz[e]indol-2-ylidene)ethylidene]-1-cylohexen-1-yl]ethenyl]-3,3-dimethyl-1-ethyl-1H-benz[e]indolium iodide, 2-[2-[2-chloro-3-[2-(1,3-dihydro-1,1,3-trimethyl-2H-benz[e]indol-2-ylidene)ethylidene]-1-cylohexen-1-yl]-ethenyl]-1,1,3-trimethyl-1H-benz[e]indolium 4-methylbenzenesulfonate, 1,4-Benzenediamine,N,N-bis[4-(dibutylamino)phenyl]-N',N'-diethyl-, radical ion (2+), bis [hexafluoroantimonate (1-)], 4,4',4"-tris(N,N-phenyl-3-methylphenylamino)triphenylammonium hexafluoroantimonate, 2-[2-[2-Chloro-3-[2-(1,3-dihydro-3,3-dimethyl-1-(4-sulfobutyl)-2H-indol-2-ylidene)-ethylidene]-1-cyclohexen-1-yl]ethenyl]-3,3-dimethyl-1-(4-sulfobutyl)-1H-indolium, 2-[7-(1,3-Dihydro-3,3-dimethy-1-(4-sulfobutyl)1-2H-benz[e]indol-2-ylidene)-1,3,5-heptatrienyl]-3,3-dimethyl-1-(4-sulfobutyl)-1H-benz[e]indolium, 2-[2-[2-(4-aminobenzenethio)-3-[(1,3-dihydro-3,3-dimethyl-1-(4-sulfobutyl)-2H-indol-2-ylidene)-ethylidene]-1-cycloxen-1-yl]-ethynyl]-3,3-dimethyl-1-(4-sulfobutyl)-3H-indolium, 2-[2-[2-Chloro-3-[2-(3-(4-sulfobutyl)-3H-benzothiazol-2-ylidene)-ethylidene]-1-cyclohexen-1-yl]ethenyl]3-(4-sulfobutyl)benzothiazolium, 2-[2-[2-Chloro-3-[2-(1,3-dihydro-3,3-dimethyl-1-(4-sulfobutyl)-2H-benz[e]-indol-2-ylidene)-ethylidene]-1-cyclohexen-1-yl]ethenyl]-3,3-dimethyl-1-(4-sulfobutyl)-1H-benz[e]indolium, 2-2-[2-[2-(4-aminothiophenyl)-3-[[1,3-dihydro-1,1-dimethyl-3-(4-sulfobutyl)-2H-benz[e]-indol-2-ylidene]ethylidene]-1-cyclohexen-1-yl]ethenyl]-1,1-dimethyl-3-(4-sulfonyl)-, tetrabutylammonium bis(3,6-dichloro-1,2-benzene-dithiolato)nickelate, tetrabutylammonium bis(3,4,6-trichloro-1,2-benzene-dithiolato)nickelate, tetrabutylammonium bis(4-methyl-1,2-benzenedithiolato) nickelate and Bis(4,4'-dimethoxydithiobenzyl) nickel. Other IR absorbers are described in Matsuoka, INFRARED ABSORBING DYES, pp. 220 (Springer Science & Business Media, 1990), which is hereby incorporated by reference in its entirety.

A soothing agent can be a cooling agent or a heating agent. Soothing agents include, without limitation, herb extracts, such as, e.g., aloe vera, alpha bisabolol, D-panthenol, allantoin, hamamelis, chamomile, yarrow; calendula, comfrey, witch hazel and other astringents, sea weed, and oat extracts; oils, selected from the group consisting of: almond oil, avocado oil, and comfrey; and essential oils, selected from the group consisting of: cardamone, eucalyptus, *Mentha piperita* (peppermint), hyssop, and rosemary; waxy or unctuous substances selected from the group consisting of: lanolin or vaselline jelly, minerals, selected from the group consisting of: zinc oxide, calamine and selenium; vitamins, selected from the group consisting of: tocopheryl acetate (vitamin E), and pharmaceutical agents selected from the group consisting of: analgesics, anesthetics, anti-inflammatory agents, and anti-histamines, and muscle relaxants; menthol, camphor, eugenol, eucalyptol, safrol, methyl salicylate, menthyl lactate, menthyl ethoxyacetate, menthone glycerinacetal, 3-I-menthoxypropane-1,2-diol, ethyl 1-menthyl carbonate, (1S,3S,4R)-p-menth-8-en-3-ol, menthyl pyrrolidone carboxylate, N-substituted-p-menthane-3-carboxamides hamamelis extract and ginger oil.

A cooling agent includes, without limitation, menthol; an isomer of menthol, a menthol derivative (e.g., menthol ethylene glycol carbonate, which is now known as Frescolat® type MGC, menthol Propylene Glycol Carbonate (Frescolat® type MPC), menthyl lactate (Frescolat ML®) and Menthone Glycerin Acetal (Frescolat MGA®) and 3-(I-Menthoxy)-1,2-propanediol); 4-Methyl-3-(1-pyrrolidinyl)-2[5H]-furanone; WS-23, Icilin, Icilin Unilever Analog, 5-methyl-4-(1-pyrrolidinyl)-3-[2H]-furanone; 4,5-dimethyl-3-(1-pyrrolidinyl)-2[5H]-furanone; isopulegol, 3-(I-menthoxy)propane-1,2-diol, 3-(I-menthoxy)-2-methylpropane-1,2-diol, p-menthane-2,3-diol, p-menthane-3,8-diol (Coolact® 38D), 6-isopropyl-9-methyl-1,4-dioxas-piro[4,5]decane-2-methanol, menthyl succinate and its alkaline earth metal salts, trimethylcyclohexanol, N-ethyl-2-isopropyl-5-methylcyclohexanecarb-oxamide, Japanese mint (Mentha arvensis) oil, peppermint oil, menthone, menthone glycerol ketal, menthyl lactate, 3-(I-menthoxy)ethan-1-ol, 3-(I-menthoxy)propan-1-ol, 3-(I-menthoxy)butan-1-ol, I-menthylacetic acid N-ethylamide, I-menthyl-4-hydroxypentanoate, I-menthyl-3-hydroxybutyrate, N,2,3-trimethyl-2-(1-methylethyl)-butanamide, spearmint oil and coolact 38D.

A heating agent includes, without limitation, polyhydric alcohols, capsicum (red pepper) powder, a capsicum tincture, capsicum extract, capsaicin, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

A jellyfish repellent agent is used for repelling or preventing stings from memebers of the phylum Cnidaria (e.g., jellyfish, sea anemone, and coral), the phylum Myxozoa, or the like). A jellyfish repellent agent includes, without limitation, one or both of an antihistamine agent and one or more cations. An antihistamine agent includes, without limitation, diphenhydramine, cimetidine or tripelennamine or other histamine binding inhibitors. In aspects of this embodiment, a jellyfish repellent agent is present in a concentration from about 0.0005% to about 2.0% or from about 0.001% to about 0.2%, or similar effective amount). A cation includes, without limitation, metal cations and alkali cations such as, e.g., $Ca^{++}$, $K^+$, $Na^+$, $Mn^{++}$, $Co^{++}$, $Mg^{++}$, or $Fe^{++}$, or other substance which is capable of supplying positively charged ions. In aspects of this embodiment, a cation is present in a concentration of from about 5 mM to about 1M, or about 25 mM to about 500 mM, or from about 50 mM to about 200 mM.

A skin whitening agent includes, without limitation, skin lightening agent and skin bleaching agent. A skin whitening agent include, without limitation, alpha hydroxyl acids ("AHA's"), arbutin, cinnamomum subavenium, EMBLICA (also an antioxidant), hydroquinone, kojic acid, azelaic acid, ascorbic acid and derivatives thereof (e.g., magnesium ascorbyl phosphate or sodium ascorbyl phosphate), niacinamide, a licorice extract (e.g., glabridin), a mulberry extracts and a placental extract. A skin whitening agent can include a depigmentation agent including, without limitation, monobenzone or mequinol. Additional skin whitening agents are also described in WO 1995/34280, WO 1995/07432, and WO 1995/23780.

A sunless tanning agent includes, without limitation, dihydroxyacetone (DHA); glyceryl aldehyde; tyrosine and tyrosine derivatives such as, e.g., malyltyrosine, tyrosine glucosinate, and ethyl tyrosine; phospho-DOPA, indoles and derivatives thereof.

A vitamin includes, without limitation, Vitamin A and derivatives thereof (including, for example, retinol), ascorbic acid (Vitamin C and derivatives), Vitamin B (e.g., riboflavin, vitamin $B_2$), biotin, Vitamin D (all forms), Vitamin E and derivatives thereof such as tocopheryl acetate, beta-carotene, panthothenic acid and more.

A skin care agent includes, without limitation, those found in the CTFA Cosmetic Ingredient Handbook, Seventh Edition, 1997 and the Eighth Edition, 2000 and Remington's Pharmaceutical Sciences, 20th Ed., Lippincott Williams & Witkins, Baltimore, Md. (2000) (hereinafter Remington's), U.S. Pharmacopeia and National Formulary, The United States Pharmacopeia Convention, Inc., Rockville, Md. and Physician's Desk Reference, Medical Economics Co., Inc., Oradell, N.J. all of which are incorporated herein by reference.

A chelating agent is a compound that chelates or binds metallic ions, such as with a heterocyclic ring structure so that the ion is held by chemical bonds from each of the participating rings. Chelating agent includes, without limitation, ethylene diaminetetraacetic acid (EDTA), EDTA disodium, calcium disodium edetate, EDTA trisodium, EDTA tetrasodium and EDTA dipotassium.

A preservative, includes, without limitation, citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidazolines (e.g., imidiazolinylurea), triclosan, hydantoins (e.g., dimethyloldimethylhydantoin), isothiazolidinone compounds and mixtures thereof, KATHON® CG and KATHON® CGII, which contain methylchloroisothiazolinone and methylisothiazolinone (Rohm and Haas). Optiphen A thickening agent (or gallant) is used to adjust the texture and viscosity of a composition disclosed herein. A thickening agent includes, without limitation, CARBOPOL™ resins [e.g., 934, 971, 974, 980, 981] and PEMULEN™ [TR-1 and TR-2] [both CARBOPOL™ and PEMULEN™ are registered trademarks of BF Goodrich], Noveon AA-1, ETD resins, and ULTREZ™ resins or carbomers.

A medicinal agent includes, without limitation, camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate, burn relief agents, such as o-amino-p-toluenesulfonamide monoacetate; dermatitis relief agents, such as the active steroid amcinonide, diflorasone diacetate, and hydrocortisone; diaper rash relief agents, such as methylbenzethonium chloride and the like; a photochemotherapeutic like aminolevulinic acid, methyl aminolevulinic acid or methoxsalen; a herpes treatment agent, such as O-[(2-hydroxyethoxy)methyl]guanine; psoriasis, seborrhea and scabicide agents, such as shale oil and derivatives thereof, elubiol, ketoconazole, coal tar and petroleum distillates, salicylic acid, zinc pyrithione, selenium sulfide, hydrocortisone, sulfur, menthol, psoralen, pramoxine hydrochloride anthralin, and methoxsalen; steroids, such as Alclometasone, amcinonide, betamethasone, clobetasol, clocortolone, diflorasone, desonide, desoximetasone, fluocinolone, fluocinonide, flurandrenolide, fluticasone, halcinonide, halobetasol, hydrocortisone, mometasone, prednicarbate, triamcinolone, 2-(acetyloxy)-9-fluoro-1',2',3',4'-tetrahydro-11-hydroxy-pregna-1,4-dieno [1 6,17-b]naphthalene-3,20-dione and 21-chloro-9-fluoro-1',2',3',4'-tetrahydro-11 b-hydroxy-pregna-1,4-dieno[16z, 17-b]naphthalene-3,20-dione. Other medicinal agents include, without limitation, ones for treating dermatological conditions such as psoriasis, acne, eczema, and other skin conditions due to disease, pathology, accident, as well as medicinal agents useful in the treatment of exposure to poison oak, poison ivy, poison sumac, and the like.

In an embodiment, additional ingredients which can be present in a sunscreen composition include, without limitation, a fragrance, a dye, an oil, a non-polar wax, a liquid hydrocarbon and/or an antimicrobial material. A non-polar wax, includes, without limitation, ester waxes, diester waxes, hydrocarbon waxes, silicone waxes and triglyceride waxes and mixtures thereof. An antimicrobial material includes, without limitation, triclocarban, triclosan, iodophors, iodine formulations, phenolic compounds, e.g. hexachlorophene, and bisbiguanides, e.g. chlorhexidene gluconate, and the like. See, e.g. U.S. Pat. Nos. 6,827,795; 6,517,854; 6,010,817; 5,173,216; 5,719,113; 5,259,984; 5,562,912; 5,629,006; 5,728,662; 5,767,163; 5,750,579; 5,591,442; 5,650,143; 5,772,640; and 4,478,821, each of which is hereby incorporated by reference in its entirety.

In aspects of this embodiment, a composition disclosed herein may comprise, e.g., at least one, at least two, at least three, at least four, at least five, at least six, at least seven, at least eight, at least nine or at least ten additional agents. In other aspects of this embodiment, a composition disclosed herein may comprise, e.g., at most one, at most two, at most three, at most four, at most five, at most six, at most seven, at most eight, at most nine or at most ten additional agents. In yet other aspects of this embodiment, a composition disclosed herein may comprise, e.g., about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10 additional agents.

A composition disclosed herein comprises an additional agent in an amount sufficient to promote or facilitate the function or activity of that additional agent. The amount of additional agent can range from 0.00% to 99.9% by total weight of the composition, or any integer or range in between. In aspects of this embodiment, a composition disclosed herein comprises an additional agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises an additional agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises an additional agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In an embodiment, an agent disclosed herein can have more than one function. For example, without limitation, inorganic blockers such as Tioveil and Spectraveil (both of the Tioxide Group), can act as film-formers and have other advantageous uses. In an embodiment, a sunscreen composition includes, without limitation, a wide variety of additional components selected so as to avoid any undesirable reaction with the primary components (e.g., one or more of the sunscreen active agents) of the composition. The CTFA Cosmetic Ingredient Handbook, Seventh Edition, 1997 and the Eighth Edition, 2000 (incorporated by reference herein), provide a broad source of possible cosmetic and pharmaceutical ingredients typically used in skin care compositions. In an embodiment, additional components include, without limitation, one or more of the following: Absorbents, abrasives, anticaking agents, antifoaming agents, binders, biological additives, buffering agents, bulking agents, chelating agents/sequestrants (e.g., disodium EDTA), chemical additives, colorants, cosmetic astringents, cosmetic biocides, denaturants, drug astringents, emollients (including glycerin alovera, and Vitamins A, C, and D [hydrating agents and skin protectants]), foam boosters, fragrance components, gums, humectants/moisturizers (including urea, guanidine, glycolic acid, polyhydroxy alcohols such as sorbitol, glycerin, hexanetriol, propylene glycol, hexylene glycol and the like, polyethylene glycol, sugars and starches, sugar and starch derivatives, D-panthenol, hyaluronic acid, lactamide monoethanolamine, acetamide monoethanolamine, and mixtures thereof), hydrotropes, neutralizing agents, opacifying agents and pigments, pH adjusters, plasticizers, preservatives, propellants, reducing agents, skin bleaching agents, skin protectants, solubilizing agents, and suspending agents (e.g., Carbomer 1382).

A sunscreen active agent, a photostabilizing agent and/or an additional agent disclosed herein can be encapsulated in a cellulose derived capsule. Generally, encapsulation of a molecule, including, without limitation, a sunscreen active agent, a photostabilizing agent and/or an additional agent disclosed herein involves trapping the agent into a vesicle, such as, e.g., a microsphere (or microcapsule) or nanosphere (or nanocapsule). In addition, a cellulose derived capsule itself can has UV light absorption properties that can increase the protective effectiveness of a composition disclosed herein. A cellulose derived capsule can be prepared in large quantities without a high reaction time and drying step and the preparation and purification of cellulose derived capsules are well known to a person skilled in the art, see, e.g., U.S. Pat. Nos. 8,039,015 and 8,685,425, each of which is incorporated by reference in its entirety.

A cellulose derived capsule can have either a hard or a flexible shell. A flexible shell enables for the tight packing of the capsules on the surface of the skin to form an encapsulate layer, prevents breakage or rupture of the capsules upon friction or other external force and/or enables capsule to have high load rates. For example, applications involving a non-encapsulated sunscreen active agent, photostabilizing agent and/or additional agent is absorbed directly into the skin within about 1 hour, thereby providing limited protection from harmful UV light produced by the sun or man-made light sources and/or other beneficial results. Flexible cellulose derived capsules containing one or more sunscreen active agents, photostabilizing agents and/or additional agents disclosed herein form an encapsulation layer on top of the skin surface. The flexibility of the cellulose derived capsules enable dense packing of the capsules to form a strong cohesive encapsulate layer. Among other things, this encapsulate layer acts like a shield to physically protect a skin surface from harmful UV light generated by the sun or a man-made light source. This encapsulate layer appears to be maintained on the surface of skin for upwards of 8 or more hours.

Another advantage of flexible cellulose derived capsules is that the flexible nature of these encapsulates prevents breakage or rupture of the capsules upon friction or other external force, resulting in the release of their contents onto a skin surface. A sunscreen active agent that is applied directly to a skin surface is readily absorbed by the skin within 1 hour. As discussed above, a non-encapsulated sunscreen active agent, photostabilizing agent and/or additional agent is absorbed directly into the skin within about 1 hour. This is detrimental because protection from the sun or other benefit is quickly lost and repeated applications are required to maintain protection. In addition, absorption of many sunscreen active agents can be toxic to some degree and create health problems for the user. Encapsulated sunscreen active agents, photostabilizing agents and/or additional agents contained within cellulose derived capsules prevents these detrimental effects by forming an encapsulate layer on a skin surface. This allows the sunscreen active agents to absorb and or reflect harmful UV light or provide other beneficial effects for a much longer period of time, namely 8 or more hours, because these agents are kept at the skin surface. In addition, since the sunscreen active agents are contained within flexible cellulose derived capsules, absorption into the skin is minimized.

Encapsulation increases the stability of the sunscreen composition by protecting the encapsulated sunscreen active agent, photostabilizing agent and/or additional agent disclosed herein. In addition, encapsulation increases the effectiveness of the sunscreen composition to protect an individual from deleterious effects of UV exposure by creating a encapsulate layer that physically shield the skin layer from UV light. Furthermore, encapsulation also minimizes the absorption of sunscreen active agent, a photostabilizing agent and/or an additional agent disclosed herein into the dermis and subsequent systemic distribution in the body.

In an embodiment, sunscreen active agent, a photostabilizing agent and/or an additional agent disclosed herein is encapsulated in a cellulose derived capsule. In another embodiment, one or more sunscreen active agents, photostabilizing agents and/or additional agents and disclosed herein are encapsulated in a cellulose derived capsule and one or more sunscreen active agents, photostabilizing agents and/or an additional agents disclosed herein are not encapsulated. In another embodiment, one or more additional agents disclosed herein are not encapsulated. In another embodiment, one or more one or more sunscreen active agents and photostabilizing agents disclosed herein are encapsulated, but one or more additional agents disclosed herein are not encapsulated.

In an embodiment, depending on the vehicle of choice, the vesicle may remain intact following application to an individual or it may break open when applied. In an embodiment the cellulosic capsule may remain intact depending on the wetting capability of the surrounding substrate. In a further embodiment, the vesicle may open when applied over a period of time, wherein the period of time can be continuous until the last vesicle breaks open or at one or more defined period after application to an individual. In an embodiment, the stability, durability, and/or SPF protection provided by a sunscreen active agent in a composition disclosed herein can be increased through the selection of a particular cellulose derived capsule that meets the desired requirements.

In an embodiment, a cellulose derived capsule is a capsule wherein at least a portion of the capsule is composed of a cellulose derivative. In another embodiment, a cellulose derived capsule is a capsule wherein the capsule is composed solely of a cellulose derivative. In a further embodiment, a cellulose derived capsule includes one or more anionic components as part of the capsule. In a further embodiment, a cellulose derived capsule includes one or more cationic components as part of the capsule. In aspects of this embodiment, a cellulose derived capsule disclosed herein comprises of 0.1%-5% wt/wt of cellulosic material, 5%-20% wt/wt of cellulosic material, 20%-50% wt/wt of cellulosic material or 50%-70% wt/wt of cellulosic material.

In another embodiment, a sunscreen composition contains cellulose derived capsules comprising cellulose and/or one or more cellulose derivatives. A cellulose derivative for use in a cellulose derived capsule includes without limitation, a cellulose ether or a cellulose ester. Non-limiting examples of a celluloe ether include ethyl cellulose, methyl cellulose, ethylmethyl cellulose, hydroxyethyl cellulose, hydroxypropyl cellulose, hydroxyethylmethyl cellulose, hydroxypropylmethyl cellulose, ethyl hydroxyethyl cellulose, carboxymethyl cellulose, or any salt therefrom. Non-limiting examples of a celluloe ester include cellulose acetate, cellulose acetate phthalate, cellulose acetate butyrate, cellulose acetate trimelitate, hydroxupropylmethyl cellulose phthalate, or any salt therefrom. Additional cellulose derivitiives are described in, e.g., CELLULOSE: STRUCTURE AND PROPERTIES, DERIVITIVES AND INDUSTRIAL USES, eds. Lejeune and Deprez, pp. 528 (2010); CELLULOSE AND CELLULOSE DERIVATIVES, Kenji Kamide, (2005); Doelker, *Cellulose Derivatives*, pp. 199-265, ADVANCES IN POLYMER SCIENCE, vol. 107 (2005), each of which is hereby incorporated by reference in its entirety. In an aspect of this embodiment, the cellulose derivative a sunscreen composition contains cellulose derived capsules comprising cellulose, a cellulose ether derivitieve, a cellulose eseter derivative, any salt therefrom, or any combination therefrom. In another aspect of this embodiment, the cellulose derivative a sunscreen composition contains cellulose derived capsules comprising cellulose, ethyl cellulose, methyl cellulose, ethylmethyl cellulose, hydroxyethyl cellulose, hydroxypropyl cellulose, hydroxyethylmethyl cellulose, hydroxypropylmethyl cellulose, ethyl hydroxyethyl cellulose, carboxymethyl cellulose, cellulose acetate, cellulose acetate phthalate, cellulose acetate butyrate, cellulose acetate trimelitate, hydroxupropylmethyl cellulose phthalate, any salt therefrom, or any combination therefrom. In an aspect of this embodiment, the cellulose derivative a sunscreen composition contains cellulose derived capsules comprising cellulose, a cellulose ether derivitieve, any salt therefrom, or any combination therefrom. In another aspect of this embodiment, the cellulose derivative a sunscreen composition contains cellulose derived capsules comprising cellulose, ethyl cellulose, methyl cellulose, ethylmethyl cellulose, hydroxyethyl cellulose, hydroxypropyl cellulose, hydroxyethylmethyl cellulose, hydroxypropylmethyl cellulose, ethyl hydroxyethyl cellulose, carboxymethyl cellulose, any salt therefrom, or any combination therefrom. In an aspect of this embodiment, the cellulose derivative a sunscreen composition contains cellulose derived capsules comprising cellulose, a cellulose eseter derivative, any salt therefrom, or any combination therefrom. In another aspect of this embodiment, the cellulose derivative a sunscreen composition contains cellulose derived capsules comprising cellulose, cellulose acetate, cellulose acetate phthalate, cellulose acetate butyrate, cellulose acetate trimelitate, hydroxupropylmethyl cellulose phthalate, any salt therefrom, or any combination therefrom. In an aspect of this embodiment, the cellulose derivative used in a cellulose derived capsule is hydroxypropylcellulose or a salt therefrom. In an aspect of this embodiment, the cellulose derivative used in a cellulose derived capsule is carboxymethylcellulose or a salt therefrom, such as, e.g., sodium carboxymethyl cellulose.

In a further embodiment, the cellulose derived capsules in a sunscreen composition are of different sizes and/or contain multiple layers. In an additional embodiment, each layer of a cellulose derived capsule can contain one or more sunscreen active agents, photostabilizing agents and/or additional agents. In a further aspect, the present invention discloses that the cellulose derived capsule is comprised of two or more layers, further, wherein each layer can contain a different sunscreen active agent, wherein each layer can contain the same sunscreen active agent, wherein each layer can contain a different sunscreen active agent, wherein at least one layer can contain a different sunscreen active agent than at least one other layer, wherein at least one layer can contain a sunscreen active agent and at least one layer contains an antioxidant, wherein at least one layer can contain a sunscreen active agent and at least one layer contains a vitamin, wherein at least one layer can contain a sunscreen active agent and at least one layer contains an anti-inflammatory, wherein at least one layer can contain a sunscreen active agent and at least one layer can contain an astringent.

Besides encapsulating one or more sunscreen active agent, a photostabilizing agent and/or an additional agent disclosed herein, a cellulose derived capsule disclosed herein forms a physical layer on a skin surface that acts as a protective barrier. As such, a composition disclosed herein may include cellulose derived capsules without any sunscreen active agents, photostabilizing agents and additional agents disclosed herein (i.e., filled with an insert liquid like a hydrophobic component, such as, e.g., an oil). In such an application, the hydrophobic component-filled cellulose derived capsules are designed so as to experience minimal or no leakage or decomposition when applied to the skin. The hydrophobic component-filled cellulose derived capsules are eventually removed from the skin through repeated washing and/or normal sloughing of the external skin cell layers. Especially for agents used for one-time or very few exposures, such as can occur for personnel engaged in combating or containing terrorist attacks or in warfare, the invention provides a means to deliver a last line of defense on the skin of personnel where the active used in the microcapsules may be one that is not appropriate for long-term use, but that is appropriate for a limited number of applications in order to protect the wearer from a greater risk (e.g., cellulose derived capsules, including, without limitation, microcapsules, encapsulating lead to protect against a radiation attack).

A cellulose derived capsule has sufficient size to form a protective layer on top of a skin surface after application of a composition disclosed herein. If cellulose derived capsules are too large, its size will reduce or disrupt the formation of an encapsulate layer, thereby reducing the packing of encapsulates which in turn will reduce the efficiency of the UV absorption and exposing the skin layer from harmful UV radiation. In aspects of this embodiment, a cellulose derived capsule has a diameter of, e.g., at least 200 nm, at least 250 nm, at least 300 nm, at least 350 nm, at least 400 nm, at least 450 nm, at least 500 nm, at least 550 nm, at least 600 nm, at least 650 nm, at least 700 nm. In other aspects of this embodiment, a cellulose derived capsule has a diameter of, e.g., at most 200 nm, at most 250 nm, at most 300 nm, at most 350 nm, at most 400 nm, at most 450 nm, at most 500 nm, at most 550 nm, at most 600 nm, at most 650 nm, at most 700 nm.

In aspects of this embodiment, a cellulose derived capsule has a diameter of, e.g., about 200 nm to about 250 nm, about 200 nm to about 300 nm, about 200 nm to about 350 nm, about 200 nm to about 400 nm, about 200 nm to about 450 nm, about 200 nm to about 500 nm, about 200 nm to about 550 nm, about 200 nm to about 600 nm, about 200 nm to about 650 nm, about 200 nm to about 700 nm, about 250 nm to about 300 nm, about 250 nm to about 350 nm, about 250 nm to about 400 nm, about 250 nm to about 450 nm, about 250 nm to about 500 nm, about 250 nm to about 550 nm, about 250 nm to about 600 nm, about 250 nm to about 650 nm, about 250 nm to about 700 nm, about 300 nm to about 350 nm, about 300 nm to about 400 nm, about 300 nm to about 450 nm, about 300 nm to about 500 nm, about 300 nm to about 550 nm, about 300 nm to about 600 nm, about 300 nm to about 650 nm, about 300 nm to about 700 nm, about 350 nm to about 400 nm, about 350 nm to about 450 nm, about 350 nm to about 500 nm, about 350 nm to about 550 nm, about 350 nm to about 600 nm, about 350 nm to about 650 nm, about 350 nm to about 700 nm, about 400 nm to about 450 nm, about 400 nm to about 500 nm, about 400 nm to about 550 nm, about 400 nm to about 600 nm, about 400 nm to about 650 nm, about 400 nm to about 700 nm, about 450 nm to about 500 nm, about 450 nm to about 550 nm, about 450 nm to about 600 nm, about 450 nm to about 650 nm, about 450 nm to about 700 nm, about 500 nm to about 550 nm, about 500 nm to about 600 nm, about 500 nm to about 650 nm, about 500 nm to about 700 nm, about 550 nm to about 600 nm, about 550 nm to about 650 nm, about 550 nm to about 700 nm, about 600 nm to about 650 nm, about 600 nm to about 700 nm or about 650 nm to about 700 nm.

A cellulose derived capsule disclosed herein is designed to not to absorb or otherwise penetrate, or minimize such absorption/penetration, into the epidermal layer of the skin. In an embodiment, cellulose derived capsules disclosed herein are not absorbed or otherwise penetrate through the epidermal layer of the skin. In aspects of this embodiment, cellulose derived capsules disclosed herein are not substantially absorbed or otherwise penetrate through the stratum corneum into the live epidermal layer of the skin. In aspects of this embodiment, only, e.g., at most 1%, at most 5%, at most 10%, at most 15%, at most 20% or at most 25% of cellulose derived capsules disclosed herein are absorbed or otherwise penetrate through the stratum corneum into the live epidermal layer of the skin.

In aspects of this embodiment, cellulose derived capsule disclosed herein may be absorbed or otherwise penetrate the epidermal layer of the skin by only, e.g., about 0.1 µm, about 0.5 µm, about 1 µm, about 5 µm, about 10 µm, about 15 µm, about 20 µm, about 30 µm, about 40 µm, about 50 µm, about 60 µm, about 70 µm, about 80 µm, about 90 µm or about 100 µm. In other aspects of this embodiment, cellulose derived capsules disclosed herein may be absorbed or otherwise penetrate the epidermal layer of the skin by only, e.g., at most about 0.1 µm, at most 0.5 µm, at most 1 µm, at most 5 µm, at most 10 µm, at most 15 µm, at most 20 µm, at most 30 µm, at most 40 µm, at most 50 µm, at most 60 µm, at most 70 µm, at most 80 µm, at most 90 µm or at most 100 µm. In yet other aspects of this embodiment, cellulose derived capsules disclosed herein may be absorbed or otherwise penetrate the epidermal layer of the skin by only, e.g., about 0.1 mm to about 1 µm, about 0.1 mm to about 5 µm, about 0.1 mm to about 10 µm, about 0.1 mm to about 15 µm, about 0.1 mm to about 20 µm, about 0.1 mm to about 25 µm, about 0.1 mm to about 30 µm, about 0.1 mm to about 40 µm, about 0.1 mm to about 50 µm, about 0.1 mm to about 60 µm, about 0.1 mm to about 70 µm, about 0.1 mm to about 80 µm, about 0.1 mm to about 90 µm, about 0.1 mm to about 100 µm, about 0.5 mm to about 1 µm, about 0.5 mm to about 5 µm, about 0.5 mm to about 10 µm, about 0.5 mm to about 15 µm, about 0.5 mm to about 20 µm, about 0.5 mm to about 25 µm, about 0.5 mm to about 30 µm, about 0.5 mm to about 40 µm, about 0.5 mm to about 50 µm, about 0.5 mm to about 60 µm, about 0.5 mm to about 70 µm, about 0.5 mm to about 80 µm, about 0.5 mm to about 90 µm, about 0.5 mm to about 100 µm, about 1 mm to about 5 µm, about 1 mm to about 10 µm, about 1 mm to about 15 µm, about 1 mm to about 20 µm, about 1 mm to about 25 µm, about 1 mm to about 30 µm, about 1 mm to about 40 µm, about 1 mm to about 50 µm, about 1 mm to about 60 µm, about 1 mm to about 70 µm, about 1 mm to about 80 µm, about 1 mm to about 90 µm, about 1 mm to about 100 µm, about 5 mm to about 10 µm, about 5 mm to about 15 µm, about 5 mm to about 20 µm, about 5 mm to about 25 µm, about 5 mm to about 30 µm, about 5 mm to about 40 µm, about 5 mm to about 50 µm, about 5 mm to about 60 µm, about 5 mm to about 70 µm, about 5 mm to about 80 µm, about 5 mm to about 90 µm, about 5 mm to about 100 µm, about 10 mm to about 15 µm, about 10 mm to about 20 µm, about 10 mm to about 25 µm, about 10 mm to about 30 µm, about 10 mm to about 40 µm, about 10 mm to about 50 µm, about 10 mm to about 60 µm, about 10 mm to about 70 µm, about 10 mm to about 80 µm, about 10 mm to about 90 µm or about 10 mm to about 100 µm.

A cellulose derived capsule disclosed herein may be designed to be stable or unstable. Stability includes mechanical stability as well as photostability. Mechanical stability refers to the degree of encapsulate breakage or disintegrate following exposure to physical forces. Photostability refers to the degree of encapsulate breakage or disintegrate following exposure to the sun or UV radiation. Upon breakage of encapsulates their internal contents, including, a sunscreen active agent, a photostabilizing agent and/or an additional agent disclosed herein are released onto a skin surface.

In an embodiment, a cellulose derived capsule disclosed herein is prepared so to experience no or minimal breakage when applied to a skin surface. In another embodiment, a cellulose derived capsule disclosed herein is prepared so to experience various degrees of breakage, on average, when applied to a skin. In an aspect of this embodiment, a cellulose derived capsule is formulated so as to break open in response to conditions that occur on a skin surface, so that after application the cellulose derived capsules act to release their contents in a time-release or controlled manner. For example, skin or hair conditions can vary with the user's environment, a variation which can trigger breakage of cellulose derived capsules, include, without limitation, dryness of the skin surface, dryness of hair, pH, temperature, friction, exposure to light and exposure to air.

In an embodiment, a cellulose derived capsule may be prepared so as to experience about 0% breakage, or breakage in a range of from about 1% to about 100%. In aspects of this embodiment, a cellulose derived capsule may be prepared so as to experience breakage of, e.g., at least 10%, at least 20%, at least 30%, at least 40%, at least 50%, at least 60%, at least 70, at least 80%, at least 90%, or at least 95% after application to a skin surface. In other aspects of this embodiment, a cellulose derived capsule may be prepared so as to experience breakage of, e.g., at most 10%, at most 20%, at most 30%, at most 40%, at most 50%, at most 60%, at most 70, at most 80%, at most 90%, or at most 95% after application to a skin surface. In yet other aspects of this embodiment, a cellulose derived capsule may be prepared so as to experience breakage in a range of, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% after application to a skin surface.

A composition disclosed herein comprises a cellulose derived capsule in an amount sufficient to provide an effective amount of the one or more sunscreen active agent, a photostabilizing agent and/or an additional agent disclosed herein. In aspects of this embodiment, a composition disclosed herein comprises a cellulose derived capsule in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34% or at least 35% of the total weight of the composition.

In other aspects of this embodiment, a composition disclosed herein comprises a cellulose derived capsule in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34% or at most 35% of the total weight of the composition.

In other aspects of this embodiment, a composition disclosed herein comprises a cellulose derived capsule in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises a cellulose derived capsule in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10.0% to about 15%, about 10.0% to about 20%, about 10.0% to about 25%, about 10.0% to about 30%, about 10.0% to about 35%, about 10.0% to about 40%, about 15.0% to about 20%, about 15.0% to about 25%, about 15.0% to about 30%, about 15.0% to about 35%, about 15.0% to about 40%, about 20.0% to about 25%, about 20.0% to about 30%, about 20.0% to about 35%, about 20.0% to about 40%, about 25.0% to about 30%, about 25.0% to about 35%, about 25.0% to about 40%, about 30.0% to about 35%, about 30.0% to about 40% or about 35.0% to about 40% of the total weight of the composition.

A sunscreen composition disclosed herein generally has a pH of about 4 to about 8. In aspects of this embodiment, a sunscreen composition has a pH of, e.g., about 4 to about 5, about 4 to about 6, about 4 to about 7, about 4 to about 8, about 5 to about 6, about 5 to about 7, about 5 to about 8, about 6 to about 7, about 6 to about 8 or about 7 to about 8. In aspects of this embodiment, a sunscreen composition has a pH of, e.g., about 6.4 to about 7.4, about 6.5 to about 7.5, about 6.6 to about 7.6, about 6.7 to about 7.7, about 6.6 to about 7.2, about 6.7 to about 7.3, about 6.8 to about 7.4, about 6.9 to about 7.5, about 7.0 to about 7.6, about 6.7 to about 7.1, about 6.8 to about 7.2, about 6.9 to about 7.3, about 7.0 to about 7.4, about 6.8 to about 7.0, about 6.9 to about 7.1 or about 7.0 to about 7.2.

A composition disclosed herein may be applied topically to a skin surface of an individual. A skin surface includes the skin of the arms, legs and torso and head, including the scalp and hair of an individual.

A composition disclosed herein may be topically applied to an individual by hand or with an applicator. An applicator includes without limitation, with a sponge, a loofah, a toy, a cotton pad, a wash cloth, a specialized wash cloth, a towel, clothing, a spray bottle, an applicator bottle or any device or article, including a clothing article or applicator. A toy, includes, without limitation, a rubber squeeze toy, including, without limitation, a rubber duck, or a plastic squeeze toy. An applicator disclosed herein is preloaded or can be loaded with a composition disclosed herein. An applicator includes an applicator bottle with a roller ball, a push button, a nozzle, a turn nob or other means to apply the sunscreen composition to an individual. Typically, an applicator disclosed herein provides a composition disclosed herein to an individual in metered, defined amounts. For example, metering may be accomplished by pushing down on a nozzle that is part of the applicator. An applicator may also be a squeezable bottle wherein a composition disclosed herein can be dispensed from the bottle as an individual squeezes the bottle. A sunscreen composition disclosed herein may also be applied using a spray on applicator, including, without limitation, a spray bottle.

A composition disclosed herein can be, or combined with, a skin care product. Non-limiting examples of a skin care product include any conventional body wash, after shower body lotion, shampoo, conditioner, soap, gel, hand sanitizer, cream, spray, mouse, lotion, ointment, make-up product, lip balm, hair spray product, arachnid/insect repellent or medicinal product. A body wash, shampoo, after shower body lotion, conditioner, soap, gel, hand sanitizer, cream, spray, mouse, lotion, ointment, make-up product, lip balm, hair spray product, arachnid/insect repellent or medicinal product disclosed herein can be, without limitation, any body wash, after shower body lotion, shampoo, conditioner, soap, gel, hand sanitizer, cream, spray, mouse, lotion, ointment, make-up product, lip balm, hair spray product, arachnid/insect repellent or medicinal product known or apparent to one of skill in the art. A skin care product may be applied by hand, washcloth, or any cleansing article such as a brush, loofah, pouf, sponge, or other to an individual.

A bodywash includes, without limitation, a lathering bodywash or a non-lathering bodywash. A bodywash includes, without limitation, an emulsion of water and detergent base with added fragrance and is a skin cleaning agent commonly used in a shower or bath. A bodywash may also contain one or more surfactants. Popular brands such as Fa, Palmolive, Axe, Lynx, Radox, Nivea, Johnson, Senses, Adidas, Umbro, Old Spice, Imperial Leather and right guard. A bodywash also includes, without limitation an all-in-one multifunctional, moisturizing cleanser that both provides SPF and imparts color to the skin after application, wherein the bodywash includes, without limitation, iron oxide pigments as well as red petrolatum, at least one, preferably two, anionic lathering surfactants, a non-ionic lathering surfactant, surface-treated zinc oxide pigments, an alkyl silicone and a volatile cyclic silicone.

A spray includes, without limitation, an aerosol spray that includes a propellant. A propellant includes, without limitation is a mixture of isobutane, butane and propane, including, without limitation A46, AP30 (11% propane, 29% isobutane, 60% n-butane); AP40 (22% propane, 24% isobutane, 54% n-butane); and AP70 (31% propane, 23% isobutane, 46% n-butane). A spray includes, without limitation, hair spray, body spray, for example, without limitation, those sold by AXE, spray on insect protection and spray on deodorant.

A shampoo includes, without limitation, sodium lauryl sulfate and/or sodium laureth sulfate with a co-surfactant, including, without limitation, cocamidopropyl betaine in water to form a thick, viscous liquid. A shampoo includes salt, including, without limitation, sodium chloride, a preservative and a fragrance. In an embodiment, a shampoo is formulated to maximize the following qualities, without limitation, pleasing foam, easy rinsing, minimal skin or eye irritation, feels thick and/or creamy, pleasant fragrance, low toxicity, good biodegradability, slightly acidic and no or minimal damage to hair.

A lotion includes, without limitation, a low to low medium viscosity topical preparation intended for application to unbroken skin. A lotion is an oil-in-water emulsion that includes, without limitation, cetearyl alcohol and an emulgent to prevent separation of these two phases. A lotion contains, without limitation, fragrances, glycerol, petroleum jelly, dyes, preservatives, proteins and stabilizing agents. A lotion includes, without limitation a skin medication such as an antibiotic, antiseptic, antifungal, corticosteroid, anti-acne agents or soothing, smoothing, moisturizing or protective agents, including, without limitation, calamine. A gel includes, without limitation, a solid, jelly-like material that can have properties ranging from soft and weak to hard and tough and include, without limitation, substantially dilute cross-linked system, which exhibit no flow when in a steady-state. In an embodiment a gel includes, without limitation, a hydrogel, an organogel or a xerogel.

A conditioner includes, without limitation, hair conditioner, which can include, without limitation, the following ingredients: moisturizers, reconstructors, acidifiers, detanglers, thermal protectors, glossers, oils, surfactants, lubricants, sequestrants, antistatic agents, preservatives and sunscreen active agents. A conditioner includes, without limitation, a pack conditioner, a leave-in conditioner, an ordinary conditioner that includes both pack and leave-in ones and hold conditioners.

A hand sanitizer includes, without limitation, isopropanol, ethanol, n-propanol or povidone-iodine. In a further embodiment, hand sanitizers can contain the following inactive ingredients, without limitation, a thickening agent, including without limitation, polyacrylic acid for alcohol gels, humectants, including without limitation, glycerin for liquid rubs, propylene glycol and essential oils derived from plants. A hand sanitizer is a non-alcohol hand sanitizer, which includes without limitation, a nitrogenous cationic surface-acting agent that includes, without limitation, benzalkonium chloride, triclosan or povidone-iodine.

A soap is a salt of a fatty acid. Soaps for cleansing are generally obtained by treating vegetable or animal oils and fats with a strongly alkaline solution. Soaps can be in a solid form, such as a bar or in a decorative shape. Soap can also be a liquid. Other components can be added to soap, without limitation, including oils, fragrances and conditioners. In a further embodiment, a soap contains a surfactant. In another embodiment, a soap does not contain a surfactant.

In an embodiment, a soap is a melt and pour soap. The process for a melt and pour soap differs from the cold process, hot process or rebatching process of making soap in that no soap is made (i.e. no actual saponification occurs) in the process; a melt and pour soap base acquired in commerce is melted in a direct heat melter or water jacket melting pot (large double boiler) and additional items such as fragrance, essential oils, moisturizing agents, colorants, or exfoliating agents are added. While still hot, the concoction can be poured into individual molds, tray molds, or blocks which upon cooling can be sliced. A melt and pour soap includes, without limitation, a clear glycerin soap or a white soap made from white coconut oil.

In an embodiment, a soap is Castile soap. Castile soap is a name used in English-speaking countries for olive oil based soap made in a style similar to that originating in the Castile region of Spain. In an embodiment, Castile soap includes, without limitation, sodium hydroxide, potassium hydroxide and/or ash.

In one embodiment, a sunscreen composition disclosed herein is use in combination as an admixture with a skin care product disclosed herein. A composition disclosed herein when combined as an admixture with a skin care product in an amount sufficient to allow the one or more sunscreen active agents, cationic polymers, film formers, photostabilizing agents, surfactant metal complexes, and additional agents to function properly. In aspects of this embodiment, a composition disclosed herein is combined with a skin care product in a ratio of, e.g., about 1.0 part composition to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 parts skin care product as measured w/w.

In other aspects of this embodiment, a composition disclosed herein is combined with a skin care product in a ratio range of, e.g., about 1.0 part composition to about 0.1 to about 1.0 part skin care product as measured w/w, about 1.0 part composition to about 0.1 to about 5.0 parts skin care product as measured w/w, about 1.0 part composition to about 0.1 to about 10 parts skin care product as measured w/w, about 1.0 part composition to about 0.1 to about 15 parts skin care product as measured w/w, about 1.0 part composition to about 0.1 to about 20 parts skin care product as measured w/w, about 1.0 part composition to about 0.5 to about 1.0 part skin care product as measured w/w, about 1.0 part composition to about 0.5 to about 5.0 parts skin care product as measured w/w, about 1.0 part composition to about 0.5 to about 10 parts skin care product as measured w/w, about 1.0 part composition to about 0.5 to about 15 parts skin care product as measured w/w, about 1.0 part composition to about 0.5 to about 20 parts skin care product as measured w/w, about 1.0 part composition to about 1.0 to about 5.0 parts skin care product as measured w/w, about 1.0 part composition to about 1.0 to about 10 parts skin care product as measured w/w, about 1.0 part composition to about 1.0 to about 15 parts skin care product as measured w/w, about 1.0 part composition to about 1.0 to about 20 parts skin care product as measured w/w, about 1.0 part composition to about 5.0 to about 25 parts skin care product as measured w/w, about 1.0 part composition to about 1.0 to about 30 parts skin care product as measured w/w, about 1.0 part composition to about 1.0 to about 35 parts skin care product as measured w/w, about 1.0 part composition to about 1.0 to about 40 parts skin care product as measured w/w, about 1.0 part composition to about 1.0 to about 45 parts skin care product as measured w/w, about 1.0 part composition to about 1.0 to about 50 parts skin care product as measured w/w, about 1.0 part composition to about 1.0 to about 1.0 part composition to about 5.0 to about 10 parts skin care product as measured w/w, about 1.0 part composition to about 5.0 to about 15 parts skin care product as measured w/w, about 1.0 part composition to about 5.0 to about 20 parts skin care product as measured w/w, about 1.0 part composition to about 5.0 to about 25 parts skin care product as measured w/w, about 1.0 part composition to about 5.0 to about 30 parts skin care product as measured w/w, about 1.0 part composition to about 5.0 to about 35 parts skin care product as measured w/w, about 1.0 part composition to about 5.0 to about 40 parts skin care product as measured w/w, about 1.0 part composition to about 5.0 to about 45 parts skin care product as measured w/w or about 1.0 part composition to about 5.0 to about 50 parts skin care product as measured w/w.

In an embodiment, a sunscreen composition is combined with a skin care product all at once, in groups, or separately. In an embodiment, a sunscreen composition comprises at least two separate components that include, without limitation, a first component that comprises all the ingredients except an inorganic or physical blocker sunscreen active agent, and a second component that comprises an inorganic or physical blocker sunscreen active agent. In an embodiment, a first component is added to a skin care product with thorough mixing, followed by a second component. In a further embodiment, all ingredients except a metal oxide are mixed, then added to skin care product, and then the metal oxide is added.

In an embodiment, a composition disclosed herein is formulated as a skin care product. In aspects of this embodiment, a composition disclosed herein is formulated as a body wash, after shower body lotion, shampoo, conditioner, soap, gel, hand sanitizer, cream, spray, mouse, lotion, ointment, make-up product, lip balm, hair spray product, arachnid/insect repellent or medicinal product disclosed herein. Besides the one or more sunscreen active agents, cationic polymers, film formers, photostabilizing agents, surfactant metal complexes, and additional agents disclosed herein, such skin care products include additional ingredients necessary to formulate the skin care product.

A composition disclosed herein formulated as a skin care product disclosed herein typically requires the use of one or more surfactants. A surfactant may be cationic, anionic, non-ionic, zwitterionic, amphoteric, or any combination thereof. In a further embodiment, surfactants include, without limitation, alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention. In a further embodiment, alkyl sulfates include, without limitation, sodium, ammonium, potassium, magnesium, or TEA salts of lauryl or myristyl sulfate or ammonium, sodium, magnesium, or TEA laureth-3 sulfate.

A composition disclosed herein comprises a surfactant in an amount sufficient to promote or facilitate the function or activity of that surfactant. In aspects of this embodiment, a composition disclosed herein comprises a surfactant in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a surfactant in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a surfactant in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In an embodiment, a surfactant is an environmentally favourable surfactant including, without limitation, dodecyl glucosides.

In an embodiment, a surfactant is a lathering surfactant. A lathering surfactant has a log P of less than about 2.5 that produces foam when mixed with and agitated in water. An anionic lathering surfactant is a sulfate, wherein the sulfate is, without limitation, an alkyl sulfate or an alkyl ether sulfate. A sulfate includes, without limitation, sodium laureth sulfate and ammonium laureth sulfate. Sodium laureth sulfate has a molecular formula $CH_3(CH_2)_{10}CH_2(OCH_2CH_2)_{20}SO_3Na$ and conforms to the following structure:

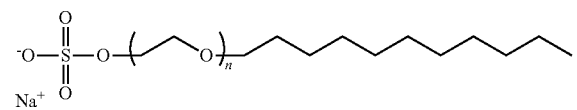

In an embodiment, a sunscreen composition or a skin care product combined with a sunscreen composition, includes, without limitation, sodium laureth sulfate at a concentration of from about 10% to about 15% or from about 7.5% to about 8.5%. In a further embodiment, ammonium laureth sulfate is used in combination with an alkyl glucoside, wherein the alkyl glucoside includes, without limitation, decyl glucoside. The combination of ammonium laureth sulfate and decyl glucoside is sold under the tradename Plantaren PS-100 by Cognis. In an embodiment, ammonium laureth sulfate in combination with decyl glucoside is present in a sunscreen composition or body wash, after shower body lotion, shampoo, conditioner, soap, gel, hand sanitizer, cream, spray, mouse, lotion, ointment, make-up product, lip balm, hair spray product, arachnid/insect repellent or medicinal product combined with a sunscreen composition at a concentration of from about 5% to about 10%, or from about 7.5% to about 8.5%.

In a further embodiment, a lathering surfactant includes one, two, three or more anionic lathering surfactants, including, without limitation, sulfates, including, without limitation, sodium laureth sulfate and ammonium laureth sulfate. In an embodiment, sodium laureth sulfate and ammonium laureth sulfate are combined with decyl glucoside. In an additional embodiment, the two sulfates are present at a combined concentration of from about 15% to about 25%.

In an embodiment, a sunscreen composition disclosed herein includes, without limitation, at least one cationic surfactant. In an embodiment, cationic surfactants include, without limitation, fatty amines, di-fatty quaternary amines, tri-fatty quaternary amines, imidazolinium quaternary amines, and combinations thereof. In a further embodiment, fatty amines include, without limitation, monalkyl quaternary amines such as cetyltrimethylammonium bromide. In an embodiment, quaternary amine include, without limitation, dialklamidoethyl hydroxyethylmonium methosulfate, In an embodiment, a sunscreen composition disclosed herein includes, without limitation, stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride; and stearalkonium chloride. Additional cationic surfactants are disclosed in U.S. Pat. No. 4,303,543 see column 4, lines 58 and column 5, lines 1 42, incorporated herein by references. Also see CTFA Cosmetic Ingredient Dictionary, 4th Edition 1991, pages 509 514 for various long chain alkyl cationic surfactants; incorporated herein by reference.

In a further embodiment, anionic surfactants, include, without limitation, sulfated monoglycerides of the form $R^1CO$—O—$CH_2$—C(OH)H—$CH_2$—O—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine, monoethanolamine and sodium cocomonoglyceride sulfate. In a further embodiment, anionic surfactants include, without limitation, olefin sulfonates of the form $R^1SO_3M$, wherein R1 is a mono-olefin having from about 12 to about 24 carbon atoms, and M is a water-soluble cation such as ammonium, sodium, potassium, magnesium, triethanolamine, diethanolamine and monoethanolamine. In an embodiment, a sulfonated olefin is sodium C14/C16 alpha olefin sulfonate. In a further embodiment, anionic surfactants, include, without limitation, linear alkylbenzene sulfonates of the form $R^1$—$C_6H_4$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine monoethanolamine and sodium dodecylbenzene sulfonate. In an additional embodiment, anionic surfactants include, without limitation, primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. In a further embodiment, alkane sulfonate include, without limitation, alkali metal or ammonium $C_{13-17}$ paraffin sulfonates. In an additional embodiment, anionic surfactants include, without limitation, alkyl sulfosuccinates, which include disodium N-octadecylsulfosuccinamate, diammonium lauryl sulfosuccinate, disodium laureth sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid and dioctyl esters of sodium sulfosuccinic acid; sodium dodecyl sulfate (or sodium lauryl sulfate), sodium laureth sulfate and ammonium lauryl sulfate.

Acyl taurate surfactants include, without limitation, taurine, N-alkyltaurines such as the one prepared by reacting dodecylamine with sodium isethionate as detailed in U.S. Pat. No. 2,658,072, and coconut fatty acid salts, such as, e.g., sodium methyl cocoyl taurate and sodium methyl oleoyl taurate.

In a further embodiment, anionic surfactants include, without limitation, acyl isethionates, including, without limitation, acyl isethionates include ammonium cocoyl isethionate, sodium cocoyl isethionate, sodium lauroyl isethionate, alkylglyceryl ether sulfonates of the form $R^1$—$OCH_2$—C(OH)H—$CH_2$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine, sodium cocoglyceryl ether sulfonate, sulfonated fatty acids of the form $R^1$—CH($SO_4$)—COOH and sulfonated methyl esters of the from $R^1$—CH($SO_4$)—CO—O—$CH_3$, where $R^1$ is a saturated or unsaturated, branched or unbranched alkyl group from about 8 to about 24 carbon atoms (e.g., alpha sulphonated coconut fatty acid and lauryl methyl ester); phosphates such as monoalkyl, dialkyl, and trialkylphosphate salts formed by the reaction of phosphorous pentoxide with monohydric branched or unbranched alcohols having from about 8 to about 24 carbon atoms (e.g., sodium mono or dilaurylphosphate, ethoxylated monoalkyl phosphates, etc.); acyl glutamates corresponding to the formula $R^1CO$—N(COOH)—$CH_2CH_2$—$CO_2M$ wherein $R^1$ is a saturated or unsaturated, branched or unbranched alkyl or alkenyl group of about 8 to about 24 carbon atoms, and M is a water-soluble cation (e.g., sodium lauroyl glutamate and sodium cocoyl glutamate); alkanoyl sarcosinates corresponding to the formula $R^1CON(CH_3)$—$CH_2CH_2$—$CO_2M$ wherein $R^1$ is a saturated or unsaturated, branched or unbranched alkyl or alkenyl group of about 10 to about 20 carbon atoms, and M is a water-soluble cation (e.g., sodium lauroyl sarcosinate, lauroyl sarcosine, sodium cocoyl sarcosinate, and ammonium lauroyl sarcosinate); alkyl ether carboxylates corresponding to the formula $R^1$—($OCH_2CH_2$)x-$OCH_2$—$CO_2M$ wherein $R^1$ is a saturated or unsaturated, branched or unbranched alkyl or alkenyl group of about 8 to about 24 carbon atoms, x is 1 to 10, and M is a water-soluble cation (e.g., sodium laureth carboxylate); acyl lactylates corresponding to the formula $R^1CO$—[O—$CH(CH_3)$—CO]x—$CO_2M$ wherein $R^1$ is a saturated or unsaturated, branched or unbranched alkyl or alkenyl group of about 8 to about 24 carbon atoms, x is 3, and M is a water-soluble cation (e.g., sodium cocoyl lactylate); carboxylates, nonlimiting examples of which include sodium lauroyl carboxylate, sodium cocoyl carboxylate, and ammonium lauroyl carboxylate; anionic flourosurfactants; and natural soaps derived from the saponification of vegetable and/or animal fats & oils examples of which include sodium laurate, sodium myristate, palmitate, stearate and tallowate, cocoate. In a further embodiment, a soap is a semi-solid. In another embodiment, a soap includes a wax to form a solid soap bar.

In an embodiment a counter cation, M, is used on the anionic surfactant. In a further embodiment, a counter cation includes, without limitation, sodium, potassium, ammonium, monoethanolamine, diethanolamine, and triethanolamine.

In an embodiment, non-ionic surfactants include, without limitation, alkyl glucosides, alkyl polyglucosides, polyhydroxy fatty acid amides, alkoxylated fatty acid esters, sucrose esters, amine oxides, and mixtures thereof. Alkyl glucosides and alkyl polyglucosides are condensation products of long chain alcohols, including, without limitation, $C_{8-30}$ alcohols, with sugars or starches or sugar or starch polymers, including, without limitation, glycosides or polyglycosides and are represented by the formula $(S)_n$—O—R wherein S is a sugar moiety such as glucose, fructose, mannose, and galactose; n is an integer of from about 1 to about 1000, and R is a $C_{8-30}$ alkyl group. In an embodiment, long chain alcohols from which the alkyl group can be derived include, without limitation, decyl alcohol, cetyl alcohol, stearyl alcohol, lauryl alcohol, myristyl alcohol, oleyl alcohol, and more. In a further embodiment, these surfactants include, without limitation, those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). In an additional embodiment, sucrose ester surfactants include, without limitation, sucrose cocoate and sucrose laurate.

In another embodiment, non-ionic surfactants include, without limitation, polyhydroxy fatty acid amide surfactants, more specific examples of which include glucosamides. In an embodiment a process for making compositions containing polyhydroxy fatty acid amides are disclosed, for example, in G.B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934. In an embodiment, non-ionic surfactants include, without limitation, amine oxides, including, without limitation, those corresponding to the general formula $R_1R_2$, $R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. In an embodiment, amine oxides include, without limitation, dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

The term "amphoteric surfactant," as used herein, is also intended to encompass zwitterionic surfactants, which are well known to formulators skilled in the art as a subset of amphoteric surfactants. Amphoteric lathering surfactants include, without limitation, derivatives of aliphatic secondary and tertiary amines, including, without limitation, those wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate. In an embodiment, amphoteric or zwitterionic surfactants include, without limitation, betaines, sultaines, hydroxysultaines, alkyliminoacetates, iminodialkanoates, aminoalkanoates, and mixtures thereof. In an embodiment, betaines include, without limitation, the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel). In a further embodiment, sultaines and hydroxysultaines include, without limitation, materials such as cocamidopropyl hydroxysultaine (available as Miraataine CBS from Rhone-Poulenc).

In an embodiment, amphoteric surfactants include, without limitation, the following compounds: Cetyl dimethyl betaine (this material also has the CTFA designation cetyl betaine); Cocamidopropylbetaine; Cocamidopropyl hydroxy sultaine. Examples of other useful amphoteric surfactants are alkyliminoacetates, and iminodialkanoates and aminoalkanoates of the formulas $RN[(CH_2)—CO_2\text{-}M]_2$ and $RNH(CH_2)_mCO_2$ M wherein m is from 1 to 4, R is a $C_8$-$C_{22}$ alkyl or alkenyl, and M is H, alkali metal, alkaline earth metal ammonium, alkanolammonium or imidazolinium and ammonium derivatives. In a further embodiment, amphoteric surfactants include, without limitation, sodium 3-dodecyl-aminopropionate, sodium 3-dodecylaminopropane sulfonate. In a further embodiment, N-higher alkyl aspartic acids include, without limitation, those produced according to the teaching of U.S. Pat. No. 2,438,091; and the products sold under the trade name "Miranol" and described in U.S. Pat. No. 2,528,378. In a further embodiment, amphoterics include, without limitation, amphoteric phosphates, such as coamidopropyl PG-dimonium chloride phosphate (commercially available as Monaquat PTC, from Mona Corp.). In another embodiment, amphoacetates include, without limitation, disodium lauroamphodiacetate, sodium lauroamphoacetate, and mixtures thereof.

In an embodiment, a bodywash is, without limitation, SUAVE Body Wash, which has the following ingredients: Water, Ammonium Lauryl Sulfate, Ammonium Laureth Sulfate, Cocamidopropyl Betaine, Fragrance, Glycerin, Hydrolyzed Milk Protein & Honey Extract, PEG-10 Sunflower Glycerides, Cocamide MEA, Guar Hydroxypropylrimonium Chloride, Acrylates Copolymer, PEG-5 Cocamide, Helianthus Annuus (Sunflower) Seed Oil or Glycine Soja (Soybean) Oil, Tetrasoidum EDTA, Propylene Glycol, Ammonium Chloride, Sodium Hydroxide, Methylchloroisothiazolinone, Methylisothiazolinone, Titanium Dioxide (CI 77891).

In an embodiment, soapless cleansers are used in addition to, or instead of, soaps/surfactants, including, without limitation OILATUM™ AD (registered trademark, Stiefel Laboratories) AQUANIL™ (registered trademark, Person & Covey, Inc.), CETAPHIL™ (trademark, Galderma Laboratories, Inc.) or SPECTRODERM™ (registered trademark, Draxis Pharmaceutical Inc.), or their equivalents, may be utilized as a soapless component in the present invention.

In an embodiment, the sunscreen composition containing a sunscreen active agent is a powder or other dry form. In a further embodiment, the sunscreen composition containing a sunscreen active agent is applied to an individual by applying the powder or other dry form to the individual. In a further embodiment, following application of the powder or other dry form, the sunscreen composition containing a sunscreen active agent is rubbed, massaged, caressed onto the individual. In an embodiment, the sunscreen composition containing a sunscreen active agent that is in the form of a powder or other dry form is stored in an applicator. In an embodiment, the applicator is the same as the applicator used for powder or other dry form products, including, without limitation, a baby powder bottle or other applicator that is conformed to the application of a powder or other dry form of a sunscreen composition.

In an embodiment, the components comprising a sunscreen composition are mixed in, without limitation, water or oil. In an embodiment, a sunscreen composition or sunscreen composition combined with a body wash, after shower body lotion, shampoo, conditioner, soap, gel, hand sanitizer, cream, spray, mouse, lotion, ointment, make-up product, lip balm, hair spray product, arachnid/insect repellent or medicinal product includes, without limitation, one or more surfactants. The use of surfactants in bodywashes is well-known in the art. Any surfactant known in the art and appropriate for a body wash, after shower body lotion, shampoo, conditioner, soap, gel, hand sanitizer, cream, spray, mouse, lotion, ointment, make-up product, lip balm, hair spray product, arachnid/insect repellent or medicinal product may be used. See, McCutcheon's Detergents & Emulsifiers, M.C. Publishing Co. (North American edition 1989); Schwartz, et al., Surface Active Agents, Their Chemistry and Technology, New York, Interscience Publishers, 1949, and U.S. Pat. Nos. 6,096,697; 4,741,855; 4,788,066; 5,104,646; 5,106,609; 2,658,072; 2,438,091; 2,528,378; 2,486,921; 2,486,922; 2,396,278; 2,979,465; 3,179,599; 5,322,643; 5,084,212; 3,332,880; 4,122,029; 4,265,878; 4,421,769; 3,929,678; 3,959,461; 4,387,090; 4,303,543; and 6,224,852; and in British Patent Nos. 848,224 and 791,415. Also see CTFA Cosmetic Ingredient Dictionary, 4th Edition 1991, pages 509 514 for various long chain alkyl cationic surfactants; and Richmond, James M., Cationic Surfactants, Marcel Dekker, Inc., New York and Basel, 1990.

In an embodiment, a composition disclosed herein is a sunscreen body wash composition. In aspects of this embodiment, a sunscreen body wash composition disclosed herein comprises about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.1% to about 10% of a polyquaternium, and about 3% to about 17% one or more surfactants. In other aspects of this embodiment, a sunscreen body wash composition disclosed herein comprises about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 0.2% to about 8% of a polyquaternium, and about 5% to about 15% one or more surfactants. In yet other aspects of this embodiment, a sunscreen body wash composition disclosed herein comprises about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 0.4% to about 6% of a polyquaternium, and about 7% to about 13% one or more surfactants. In still other aspects of this embodiment, a sunscreen body wash composition disclosed herein comprises about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 0.6% to about 5% of a polyquaternium, and about 9% to about 11% one or more surfactants. In other aspects of this embodiment, a sunscreen body wash composition disclosed herein comprises about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 2.5% of a polyquaternium, and about 10% one or more surfactants.

In aspects of this embodiment, a sunscreen body wash composition disclosed herein comprises about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.1% to about 10% of a polyquaternium, about 0.5% to about 15% one or more anionic surfactants, and about 0.1% to about 9% one or more amphoteric surfactants. In other aspects of this embodiment, a sunscreen body wash composition disclosed herein comprises about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 0.2% to about 8% of a polyquaternium, about 2% to about 12% one or more anionic surfactants, and about 0.25% to about 7% one or more amphoteric surfactants. In yet other aspects of this embodiment, a sunscreen body wash composition disclosed herein comprises about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 0.4% to about 6% of a polyquaternium, about 4% to about 10% one or more anionic surfactants, and about 0.5% to about 5% one or more amphoteric surfactants. In still other aspects of this embodiment, a sunscreen body wash composition disclosed herein comprises about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 0.6% to about 5% of a polyquaternium, about 6% to about 8% one or more anionic surfactants, and about 2% to about 4% one or more amphoteric surfactants. In other aspects of this embodiment, a sunscreen body wash composition disclosed herein comprises about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 2.5% of a polyquaternium, about 7% one or more anionic surfactants, and about 3% one or more amphoteric surfactants.

In aspects of this embodiment, a sunscreen body wash composition disclosed herein comprises about 5% to about 17% of a cellulose encapsulate comprising about 50% to about 80% of an octocrylene and about 20% to about 50% of a dibenzoylmethane, about 2% to about 14% of a cellulose encapsulate comprising a cinnamate derivative, about 0.1% to about 10% of a polyquaternium, about 0.5% to about 15% one or more sulfate surfactants, and about 0.1% to about 9% one or more betaine surfactants. In other aspects of this embodiment, a sunscreen body wash composition disclosed herein comprises about 7% to about 15% of a cellulose encapsulate comprising about 55% to about 75% of an octocrylene and about 25% to about 45% of a dibenzoylmethane, about 4% to about 12% of a cellulose encapsulate comprising a cinnamate derivative, about 0.2% to about 8% of a polyquaternium, about 2% to about 12% one or more sulfate surfactants, and about 0.25% to about 7% one or more betaine surfactants. In yet other aspects of this embodiment, a sunscreen body wash composition disclosed herein comprises about 8% to about 14% of a cellulose encapsulate comprising about 60% to about 70% of an octocrylene and about 30% to about 40% of a dibenzoylmethane, about 5% to about 11% of a cellulose encapsulate comprising a cinnamate derivative, about 0.4% to about 6% of a polyquaternium, about 4% to about 10% one or more sulfate surfactants, and about 0.5% to about 5% one or more betaine surfactants. In still other aspects of this embodiment, a sunscreen body wash composition disclosed herein comprises about 10% to about 12% of a cellulose encapsulate comprising about 63% to about 68% of an octocrylene and about 33% to about 37% of a dibenzoylmethane, about 7% to about 9% of a cellulose encapsulate comprising a cinnamate derivative, about 0.6% to about 5% of a polyquaternium, about 6% to about 8% one or more sulfate surfactants, and about 2% to about 4% one or more betaine surfactants. In other aspects of this embodiment, a sunscreen body wash composition disclosed herein comprises about 11% of a cellulose encapsulate comprising about 65% of an octocrylene and about 35% of a dibenzoylmethane, about 8% of a cellulose encapsulate comprising a cinnamate derivative, about 2.5% of a polyquaternium, about 7% one or more sulfate surfactants, and about 3% one or more betaine surfactants.

In aspects of this embodiment, a sunscreen body wash composition disclosed herein comprises about 5% to about 17% of a cellulose encapsulate comprising about 50% to about 80% of an octocrylene and about 20% to about 50% of avobenzone, about 2% to about 14% of a cellulose encapsulate comprising octinoxate, about 0.1% to about 10% of a polyquaternium 10, about 0.1% to about 10% sodium laureth sulfate, about 0.1% to about 10% sodium lauryl sulfate and about 0.1% to about 9% cocamido propylbetaine. In other aspects of this embodiment, a sunscreen body wash composition disclosed herein comprises about 7% to about 15% of a cellulose encapsulate comprising about 55% to about 75% of an octocrylene and about 25% to about 45% of avobenzone, about 4% to about 12% of a cellulose encapsulate comprising octinoxate, about 0.2% to about 8% of a polyquaternium 10, about 0.25% to about 7.5% sodium laureth sulfate, about 0.25% to about 7.5% sodium lauryl sulfate and about 0.25% to about 7% cocamido propylbetaine. In yet other aspects of this embodiment, a sunscreen body wash composition disclosed herein comprises about 8% to about 14% of a cellulose encapsulate comprising about 60% to about 70% of an octocrylene and about 30% to about 40% of avobenzone, about 5% to about 11% of a cellulose encapsulate comprising octinoxate, about 0.4% to about 6% of a polyquaternium 10, about 0.5% to about 6.5% sodium laureth sulfate, about 0.5% to about 6.5% sodium lauryl sulfate and about 0.5% to about 5% cocamido propylbetaine. In still other aspects of this embodiment, a sunscreen body wash composition disclosed herein comprises about 10% to about 12% of a cellulose encapsulate comprising about 63% to about 68% of an octocrylene and about 33% to about 37% of avobenzone, about 7% to about 9% of a cellulose encapsulate comprising octinoxate, about 0.6% to about 5% of a polyquaternium 10, about 2.5% to about 4.5% sodium laureth sulfate, about 2.5% to about 4.5% sodium lauryl sulfate and about 2% to about 4% cocamido propylbetaine. In other aspects of this embodiment, a sunscreen body wash composition disclosed herein comprises about 11% of a cellulose encapsulate comprising about 65% of an octocrylene and about 35% of avobenzone, about 8% of a cellulose encapsulate comprising octinoxate, about 2.5% of a polyquaternium, 10, about 3.5% sodium laureth sulfate, about 3.5% sodium lauryl sulfate and about 3% cocamido propylbetaine.

In another embodiment, a sunscreen body wash composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen body wash composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen body wash composition disclosed herein comprises about 1% to about 12%, about 2% to about 10%, about 3% to about 9%, about 5% to about 7% or about 6% of a photostabilizing agent with a concomitant reduction in the amount of a broad spectrum UVA/UVB sunscreen active agent of equal value. In other aspects of this embodiment, the sunscreen body wash composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen body wash composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen body wash composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen body wash composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen body wash composition disclosed herein further comprises a film former. In aspects of this embodiment, the sunscreen body wash composition disclosed herein comprises about 1% to about 6%, about 1.5% to about 4.5%, about 2% to about 4%, about 2.5% to about 3.5% or about 3% of a film former. In other aspects of this embodiment, the sunscreen body wash composition disclosed herein comprises an acrylate copolymer as a film former. In yet other aspects of this embodiment, the sunscreen body wash composition disclosed herein an acrylate copolymer is DERMACRYL® AQF.

In another embodiment, a sunscreen body wash composition disclosed herein further comprises a film former as well as a cellulose encapsulate comprising a broad spectrum UVA/UVB sunscreen active agent and a UVA sunscreen active agent and further comprises a photostabilizing agent. In aspects of this embodiment, the sunscreen body wash composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In other aspects of this embodiment, the sunscreen body wash composition disclosed herein comprises trimethoxy benylidene pentanedione as a photostabilizing agent. In aspects of this embodiment, the sunscreen body wash composition disclosed herein comprises about 1% to about 6%, about 1.5% to about 4.5%, about 2% to about 4%, about 2.5% to about 3.5% or about 3% of a film former. In other aspects of this embodiment, the sunscreen body wash composition disclosed herein comprises an acrylate copolymer as a film former. In yet other aspects of this embodiment, the sunscreen body wash composition disclosed herein an acrylate copolymer is DERMACRYL® AQF.

In another embodiment, a sunscreen body wash composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen body wash composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen body wash composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR3535, lemon eucalyptus oil, eucalyptus oil, peppermint oil, geranium oil and clove oil.

In an embodiment, a composition disclosed herein is a sunscreen body wash composition. In aspects of this embodiment, a sunscreen body wash composition disclosed herein comprises about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.1% to about 10% of a polyquaternium, and about 2% to about 18% one or more surfactants. In other aspects of this embodiment, a sunscreen body wash composition disclosed herein comprises about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 0.2% to about 8% of a polyquaternium, and about 3% to about 15% one or more surfactants. In yet other aspects of this embodiment, a sunscreen body wash composition disclosed herein comprises about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 0.4% to about 6% of a polyquaternium, and about 4% to about 13% one or more surfactants. In still other aspects of this embodiment, a sunscreen body wash composition disclosed herein comprises about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 0.6% to about 5% of a polyquaternium, and about 5% to about 12% one or more surfactants. In other aspects of this embodiment, a sunscreen body wash composition disclosed herein comprises about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 2.5% of a polyquaternium, and about 6% to about 11% one or more surfactants.

In aspects of this embodiment, a sunscreen body wash composition disclosed herein comprises about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.1% to about 10% of a polyquaternium, about 0.5% to about 15% one or more anionic surfactants, about 0.1% to about 5% one or more amphoteric surfactants and about 0.1% to about 5% one or more acyl taurate surfactants. In other aspects of this embodiment, a sunscreen body wash composition disclosed herein comprises about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 0.2% to about 8% of a polyquaternium, about 1% to about 10% one or more anionic surfactants, about 0.25% to about 4% one or more amphoteric surfactants and about 0.25% to about 4% one or more acyl taurate surfactants. In yet other aspects of this embodiment, a sunscreen body wash composition disclosed herein comprises about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 0.4% to about 6% of a polyquaternium, about 2% to about 9% one or more anionic surfactants, about 0.5% to about 3% one or more amphoteric surfactants and about 0.5% to about 3% one or more acyl taurate surfactants. In still other aspects of this embodiment, a sunscreen body wash composition disclosed herein comprises about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 0.6% to about 5% of a polyquaternium, about 3% to about 8% one or more anionic surfactants, about 0.75% to about 2.5% one or more amphoteric surfactants and about 0.75% to about 2.5% one or more acyl taurate surfactants. In other aspects of this embodiment, a sunscreen body wash composition disclosed herein comprises about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 2.5% of a polyquaternium, about 4% to about 7% one or more anionic surfactants, about 1% to about 2% one or more amphoteric surfactants and about 1% to about 2% one or more acyl taurate surfactants.

In aspects of this embodiment, a sunscreen body wash composition disclosed herein comprises about 5% to about 17% of a cellulose encapsulate comprising about 50% to about 80% of an octocrylene and about 20% to about 50% of a dibenzoylmethane, about 2% to about 14% of a cellulose encapsulate comprising a cinnamate derivative, about 0.1% to about 10% of a polyquaternium, about 0.5% to about 8% one or more alkyl sulfosuccinate surfactants, about 0.1% to about 5% one or more acyl isethionate surfactants, about 0.1% to about 5% one or more betaine surfactants and about 0.1% to about 5% one or more acyl taurate surfactants. In other aspects of this embodiment, a sunscreen body wash composition disclosed herein comprises about 7% to about 15% of a cellulose encapsulate comprising about 55% to about 75% of an octocrylene and about 25% to about 45% of a dibenzoylmethane, about 4% to about 12% of a cellulose encapsulate comprising a cinnamate derivative, about 0.2% to about 8% of a polyquaternium, about 1% to about 7% one or more alkyl sulfosuccinate surfactants, about 0.25% to about 4% one or more acyl isethionate surfactants, about 0.25% to about 4% one or more betaine surfactants and about 0.25% to about 4% one or more acyl taurate surfactants. In yet other aspects of this embodiment, a sunscreen body wash composition disclosed herein comprises about 8% to about 14% of a cellulose encapsulate comprising about 60% to about 70% of an octocrylene and about 30% to about 40% of a dibenzoylmethane, about 5% to about 11% of a cellulose encapsulate comprising a cinnamate derivative, about 0.4% to about 6% of a polyquaternium, about 2% to about 6% one or more alkyl sulfosuccinate surfactants, about 0.5% to about 3% one or more acyl isethionate surfactants, about 0.5% to about 3% one or more betaine surfactants and about 0.5% to about 3% one or more acyl taurate surfactants. In still other aspects of this embodiment, a sunscreen body wash composition disclosed herein comprises about 10% to about 12% of a cellulose encapsulate comprising about 63% to about 68% of an octocrylene and about 33% to about 37% of a dibenzoylmethane, about 7% to about 9% of a cellulose encapsulate comprising a cinnamate derivative, about 0.6% to about 5% of a polyquaternium, about 2.5% to about 5% one or more alkyl sulfosuccinate surfactants, about 0.75% to about 2.5% one or more acyl isethionate surfactants, about 0.75% to about 2.5% one or more betaine surfactants and about 0.75% to about 2.5% one or more acyl taurate surfactants. In other aspects of this embodiment, a sunscreen body wash composition disclosed herein comprises about 11% of a cellulose encapsulate comprising about 65% of an octocrylene and about 35% of a dibenzoylmethane, about 8% of a cellulose encapsulate comprising a cinnamate derivative, about 2.5% of a polyquaternium, about 3% to about 4.5% one or more alkyl sulfosuccinate surfactants, about 1% to about 2% one or more acyl isethionate surfactants, about 1% to about 2% one or more betaine surfactants and about 1% to about 2% one or more acyl taurate surfactants.

In aspects of this embodiment, a sunscreen body wash composition disclosed herein comprises about 5% to about 17% of a cellulose encapsulate comprising about 50% to about 80% of an octocrylene and about 20% to about 50% of avobenzone, about 2% to about 14% of a cellulose encapsulate comprising octinoxate, about 0.1% to about 10% of a polyquaternium 10, about 0.5% to about 8% disodium laureth sulfosuccinate, about 0.1% to about 5% sodium cocoyl isethionate, about 0.1% to about 5% cocamidopropyl betaine and about 0.1% to about 5% sodium methyl cocoyl taurate. In other aspects of this embodiment, a sunscreen body wash composition disclosed herein comprises about 7% to about 15% of a cellulose encapsulate comprising about 55% to about 75% of an octocrylene and about 25% to about 45% of avobenzone, about 4% to about 12% of a cellulose encapsulate comprising octinoxate, about 0.2% to about 8% of a polyquaternium 10, about 1% to about 7% disodium laureth sulfosuccinate, about 0.25% to about 4% sodium cocoyl isethionate, about 0.25% to about 4% cocamidopropyl betaine and about 0.25% to about 4% sodium methyl cocoyl taurate. In yet other aspects of this embodiment, a sunscreen body wash composition disclosed herein comprises about 8% to about 14% of a cellulose encapsulate comprising about 60% to about 70% of an octocrylene and about 30% to about 40% of avobenzone, about 5% to about 11% of a cellulose encapsulate comprising octinoxate, about 0.4% to about 6% of a polyquaternium 10, about 2% to about 6% disodium laureth sulfosuccinate, about 0.5% to about 3% sodium cocoyl isethionate, about 0.5% to about 3% cocamidopropyl betaine and about 0.5% to about 3% sodium methyl cocoyl taurate. In still other aspects of this embodiment, a sunscreen body wash composition disclosed herein comprises about 10% to about 12% of a cellulose encapsulate comprising about 63% to about 68% of an octocrylene and about 33% to about 37% of avobenzone, about 7% to about 9% of a cellulose encapsulate comprising octinoxate, about 0.6% to about 5% of a polyquaternium 10, about 2.5% to about 5% disodium laureth sulfosuccinate, about 0.75% to about 2.5% sodium cocoyl isethionate, about 0.75% to about 2.5% cocamidopropyl betaine and about 0.75% to about 2.5% sodium methyl cocoyl taurate. In other aspects of this embodiment, a sunscreen body wash composition disclosed herein comprises about 11% of a cellulose encapsulate comprising about 65% of an octocrylene and about 35% of avobenzone, about 8% of a cellulose encapsulate comprising octinoxate, about 2.5% of a polyquaternium, 10, about 3% to about 4.5% disodium laureth sulfosuccinate, about 1% to about 2% sodium cocoyl isethionate, about 1% to about 2% cocamidopropyl betaine and about 1% to about 2% sodium methyl cocoyl taurate.

In another embodiment, a sunscreen body wash composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen body wash composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen body wash composition disclosed herein comprises about 1% to about 12%, about 2% to about 10%, about 3% to about 9%, about 5% to about 7% or about 6% of a photostabilizing agent with a concomitant reduction in the amount of a broad spectrum UVA/UVB sunscreen active agent of equal value. In other aspects of this embodiment, the sunscreen body wash composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen body wash composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen body wash composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen body wash composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen body wash composition disclosed herein further comprises a film former. In aspects of this embodiment, the sunscreen body wash composition disclosed herein comprises about 1% to about 6%, about 1.5% to about 4.5%, about 2% to about 4%, about 2.5% to about 3.5% or about 3% of a film former. In other aspects of this embodiment, the sunscreen body wash composition disclosed herein comprises an acrylate copolymer as a film former. In yet other aspects of this embodiment, the sunscreen body wash composition disclosed herein an acrylate copolymer is DERMACRYL® AQF.

In another embodiment, a sunscreen body wash composition disclosed herein further comprises a film former as well as a cellulose encapsulate comprising a broad spectrum UVA/UVB sunscreen active agent and a UVA sunscreen active agent and further comprises a photostabilizing agent. In aspects of this embodiment, the sunscreen body wash composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In other aspects of this embodiment, the sunscreen body wash composition disclosed herein comprises trimethoxy benylidene pentanedione as a photostabilizing agent. In aspects of this embodiment, the sunscreen body wash composition disclosed herein comprises about 1% to about 6%, about 1.5% to about 4.5%, about 2% to about 4%, about 2.5% to about 3.5% or about 3% of a film former. In other aspects of this embodiment, the sunscreen body wash composition disclosed herein comprises an acrylate copolymer as a film former. In yet other aspects of this embodiment, the sunscreen body wash composition disclosed herein an acrylate copolymer is DERMACRYL® AQF.

In another embodiment, a sunscreen body wash composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen body wash composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen body wash composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR3535, lemon eucalyptus oil, eucalyptus oil, peppermint oil, geranium oil and clove oil.

In an embodiment, a composition disclosed herein is a sunscreen lotion composition. In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.25% to about 10% one or more emollients and about 0.5% to about 12% one or more thickening agents. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 0.5% to about 8% one or more emollients and about 1% to about 10% one or more thickening agents. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 1% to about 6% one or more emollients and about 1.5% to about 8.5% one or more thickening agents. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 2% to about 5% one or more emollients and about 2.5% to about 6.5% one or more thickening agents. In other aspects of this embodiment, a sunscreen lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 3.4% one or more emollients and about 4.5% one or more thickening agents.

In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 3.5% one or more emollients, about 2% one or more silicone elastomer thickening agents and about 2.5% one or more sodium acrylate-sodium acryloyldimethyl taurate copolymer-based thickening agents.

In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of an octocrylene and about 20% to about 50% of a dibenzoylmethane, about 2% to about 14% of a cellulose encapsulate comprising a cinnamate derivative, about 0.25% to about 10% one or more emollients, about 0.1% to about 9% one or more silicone elastomer thickening agents about 0.1% to about 9% and one or more sodium acrylate-sodium acryloyldimethyl taurate copolymer-based thickening agents. In other aspects of this embodiment, a sunscreen lotion composition disclosed herein comprises about 0.025% to about 5% of a cellulose encapsulate comprising a silicone oil, about 0.25% to about 5% of a cellulose encapsulate comprising a shea oil, about 7% to about 15% of a cellulose encapsulate comprising about 55% to about 75% of an octocrylene and about 25% to about 45% of a dibenzoylmethane, about 4% to about 12% of a cellulose encapsulate comprising a cinnamate derivative, about 0.5% to about 8% one or more emollients, about 0.2% to about 7% one or more silicone elastomer thickening agents about 0.2% to about 7% and one or more sodium acrylate-sodium acryloyldimethyl taurate copolymer-based thickening agents. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of an octocrylene and about 30% to about 40% of a dibenzoylmethane, about 5% to about 11% of a cellulose encapsulate comprising a cinnamate derivative, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of an octocrylene and about 33% to about 37% of a dibenzoylmethane, about 7% to about 9% of a cellulose encapsulate comprising a cinnamate derivative, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of an octocrylene and about 35% of a dibenzoylmethane, about 8% of a cellulose encapsulate comprising a cinnamate derivative, about 3.5% one or more emollients, and about 2% one or more silicone elastomer thickening agents and about 2.5% one or more sodium acrylate-sodium acryloyldimethyl taurate copolymer-based thickening agents.

In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of an octocrylene and about 20% to about 50% of avobenzone, about 2% to about 14% of a cellulose encapsulate comprising octinoxate, about 0.25% to about 10% capryllic capric triglyceride, about 0.1% to about 9% dimethicone-vinyldimethyl trimethylsiloxysilicate-dimethicone crosspolymer and about 0.1% to about 9% acrylate-sodium acryloyldimethyl taurate copolymer-based thickening agent including isohexadecane and polysorbate 80. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of an octocrylene and about 25% to about 45% of avobenzone, about 4% to about 12% of a cellulose encapsulate comprising octinoxate, about 0.5% to about 8% capryllic capric triglyceride, about 0.2% to about 7% dimethicone-vinyldimethyl trimethylsiloxysilicate-dimethicone crosspolymer and about 0.2% to about 7% acrylate-sodium acryloyldimethyl taurate copolymer-based thickening agent including isohexadecane and polysorbate 80. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of an octocrylene and about 30% to about 40% of avobenzone, about 5% to about 11% of a cellulose encapsulate comprising octinoxate, about 1% to about 6% capryllic capric triglyceride, about 0.25% to about 5% dimethicone-vinyldimethyl trimethylsiloxysilicate-dimethicone crosspolymer and about 0.5% to about 5% acrylate-sodium acryloyldimethyl taurate copolymer-based thickening agent including isohexadecane and polysorbate 80. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of an octocrylene and about 33% to about 37% of avobenzone, about 7% to about 9% of a cellulose encapsulate comprising octinoxate, about 2% to about 5% capryllic capric triglyceride, about 0.5% to about 3.5% dimethicone-vinyldimethyl trimethylsiloxysilicate-dimethicone crosspolymer and about 1% to about 4% acrylate-sodium acryloyldimethyl taurate copolymer-based thickening agent including isohexadecane and polysorbate 80. In other aspects of this embodiment, a sunscreen lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of an octocrylene and about 35% of avobenzone, about 8% of a cellulose encapsulate comprising octinoxate, about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80.

In an embodiment, a composition disclosed herein is a sunscreen lotion composition. In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.25% to about 10% one or more emollients and about 0.5% to about 12% one or more thickening agents. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 0.5% to about 8% one or more emollients and about 1% to about 10% one or more thickening agents. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 1% to about 6% one or more emollients and about 1.5% to about 8.5% one or more thickening agents. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of a broad spectrum UVA/UVB sunscreen active agent and about 33% to about 37% of a UVA sunscreen active agent, about 5% to about 7% of a cellulose encapsulate comprising a UVB sunscreen active agent, about 2% to about 5% one or more emollients and about 2.5% to about 6.5% one or more thickening agents. In other aspects of this embodiment, a sunscreen lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of a broad spectrum UVA/UVB sunscreen active agent and about 35% of a UVA sunscreen active agent, about 6% of a cellulose encapsulate comprising a UVB sunscreen active agent, about 3.4% one or more emollients and about 4.5% one or more thickening agents.

In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of a broad spectrum UVA/UVB sunscreen active agent and about 33% to about 37% of a UVA sunscreen active agent, about 5% to about 7% of a cellulose encapsulate comprising a UVB sunscreen active agent, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of a broad spectrum UVA/UVB sunscreen active agent and about 35% of a UVA sunscreen active agent, about 6% of a cellulose encapsulate comprising a UVB sunscreen active agent, about 3.5% one or more emollients, about 2% one or more silicone elastomer thickening agents and about 2.5% one or more sodium acrylate-sodium acryloyldimethyl taurate copolymer-based thickening agents.

In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of an octocrylene and about 20% to about 50% of a dibenzoylmethane, about 1% to about 12% of a cellulose encapsulate comprising a cinnamate derivative, about 0.25% to about 10% one or more emollients, about 0.1% to about 9% one or more silicone elastomer thickening agents about 0.1% to about 9% and one or more sodium acrylate-sodium acryloyldimethyl taurate copolymer-based thickening agents. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of an octocrylene and about 25% to about 45% of a dibenzoylmethane, about 2% to about 10% of a cellulose encapsulate comprising a cinnamate derivative, about 0.5% to about 8% one or more emollients, about 0.2% to about 7% one or more silicone elastomer thickening agents about 0.2% to about 7% and one or more sodium acrylate-sodium acryloyldimethyl taurate copolymer-based thickening agents. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of an octocrylene and about 30% to about 40% of a dibenzoylmethane, about 3% to about 9% of a cellulose encapsulate comprising a cinnamate derivative, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of an octocrylene and about 33% to about 37% of a dibenzoylmethane, about 5% to about 7% of a cellulose encapsulate comprising a cinnamate derivative, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of an octocrylene and about 35% of a dibenzoylmethane, about 6% of a cellulose encapsulate comprising a cinnamate derivative, about 3.5% one or more emollients, and about 2% one or more silicone elastomer thickening agents and about 2.5% one or more sodium acrylate-sodium acryloyldimethyl taurate copolymer-based thickening agents.

In aspects of this embodiment, a sunscreen lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of an octocrylene and about 20% to about 50% of avobenzone, about 1% to about 12% of a cellulose encapsulate comprising octinoxate, about 0.25% to about 10% capryllic capric triglyceride, about 0.1% to about 9% dimethicone-vinyldimethyl trimethylsiloxysilicate-dimethicone crosspolymer and about 0.1% to about 9% acrylate-sodium acryloyldimethyl taurate copolymer-based thickening agent including isohexadecane and polysorbate 80. In other aspects of this embodiment, a sunscreen lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of an octocrylene and about 25% to about 45% of avobenzone, about 2% to about 10% of a cellulose encapsulate comprising octinoxate, about 0.5% to about 8% capryllic capric triglyceride, about 0.2% to about 7% dimethicone-vinyldimethyl trimethylsiloxysilicate-dimethicone crosspolymer and about 0.2% to about 7% acrylate-sodium acryloyldimethyl taurate copolymer-based thickening agent including isohexadecane and polysorbate 80. In yet other aspects of this embodiment, a sunscreen lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of an octocrylene and about 30% to about 40% of avobenzone, about 3% to about 9% of a cellulose encapsulate comprising octinoxate, about 1% to about 6% capryllic capric triglyceride, about 0.25% to about 5% dimethicone-vinyldimethyl trimethylsiloxysilicate-dimethicone crosspolymer and about 0.5% to about 5% acrylate-sodium acryloyldimethyl taurate copolymer-based thickening agent including isohexadecane and polysorbate 80. In still other aspects of this embodiment, a sunscreen lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of an octocrylene and about 33% to about 37% of avobenzone, about 5% to about 7% of a cellulose encapsulate comprising octinoxate, about 2% to about 5% capryllic capric triglyceride, about 0.5% to about 3.5% dimethicone-vinyldimethyl trimethylsiloxysilicate-dimethicone crosspolymer and about 1% to about 4% acrylate-sodium acryloyldimethyl taurate copolymer-based thickening agent including isohexadecane and polysorbate 80. In other aspects of this embodiment, a sunscreen lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of an octocrylene and about 35% of avobenzone, about 6% of a cellulose encapsulate comprising octinoxate, about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80.

In another embodiment, a sunscreen lotion composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen lotion composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen lotion composition disclosed herein comprises about 1% to about 12%, about 2% to about 10%, about 3% to about 9%, about 5% to about 7% or about 6% of a photostabilizing agent agent with a concomitant reduction in the amount of a broad spectrum UVA/UVB sunscreen active agent of equal value. In other aspects of this embodiment, the sunscreen lotion composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen lotion composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen lotion composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen lotion composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen lotion composition disclosed herein further comprises a film former. In aspects of this embodiment, the sunscreen lotion composition disclosed herein comprises about 1% to about 6%, about 1.5% to about 4.5%, about 2% to about 4%, about 2.5% to about 3.5% or about 3% of a film former. In other aspects of this embodiment, the sunscreen lotion composition disclosed herein comprises an acrylate copolymer as a film former. In yet other aspects of this embodiment, the sunscreen lotion composition disclosed herein an acrylate copolymer is DERMACRYL® AQF.

In another embodiment, a sunscreen lotion composition disclosed herein further comprises a film former as well as a cellulose encapsulate comprising a broad spectrum UVA/UVB sunscreen active agent and a UVA sunscreen active agent and further comprises a photostabilizing agent. In aspects of this embodiment, the sunscreen lotion composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In other aspects of this embodiment, the sunscreen lotion composition disclosed herein comprises trimethoxy benylidene pentanedione as a photostabilizing agent. In aspects of this embodiment, the sunscreen lotion composition disclosed herein comprises about 1% to about 6%, about 1.5% to about 4.5%, about 2% to about 4%, about 2.5% to about 3.5% or about 3% of a film former. In other aspects of this embodiment, the sunscreen lotion composition disclosed herein comprises an acrylate copolymer as a film former. In yet other aspects of this embodiment, the sunscreen lotion composition disclosed herein an acrylate copolymer is DERMACRYL® AQF.

In another embodiment, a sunscreen lotion composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen lotion composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen lotion composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR3535, lemon eucalyptus oil, eucalyptus oil, peppermint oil, geranium oil and clove oil.

In an embodiment, a composition disclosed herein is a sunscreen after shower body lotion composition. In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.5% to about 8% of a polyquaternium, about 0.5% to about 8% of a film former, about 0.25% to about 10% one or more emollients and about 0.5% to about 12% one or more thickening agents. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 1% to about 5% of a polyquaternium, about 1% to about 5% of a film former, about 0.5% to about 8% one or more emollients and about 1% to about 10% one or more thickening agents. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 1.5% to about 3.5% of a polyquaternium, about 1.5% to about 3.5% of a film former, about 1% to about 6% one or more emollients and about 1.5% to about 8.5% one or more thickening agents. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 2% to about 3% of a polyquaternium, about 2% to about 3% of a film former, about 2% to about 5% one or more emollients and about 2.5% to about 6.5% one or more thickening agents. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 2.5% of a polyquaternium, about 2.5% of a film former, about 3.4% one or more emollients and about 4.5% one or more thickening agents.

In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of a broad spectrum UVA/UVB sunscreen active agent and about 20% to about 50% of a UVA sunscreen active agent, about 2% to about 14% of a cellulose encapsulate comprising a UVB sunscreen active agent, about 0.5% to about 8% of a polyquaternium, about 0.5% to about 8% of an acrylate copolymer, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of a broad spectrum UVA/UVB sunscreen active agent and about 25% to about 45% of a UVA sunscreen active agent, about 4% to about 12% of a cellulose encapsulate comprising a UVB sunscreen active agent, about 1% to about 5% of a polyquaternium, about 1% to about 5% of an acrylate copolymer, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of a broad spectrum UVA/UVB sunscreen active agent and about 30% to about 40% of a UVA sunscreen active agent, about 5% to about 11% of a cellulose encapsulate comprising a UVB sunscreen active agent, about 1.5% to about 3.5% of a polyquaternium, about 1.5% to about 3.5% of an acrylate copolymer, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of a broad spectrum UVA/UVB sunscreen active agent and about 33% to about 37% of a UVA sunscreen active agent, about 7% to about 9% of a cellulose encapsulate comprising a UVB sunscreen active agent, about 2% to about 3% of a polyquaternium, about 2% to about 3% of an acrylate copolymer, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of a broad spectrum UVA/UVB sunscreen active agent and about 35% of a UVA sunscreen active agent, about 8% of a cellulose encapsulate comprising a UVB sunscreen active agent, about 2.5% of a polyquaternium, about 2.5% of an acrylate copolymer, about 3.5% one or more emollients, about 2% one or more silicone elastomer thickening agents and about 2.5% one or more sodium acrylate-sodium acryloyldimethyl taurate copolymer-based thickening agents.

In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of an octocrylene and about 20% to about 50% of a dibenzoylmethane, about 2% to about 14% of a cellulose encapsulate comprising a cinnamate derivative, about 0.5% to about 8% of a polyquaternium, about 0.5% to about 8% of an acrylate copolymer, about 0.25% to about 10% one or more emollients, about 0.1% to about 9% one or more silicone elastomer thickening agents about 0.1% to about 9% and one or more sodium acrylate-sodium acryloyldimethyl taurate copolymer-based thickening agents. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of an octocrylene and about 25% to about 45% of a dibenzoylmethane, about 4% to about 12% of a cellulose encapsulate comprising a cinnamate derivative, about 1% to about 5% of a polyquaternium, about 1% to about 5% of an acrylate copolymer, about 0.5% to about 8% one or more emollients, about 0.2% to about 7% one or more silicone elastomer thickening agents about 0.2% to about 7% and one or more sodium acrylate-sodium acryloyldimethyl taurate copolymer-based thickening agents. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of an octocrylene and about 30% to about 40% of a dibenzoylmethane, about 5% to about 11% of a cellulose encapsulate comprising a cinnamate derivative, about 1.5% to about 3.5% of a polyquaternium, about 1.5% to about 3.5% of an acrylate copolymer, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of an octocrylene and about 33% to about 37% of a dibenzoylmethane, about 7% to about 9% of a cellulose encapsulate comprising a cinnamate derivative, about 2% to about 3% of a polyquaternium, about 2% to about 3% of an acrylate copolymer, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of an octocrylene and about 35% of a dibenzoylmethane, about 8% of a cellulose encapsulate comprising a cinnamate derivative, about 2.5% of a polyquaternium, about 2.5% of an acrylate copolymer, about 3.5% one or more emollients, and about 2% one or more silicone elastomer thickening agents and about 2.5% one or more sodium acrylate-sodium acryloyldimethyl taurate copolymer-based thickening agents.

In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 5% to about 17% of a cellulose encapsulate comprising about 50% to about 80% of an octocrylene and about 20% to about 50% of avobenzone, about 2% to about 14% of a cellulose encapsulate comprising octinoxate, about 0.5% to about 8% of a polyquaternium 4 or a polyquaternium 10, about 0.5% to about 8% of DERMACRYL® AQF, about 0.25% to about 10% capryllic capric triglyceride, about 0.1% to about 9% dimethicone-vinyldimethyl trimethylsiloxysilicate-dimethicone crosspolymer and about 0.1% to about 9% acrylate-sodium acryloyldimethyl taurate copolymer-based thickening agent including isohexadecane and polysorbate 80. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 7% to about 15% of a cellulose encapsulate comprising about 55% to about 75% of an octocrylene and about 25% to about 45% of avobenzone, about 4% to about 12% of a cellulose encapsulate comprising octinoxate, about 1% to about 5% of a polyquaternium 4 or a polyquaternium 10, about 1% to about 5% of DERMACRYL® AQF, about 0.5% to about 8% capryllic capric triglyceride, about 0.2% to about 7% dimethicone-vinyldimethyl trimethylsiloxysilicate-dimethicone crosspolymer and about 0.2% to about 7% acrylate-sodium acryloyldimethyl taurate copolymer-based thickening agent including isohexadecane and polysorbate 80. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 8% to about 14% of a cellulose encapsulate comprising about 60% to about 70% of an octocrylene and about 30% to about 40% of avobenzone, about 5% to about 11% of a cellulose encapsulate comprising octinoxate, about 1.5% to about 3.5% of a polyquaternium 4 or a polyquaternium 10, about 1.5% to about 3.5% of DERMACRYL® AQF, about 1% to about 6% capryllic capric triglyceride, about 0.25% to about 5% dimethicone-vinyldimethyl trimethylsiloxysilicate-dimethicone crosspolymer and about 0.5% to about 5% acrylate-sodium acryloyldimethyl taurate copolymer-based thickening agent including isohexadecane and polysorbate 80. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 10% to about 12% of a cellulose encapsulate comprising about 63% to about 68% of an octocrylene and about 33% to about 37% of avobenzone, about 7% to about 9% of a cellulose encapsulate comprising octinoxate, about 2% to about 3% of a polyquaternium 4 or a polyquaternium 10, about 2% to about 3% of DERMACRYL® AQF, about 2% to about 5% capryllic capric triglyceride, about 0.5% to about 3.5% dimethicone-vinyldimethyl trimethylsiloxysilicate-dimethicone crosspolymer and about 1% to about 4% acrylate-sodium acryloyldimethyl taurate copolymer-based thickening agent including isohexadecane and polysorbate 80. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 11% of a cellulose encapsulate comprising about 65% of an octocrylene and about 35% of avobenzone, about 8% of a cellulose encapsulate comprising octinoxate, about 2.5% of a polyquaternium 4 or a polyquaternium 10, about 2.5% of DERMACRYL® AQF, about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80.

In another embodiment, a sunscreen after shower body lotion composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen after shower body lotion composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen after shower body lotion composition disclosed herein comprises about 1% to about 12%, about 2% to about 10%, about 3% to about 9%, about 5% to about 7% or about 6% of a photostabilizing agent with a concomitant reduction in the amount of a broad spectrum UVA/UVB sunscreen active agent of equal value. In other aspects of this embodiment, the sunscreen after shower body lotion composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen after shower body lotion composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen after shower body lotion composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen after shower body lotion composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen after shower body lotion composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen after shower body lotion composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen after shower body lotion composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR-3535, lemon eucalyptus oil, eucalyptus oil, peppermint oil, geranium oil and clove oil.

In an embodiment, a composition disclosed herein is a sunscreen after shower body lotion composition. In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.5% to about 8% of a polyquaternium, about 0.5% to about 8% of a film former, about 0.25% to about 10% one or more emollients and about 0.5% to about 12% one or more thickening agents. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 1% to about 5% of a polyquaternium, about 1% to about 5% of a film former, about 0.5% to about 8% one or more emollients and about 1% to about 10% one or more thickening agents. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 1.5% to about 3.5% of a polyquaternium, about 1.5% to about 3.5% of a film former, about 1% to about 6% one or more emollients and about 1.5% to about 8.5% one or more thickening agents. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 61% to about 66% of a broad spectrum UVA/UVB sunscreen active agent and about 33% to about 37% of a UVA sunscreen active agent, about 5% to about 7% of a cellulose encapsulate comprising a UVB sunscreen active agent, about 2% to about 3% of a polyquaternium, about 2% to about 3% of a film former, about 2% to about 5% one or more emollients and about 2.5% to about 6.5% one or more thickening agents. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of a broad spectrum UVA/UVB sunscreen active agent and about 35% of a UVA sunscreen active agent, about 6% of a cellulose encapsulate comprising a UVB sunscreen active agent, about 2.5% of a polyquaternium, about 2.5% of a film former, about 3.4% one or more emollients and about 4.5% one or more thickening agents.

In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.5% to about 8% of a polyquaternium, about 0.5% to about 8% of an acrylate copolymer, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 1% to about 5% of a polyquaternium, about 1% to about 5% of an acrylate copolymer, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 1.5% to about 3.5% of a polyquaternium, about 1.5% to about 3.5% of an acrylate copolymer, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of a broad spectrum UVA/UVB sunscreen active agent and about 33% to about 37% of a UVA sunscreen active agent, about 5% to about 7% of a cellulose encapsulate comprising a UVB sunscreen active agent, about 2% to about 3% of a polyquaternium, about 2% to about 3% of an acrylate copolymer, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of a broad spectrum UVA/UVB sunscreen active agent and about 35% of a UVA sunscreen active agent, about 6% of a cellulose encapsulate comprising a UVB sunscreen active agent, about 2.5% of a polyquaternium, about 2.5% of an acrylate copolymer, about 3.5% one or more emollients, about 2% one or more silicone elastomer thickening agents and about 2.5% one or more sodium acrylate-sodium acryloyldimethyl taurate copolymer-based thickening agents.

In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of an octocrylene and about 20% to about 50% of a dibenzoylmethane, about 1% to about 12% of a cellulose encapsulate comprising a cinnamate derivative, about 0.5% to about 8% of a polyquaternium, about 0.5% to about 8% of an acrylate copolymer, about 0.25% to about 10% one or more emollients, about 0.1% to about 9% one or more silicone elastomer thickening agents about 0.1% to about 9% and one or more sodium acrylate-sodium acryloyldimethyl taurate copolymer-based thickening agents. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of an octocrylene and about 25% to about 45% of a dibenzoylmethane, about 2% to about 10% of a cellulose encapsulate comprising a cinnamate derivative, about 1% to about 5% of a polyquaternium, about 1% to about 5% of an acrylate copolymer, about 0.5% to about 8% one or more emollients, about 0.2% to about 7% one or more silicone elastomer thickening agents about 0.2% to about 7% and one or more sodium acrylate-sodium acryloyldimethyl taurate copolymer-based thickening agents. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of an octocrylene and about 30% to about 40% of a dibenzoylmethane, about 3% to about 9% of a cellulose encapsulate comprising a cinnamate derivative, about 1% to about 6% one or more emollients, about 1.5% to about 3.5% of a polyquaternium, about 1.5% to about 3.5% of an acrylate copolymer, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of an octocrylene and about 33% to about 37% of a dibenzoylmethane, about 5% to about 7% of a cellulose encapsulate comprising a cinnamate derivative, about 2% to about 3% of a polyquaternium, about 2% to about 3% of an acrylate copolymer, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of an octocrylene and about 35% of a dibenzoylmethane, about 6% of a cellulose encapsulate comprising a cinnamate derivative, about 2.5% of a polyquaternium, about 2.5% of an acrylate copolymer, about 3.5% one or more emollients, and about 2% one or more silicone elastomer thickening agents and about 2.5% one or more sodium acrylate-sodium acryloyldimethyl taurate copolymer-based thickening agents.

In aspects of this embodiment, a sunscreen after shower body lotion composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of an octocrylene and about 20% to about 50% of avobenzone, about 1% to about 12% of a cellulose encapsulate comprising octinoxate, about 0.5% to about 8% of a polyquaternium 4 or a polyquaternium 10, about 0.5% to about 8% of DERMACRYL® AQF, about 0.25% to about 10% capryllic capric triglyceride, about 0.1% to about 9% dimethicone-vinyldimethyl trimethylsiloxysilicate-dimethicone crosspolymer and about 0.1% to about 9% acrylate-sodium acryloyldimethyl taurate copolymer-based thickening agent including isohexadecane and polysorbate 80. In other aspects of this embodiment, a sunscreen after shower body lotion composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of an octocrylene and about 25% to about 45% of avobenzone, about 2% to about 10% of a cellulose encapsulate comprising octinoxate, about 1% to about 5% of a polyquaternium 4 or a polyquaternium 10, about 1% to about 5% of DERMACRYL® AQF, about 0.5% to about 8% capryllic capric triglyceride, about 0.2% to about 7% dimethicone-vinyldimethyl trimethylsiloxysilicate-dimethicone crosspolymer and about 0.2% to about 7% acrylate-sodium acryloyldimethyl taurate copolymer-based thickening agent including isohexadecane and polysorbate 80. In yet other aspects of this embodiment, a sunscreen after shower body lotion composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of an octocrylene and about 30% to about 40% of avobenzone, about 3% to about 9% of a cellulose encapsulate comprising octinoxate, about 1.5% to about 3.5% of a polyquaternium 4 or a polyquaternium 10, about 1.5% to about 3.5% of DERMACRYL® AQF, about 1% to about 6% capryllic capric triglyceride, about 0.25% to about 5% dimethicone-vinyldimethyl trimethylsiloxysilicate-dimethicone crosspolymer and about 0.5% to about 5% acrylate-sodium acryloyldimethyl taurate copolymer-based thickening agent including isohexadecane and polysorbate 80. In still other aspects of this embodiment, a sunscreen after shower body lotion composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of an octocrylene and about 33% to about 37% of avobenzone, about 5% to about 7% of a cellulose encapsulate comprising octinoxate, about 2% to about 3% of a polyquaternium 4 or a polyquaternium 10, about 2% to about 3% of DERMACRYL® AQF, about 2% to about 5% capryllic capric triglyceride, about 0.5% to about 3.5% dimethicone-vinyldimethyl trimethylsiloxysilicate-dimethicone crosspolymer and about 1% to about 4% acrylate-sodium acryloyldimethyl taurate copolymer-based thickening agent including isohexadecane and polysorbate 80. In other aspects of this embodiment, a sunscreen after shower body lotion composition disclosed herein comprises about 0.15% of a cellulose encapsulate comprising a silicone oil, about 0.2% of a cellulose encapsulate comprising a shea oil, about 8% of a cellulose encapsulate comprising about 65% of an octocrylene and about 35% of avobenzone, about 6% of a cellulose encapsulate comprising octinoxate, about 2.5% of a polyquaternium 4 or a polyquaternium 10, about 2.5% of DERMACRYL® AQF, about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80.

In another embodiment, a sunscreen after shower body lotion composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen after shower body lotion composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen after shower body lotion composition disclosed herein comprises about 1% to about 12%, about 2% to about 10%, about 3% to about 9%, about 5% to about 7% or about 6% of a photostabilizing agent with a concomitant reduction in the amount of a broad spectrum UVA/UVB sunscreen active agent of equal value. In other aspects of this embodiment, the sunscreen after shower body lotion composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen after shower body lotion composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen after shower body lotion composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen after shower body lotion composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen after shower body lotion composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen after shower body lotion composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen after shower body lotion composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR-3535, lemon eucalyptus oil, eucalyptus oil, peppermint oil, geranium oil and clove oil.

In an embodiment, a composition disclosed herein is a sunscreen shampoo composition. In aspects of this embodiment, a sunscreen shampoo composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.1% to about 10% of a polyquaternium, and about 1% to about 20% one or more surfactants. In other aspects of this embodiment, a sunscreen shampoo composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 0.1% to about 5% of a polyquaternium, and about 4% to about 14% one or more surfactants. In yet other aspects of this embodiment, a sunscreen shampoo composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 0.1% to about 3% of a polyquaternium, and about 7% to about 11% one or more surfactants. In still other aspects of this embodiment, a sunscreen shampoo composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 61% to about 66% of a broad spectrum UVA/UVB sunscreen active agent and about 33% to about 37% of a UVA sunscreen active agent, about 5% to about 7% of a cellulose encapsulate comprising a UVB sunscreen active agent, about 0.25% to about 2.5% of a polyquaternium, and about 8% to about 10% one or more surfactants. In other aspects of this embodiment, a sunscreen shampoo composition disclosed herein comprises about 0.15% of a cellulose encapsulate comprising a silicone oil, about 0.2% of a cellulose encapsulate comprising a shea oil, about 11% of a cellulose encapsulate comprising about 65% of a broad spectrum UVA/UVB sunscreen active agent and about 35% of a UVA sunscreen active agent, about 9% of a cellulose encapsulate comprising a UVB sunscreen active agent, about 0.5% of a polyquaternium, and about 8.8% one or more surfactants.

In aspects of this embodiment, a sunscreen shampoo composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.1% to about 10% of a polyquaternium, about 1% to about 16% of one or more anionic surfactants, about 0.1% to about 10% of an amphoteric surfactant and about 0.1% to about 10% of a surfactant. In other aspects of this embodiment, a sunscreen shampoo composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 0.1% to about 5% of a polyquaternium, about 1% to about 12% of one or more anionic surfactants, about 0.25% to about 8% of an amphoteric surfactant and about 0.25% to about 8% of a surfactant. In yet other aspects of this embodiment, a sunscreen shampoo composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 0.1% to about 3% of a polyquaternium, about 3% to about 9% of one or more anionic surfactants, about 0.5% to about 5% of an amphoteric surfactant and about 0.5% to about 5% of a surfactant. In still other aspects of this embodiment, a sunscreen shampoo composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of a broad spectrum UVA/UVB sunscreen active agent and about 33% to about 37% of a UVA sunscreen active agent, about 5% to about 7% of a cellulose encapsulate comprising a UVB sunscreen active agent, about 0.25% to about 2.5% of a polyquaternium, about 5% to about 7% of one or more anionic surfactants, about 1% to about 3% of an amphoteric surfactant and about 1% to about 3% of a surfactant. In other aspects of this embodiment, a sunscreen shampoo composition disclosed herein comprises about 0.15% of a cellulose encapsulate comprising a silicone oil, about 0.2% of a cellulose encapsulate comprising a shea oil, about 8% of a cellulose encapsulate comprising about 65% of a broad spectrum UVA/UVB sunscreen active agent and about 35% of a UVA sunscreen active agent, about 6% of a cellulose encapsulate comprising a UVB sunscreen active agent, about 0.5% of a polyquaternium, about 5.6% of one or more anionic surfactants, about 1.6% of an amphoteric surfactant and about 1.6% of a surfactant.

In aspects of this embodiment, a sunscreen shampoo composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of an octocrylene and about 20% to about 50% of a dibenzoylmethane, about 1% to about 12% of a cellulose encapsulate comprising a cinnamate derivative, about 0.1% to about 10% of a polyquaternium, about 0.1% to about 15% of an alkyl sulfosuccinate surfactant, about 0.1% to about 10% of an isethionate surfactant, about 0.1% to about 10% of a betaine surfactant and about 0.1% to about 10% of an acyl taurate surfactant. In other aspects of this embodiment, a sunscreen shampoo composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of an octocrylene and about 25% to about 45% of a dibenzoylmethane, about 2% to about 10% of a cellulose encapsulate comprising a cinnamate derivative, about 0.1% to about 5% of a polyquaternium, about 0.5% to about 10% of an alkyl sulfosuccinate surfactant, about 0.25% to about 8% of an isethionate surfactant, about 0.25% to about 8% of a betaine surfactant and about 0.25% to about 8% of an acyl taurate surfactant. In yet other aspects of this embodiment, a sunscreen shampoo composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of an octocrylene and about 30% to about 40% of a dibenzoylmethane, about 3% to about 9% of a cellulose encapsulate comprising a cinnamate derivative, about 0.1% to about 3% of a polyquaternium, about 1% to about 7% of an alkyl sulfosuccinate surfactant, about 0.5% to about 5% of an isethionate surfactant, about 0.5% to about 5% of a betaine surfactant and about 0.5% to about 5% of an acyl taurate surfactant. In still other aspects of this embodiment, a sunscreen shampoo composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of an octocrylene and about 33% to about 37% of a dibenzoylmethane, about 5% to about 7% of a cellulose encapsulate comprising a cinnamate derivative, about 0.25% to about 2.5% of a polyquaternium, about 3% to about 5% of an alkyl sulfosuccinate surfactant, about 1% to about 3% of an isethionate surfactant, about 1% to about 3% of a betaine surfactant and about 1% to about 3% of an acyl taurate surfactant. In other aspects of this embodiment, a sunscreen shampoo composition disclosed herein comprises about 0.15% of a cellulose encapsulate comprising a silicone oil, about 0.2% of a cellulose encapsulate comprising a shea oil, about 8% of a cellulose encapsulate comprising about 65% of an octocrylene and about 35% of a dibenzoylmethane, about 6% of a cellulose encapsulate comprising a cinnamate derivative, about 0.5% of a polyquaternium, about 4% of an alkyl sulfosuccinate surfactant, about 1.6% of an isethionate surfactant, about 1.6% of a betaine surfactant and about 1.6% of an acyl taurate surfactant.

In aspects of this embodiment, a sunscreen shampoo composition disclosed herein comprises about 0.01% to about 7% of a cellulose encapsulate comprising a silicone oil, about 0.01% to about 7% of a cellulose encapsulate comprising a shea oil, about 2% to about 14% of a cellulose encapsulate comprising about 50% to about 80% of an octocrylene and about 20% to about 50% of avobenzone, about 1% to about 12% of a cellulose encapsulate comprising octinoxate, about 0.1% to about 10% of polyquaternium 10, about 0.1% to about 15% of disodium laureth sulfosuccinate, about 0.1% to about 10% of sodium cocoyl isethionate, about 0.1% to about 10% of cocamidopropyl betaine and about 0.1% to about 10% of sodium methyl cocoyl taurate. In other aspects of this embodiment, a sunscreen shampoo composition disclosed herein comprises about 0.025% to about 5% of a cellulose encapsulate comprising a silicone oil, about 0.025% to about 5% of a cellulose encapsulate comprising a shea oil, about 4% to about 12% of a cellulose encapsulate comprising about 55% to about 75% of an octocrylene and about 25% to about 45% of avobenzone, about 2% to about 10% of a cellulose encapsulate comprising octinoxate, about 0.1% to about 5% of polyquaternium 10, about 0.5% to about 10% of disodium laureth sulfosuccinate, about 0.25% to about 8% of sodium cocoyl isethionate, about 0.25% to about 8% of cocamidopropyl betaine and about 0.25% to about 8% of sodium methyl cocoyl taurate. In yet other aspects of this embodiment, a sunscreen shampoo composition disclosed herein comprises about 0.05% to about 2% of a cellulose encapsulate comprising a silicone oil, about 0.05% to about 2% of a cellulose encapsulate comprising a shea oil, about 5% to about 11% of a cellulose encapsulate comprising about 60% to about 70% of an octocrylene and about 30% to about 40% of avobenzone, about 3% to about 9% of a cellulose encapsulate comprising octinoxate, about 0.1% to about 3% of polyquaternium 10, about 1% to about 7% of disodium laureth sulfosuccinate, about 0.5% to about 5% of sodium cocoyl isethionate, about 0.5% to about 5% of cocamidopropyl betaine and about 0.5% to about 5% of sodium methyl cocoyl taurate. In still other aspects of this embodiment, a sunscreen shampoo composition disclosed herein comprises about 0.1% to about 1% of a cellulose encapsulate comprising a silicone oil, about 0.1% to about 1% of a cellulose encapsulate comprising a shea oil, about 7% to about 9% of a cellulose encapsulate comprising about 63% to about 68% of an octocrylene and about 33% to about 37% of avobenzone, about 5% to about 7% of a cellulose encapsulate comprising octinoxate, about 0.25% to about 2.5% of polyquaternium 10, about 3% to about 5% of disodium laureth sulfosuccinate, about 1% to about 3% of sodium cocoyl isethionate, about 1% to about 3% of cocamidopropyl betaine and about 1% to about 3% of sodium methyl cocoyl taurate. In other aspects of this embodiment, a sunscreen shampoo composition disclosed herein comprises about 0.15% of a cellulose encapsulate comprising a silicone oil, about 0.2% of a cellulose encapsulate comprising a shea oil, about 8% of a cellulose encapsulate comprising about 65% of an octocrylene and about 35% of avobenzone, about 6% of a cellulose encapsulate comprising octinoxate, about 0.5% of polyquaternium 10, about 4% of disodium laureth sulfosuccinate, about 1.6% of sodium cocoyl isethionate, about 1.6% of cocamidopropyl betaine and about 1.6% of sodium methyl cocoyl taurate.

In another embodiment, a sunscreen shampoo composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen shampoo composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen shampoo composition disclosed herein comprises about 1% to about 12%, about 2% to about 10%, about 3% to about 9%, about 5% to about 7% or about 6% of a photostabilizing agent with a concomitant reduction in the amount of a broad spectrum UVA/UVB sunscreen active agent of equal value. In other aspects of this embodiment, the sunscreen shampoo composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen shampoo composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen shampoo composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen shampoo composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen shampoo composition disclosed herein further comprises a film former. In aspects of this embodiment, the sunscreen shampoo composition disclosed herein comprises about 1% to about 6%, about 1.5% to about 4.5%, about 2% to about 4%, about 2.5% to about 3.5% or about 3% of a film former. In other aspects of this embodiment, the sunscreen shampoo composition disclosed herein comprises an acrylate copolymer as a film former. In yet other aspects of this embodiment, the sunscreen shampoo composition disclosed herein an acrylate copolymer is DERMACRYL® AQF.

In another embodiment, a sunscreen shampoo composition disclosed herein further comprises a film former as well as a cellulose encapsulate comprising a broad spectrum UVA/UVB sunscreen active agent and a UVA sunscreen active agent and further comprises a photostabilizing agent. In aspects of this embodiment, the sunscreen shampoo composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In other aspects of this embodiment, the sunscreen shampoo composition disclosed herein comprises trimethoxy benzylidene pentanedione as a photostabilizing agent. In aspects of this embodiment, the sunscreen shampoo composition disclosed herein comprises about 1% to about 6%, about 1.5% to about 4.5%, about 2% to about 4%, about 2.5% to about 3.5% or about 3% of a film former. In other aspects of this embodiment, the sunscreen shampoo composition disclosed herein comprises an acrylate copolymer as a film former. In yet other aspects of this embodiment, the sunscreen shampoo composition disclosed herein an acrylate copolymer is DERMACRYL® AQF.

In another embodiment, a sunscreen shampoo composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen shampoo composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen shampoo composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR-3535, lemon eucalyptus oil, eucalyptus oil, peppermint oil, geranium oil and clove oil.

In another embodiment, a sunscreen shampoo composition disclosed herein further comprises additional surfactants. In aspects of this embodiment, the sunscreen shampoo composition disclosed herein comprises about 20% to about 50% of additional surfactants. In aspects of this embodiment, additional surfactants include additional cationic surfactants, anionic surfactants, non-ionic surfactants, zwitterionic surfactants, amphoteric surfactants, or any combination thereof.

In an embodiment, a composition disclosed herein is a sunscreen lip balm composition. In aspects of this embodiment, a sunscreen soap composition disclosed herein comprises about 9% to about 21% of a cellulose encapsulate comprising about 45% to about 57% of a broad spectrum UVA/UVB sunscreen active agent, about 7% to about 19% of a UVA sunscreen active agent and about 18% to about 30% of a UVB sunscreen active agent, about 19% to about 31% of a film former and about 6% to about 18% of one or more emollients. In other aspects of this embodiment, a sunscreen soap composition disclosed herein comprises about 11% to about 19% of a cellulose encapsulate comprising about 47% to about 55% of a broad spectrum UVA/UVB sunscreen active agent, about 9% to about 17% of a UVA sunscreen active agent and about 20% to about 28% of a UVB sunscreen active agent, about 21% to about 29% of a film former and about 8% to about 16% of one or more emollients. In yet other aspects of this embodiment, a sunscreen soap composition disclosed herein comprises about 12% to about 18% of a cellulose encapsulate comprising about 48% to about 54% of a broad spectrum UVA/UVB sunscreen active agent, about 10% to about 16% of a UVA sunscreen active agent and about 21% to about 27% of a UVB sunscreen active agent, about 22% to about 28% of a film former and about 9% to about 15% of one or more emollients. In still other aspects of this embodiment, a sunscreen soap composition disclosed herein comprises about 14% to about 16% of a cellulose encapsulate comprising about 50% to about 52% of a broad spectrum UVA/UVB sunscreen active agent, about 12% to about 14% of a UVA sunscreen active agent and about 23% to about 25% of a UVB sunscreen active agent, about 24% to about 26% of a film former and about 11% to about 13% of one or more emollients. In other aspects of this embodiment, a sunscreen soap composition disclosed herein comprises about 15% of a cellulose encapsulate comprising about 51% of a broad spectrum UVA/UVB sunscreen active agent, about 13% of a UVA sunscreen active agent and about 24% of a UVB sunscreen active agent, about 25% of a film former and about 12% of one or more emollients.

In aspects of this embodiment, a sunscreen soap composition disclosed herein comprises about 9% to about 21% of a cellulose encapsulate comprising about 45% to about 57% of octocrylene, about 7% to about 19% of dibenzoylmethane and about 18% to about 30% of homosalate or octyl salicylate, about 19% to about 31% of petroleum and about 6% to about 18% of cocoa butter. In other aspects of this embodiment, a sunscreen soap composition disclosed herein comprises about 11% to about 19% of a cellulose encapsulate comprising about 47% to about 55% of octocrylene, about 9% to about 17% of dibenzoylmethane and about 20% to about 28% of homosalate or octyl salicylate, about 21% to about 29% of petroleum and about 8% to about 16% of cocoa butter. In yet other aspects of this embodiment, a sunscreen soap composition disclosed herein comprises about 12% to about 18% of a cellulose encapsulate comprising about 48% to about 54% of octocrylene, about 10% to about 16% of dibenzoylmethane and about 21% to about 27% of homosalate or octyl salicylate, about 22% to about 28% of petroleum and about 9% to about 15% of cocoa butter. In still other aspects of this embodiment, a sunscreen soap composition disclosed herein comprises about 14% to about 16% of a cellulose encapsulate comprising about 50% to about 52% of octocrylene, about 12% to about 14% of dibenzoylmethane and about 23% to about 25% of homosalate or octyl salicylate, about 24% to about 26% of petroleum and about 11% to about 13% of cocoa butter. In other aspects of this embodiment, a sunscreen soap composition disclosed herein comprises about 15% of a cellulose encapsulate comprising about 51% of octocrylene, about 13% of dibenzoylmethane and about 24% of homosalate or octyl salicylate, about 25% of petroleum and about 12% of cocoa butter.

In aspects of this embodiment, a sunscreen soap composition disclosed herein comprises about 9% to about 21% of a cellulose encapsulate comprising about 45% to about 57% of octocrylene, about 7% to about 19% of avobenzone and about 18% to about 30% of homosalate or octyl salicylate, about 19% to about 31% of petroleum and about 6% to about 18% of cocoa butter. In other aspects of this embodiment, a sunscreen soap composition disclosed herein comprises about 11% to about 19% of a cellulose encapsulate comprising about 47% to about 55% of octocrylene, about 9% to about 17% of avobenzone and about 20% to about 28% of homosalate or octyl salicylate, about 21% to about 29% of petroleum and about 8% to about 16% of cocoa butter. In yet other aspects of this embodiment, a sunscreen soap composition disclosed herein comprises about 12% to about 18% of a cellulose encapsulate comprising about 48% to about 54% of octocrylene, about 10% to about 16% of avobenzone and about 21% to about 27% of homosalate or octyl salicylate, about 22% to about 28% of petroleum and about 9% to about 15% of cocoa butter. In still other aspects of this embodiment, a sunscreen soap composition disclosed herein comprises about 14% to about 16% of a cellulose encapsulate comprising about 50% to about 52% of octocrylene, about 12% to about 14% of avobenzone and about 23% to about 25% of homosalate or octyl salicylate, about 24% to about 26% of petroleum and about 11% to about 13% of cocoa butter. In other aspects of this embodiment, a sunscreen soap composition disclosed herein comprises about 15% of a cellulose encapsulate comprising about 51% of octocrylene, about 13% of avobenzone and about 24% of homosalate or octyl salicylate, about 25% of petroleum and about 12% of cocoa butter.

In another embodiment, a sunscreen lip balm composition disclosed herein comprises a cellulose encapsulate comprising a broad spectrum UVA/UVB sunscreen active agent and a UVA sunscreen active agent and further comprises one or more photostabilizing agent. In aspects of this embodiment, the sunscreen lip balm composition disclosed herein comprises about 1% to about 12%, about 2% to about 10%, about 3% to about 9%, about 5% to about 7% or about 6% of a photostabilizing agent. In other aspects of this embodiment, the sunscreen lip balm composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen lip balm composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent. In still other aspects of this embodiment, the sunscreen lip balm composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent. In other aspects of this embodiment, the sunscreen lip balm composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen lip balm composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen lip balm composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen lip balm composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR-3535, lemon eucalyptus oil, eucalyptus oil, peppermint oil, geranium oil and clove oil.

In aspects of this embodiment, a sunscreen soap composition disclosed herein comprises about 9% to about 21% of a cellulose encapsulate comprising about 45% to about 57% of a first UVB sunscreen active agent, about 7% to about 19% of a UVA sunscreen active agent and about 18% to about 30% of a second UVB sunscreen active agent, about 19% to about 31% of a film former and about 6% to about 18% of one or more emollients. In other aspects of this embodiment, a sunscreen soap composition disclosed herein comprises about 11% to about 19% of a cellulose encapsulate comprising about 47% to about 55% of a first UVB sunscreen active agent, about 9% to about 17% of a UVA sunscreen active agent and about 20% to about 28% of a second UVB sunscreen active agent, about 21% to about 29% of a film former and about 8% to about 16% of one or more emollients. In yet other aspects of this embodiment, a sunscreen soap composition disclosed herein comprises about 12% to about 18% of a cellulose encapsulate comprising about 48% to about 54% of a first UVB sunscreen active agent, about 10% to about 16% of a UVA sunscreen active agent and about 21% to about 27% of a second UVB sunscreen active agent, about 22% to about 28% of a film former and about 9% to about 15% of one or more emollients. In still other aspects of this embodiment, a sunscreen soap composition disclosed herein comprises about 14% to about 16% of a cellulose encapsulate comprising about 50% to about 52% of a first UVB sunscreen active agent, about 12% to about 14% of a UVA sunscreen active agent and about 23% to about 25% of a second UVB sunscreen active agent, about 24% to about 26% of a film former and about 11% to about 13% of one or more emollients. In other aspects of this embodiment, a sunscreen soap composition disclosed herein comprises about 15% of a cellulose encapsulate comprising about 51% of a first UVB sunscreen active agent, about 13% of a UVA sunscreen active agent and about 24% of a second UVB sunscreen active agent, about 25% of a film former and about 12% of one or more emollients.

In aspects of this embodiment, a sunscreen soap composition disclosed herein comprises about 9% to about 21% of a cellulose encapsulate comprising about 45% to about 57% of homosalate, about 7% to about 19% of dibenzoylmethane and about 18% to about 30% of octyl salicylate, about 19% to about 31% petroleum and about 6% to about 18% of cocoa butter. In other aspects of this embodiment, a sunscreen soap composition disclosed herein comprises about 11% to about 19% of a cellulose encapsulate comprising about 47% to about 55% of homosalate, about 9% to about 17% of dibenzoylmethane and about 20% to about 28% of octyl salicylate, about 21% to about 29% of petroleum and about 8% to about 16% of cocoa butter. In yet other aspects of this embodiment, a sunscreen soap composition disclosed herein comprises about 12% to about 18% of a cellulose encapsulate comprising about 48% to about 54% of homosalate, about 10% to about 16% of dibenzoylmethane and about 21% to about 27% of octyl salicylate, about 22% to about 28% of petroleum and about 9% to about 15% of cocoa butter. In still other aspects of this embodiment, a sunscreen soap composition disclosed herein comprises about 14% to about 16% of a cellulose encapsulate comprising about 50% to about 52% of homosalate, about 12% to about 14% of dibenzoylmethane and about 23% to about 25% of octyl salicylate, about 24% to about 26% of petroleum and about 11% to about 13% of cocoa butter. In other aspects of this embodiment, a sunscreen soap composition disclosed herein comprises about 15% of a cellulose encapsulate comprising about 51% of homosalate, about 13% of dibenzoylmethane and about 24% of octyl salicylate, about 25% of petroleum and about 12% of cocoa butter.

In aspects of this embodiment, a sunscreen soap composition disclosed herein comprises about 9% to about 21% of a cellulose encapsulate comprising about 45% to about 57% of homosalate, about 7% to about 19% of avobenzone and about 18% to about 30% of octyl salicylate, about 19% to about 31% petroleum and about 6% to about 18% of cocoa butter. In other aspects of this embodiment, a sunscreen soap composition disclosed herein comprises about 11% to about 19% of a cellulose encapsulate comprising about 47% to about 55% of homosalate, about 9% to about 17% of avobenzone and about 20% to about 28% of octyl salicylate, about 21% to about 29% of petroleum and about 8% to about 16% of cocoa butter. In yet other aspects of this embodiment, a sunscreen soap composition disclosed herein comprises about 12% to about 18% of a cellulose encapsulate comprising about 48% to about 54% of homosalate, about 10% to about 16% of avobenzone and about 21% to about 27% of octyl salicylate, about 22% to about 28% of petroleum and about 9% to about 15% of cocoa butter. In still other aspects of this embodiment, a sunscreen soap composition disclosed herein comprises about 14% to about 16% of a cellulose encapsulate comprising about 50% to about 52% of homosalate, about 12% to about 14% of avobenzone and about 23% to about 25% of octyl salicylate, about 24% to about 26% of petroleum and about 11% to about 13% of cocoa butter. In other aspects of this embodiment, a sunscreen soap composition disclosed herein comprises about 15% of a cellulose encapsulate comprising about 51% of homosalate, about 13% of avobenzone and about 24% of octyl salicylate, about 25% of petroleum and about 12% of cocoa butter.

In another embodiment, a sunscreen lip balm composition disclosed herein comprises a cellulose encapsulate comprising a first UVB sunscreen active agent, a UVA sunscreen active agent, a second UVB sunscreen active agent and further comprises one or more photostabilizing agent. In aspects of this embodiment, the sunscreen lip balm composition disclosed herein comprises about 1% to about 12%, about 2% to about 10%, about 3% to about 9%, about 5% to about 7% or about 6% of a photostabilizing agent. In other aspects of this embodiment, the sunscreen lip balm composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen lip balm composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent. In still other aspects of this embodiment, the sunscreen lip balm composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent. In other aspects of this embodiment, the sunscreen lip balm composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen lip balm composition disclosed herein comprises a cellulose encapsulate comprising a broad spectrum UVA/UVB sunscreen active agent and a UVA sunscreen active agent, optionally one or more photostabilizing agent and/or film formers and further comprises one or more arachnid/insect repellents. In aspects of this embodiment, a sunscreen lip balm composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen lip balm composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR-3535, lemon eucalyptus oil, eucalyptus oil, peppermint oil, geranium oil and clove oil.

In an embodiment, a composition disclosed herein is a sunscreen soap composition. In aspects of this embodiment, a sunscreen soap composition disclosed herein comprises about 1% to about 12% of a cellulose encapsulate comprising about 50% to about 80% of a broad spectrum UVA/UVB sunscreen active agent and about 20% to about 50% of a UVA sunscreen active agent, about 1% to about 12% of a cellulose encapsulate comprising a UVB sunscreen active agent, about 0.1% to about 10% of a polyquaternium, and a soap base. In other aspects of this embodiment, a sunscreen soap composition disclosed herein comprises about 2% to about 10% of a cellulose encapsulate comprising about 55% to about 75% of a broad spectrum UVA/UVB sunscreen active agent and about 25% to about 45% of a UVA sunscreen active agent, about 2% to about 10% of a cellulose encapsulate comprising a UVB sunscreen active agent, about 0.25% to about 8% of a polyquaternium, and a soap base. In yet other aspects of this embodiment, a sunscreen soap composition disclosed herein comprises about 3% to about 9% of a cellulose encapsulate comprising about 60% to about 70% of a broad spectrum UVA/UVB sunscreen active agent and about 30% to about 40% of a UVA sunscreen active agent, about 3% to about 9% of a cellulose encapsulate comprising a UVB sunscreen active agent, about 0.5% to about 5% of a polyquaternium, and a soap base. In still other aspects of this embodiment, a sunscreen soap composition disclosed herein comprises about 5% to about 7% of a cellulose encapsulate comprising about 61% to about 66% of a broad spectrum UVA/UVB sunscreen active agent and about 33% to about 37% of a UVA sunscreen active agent, about 5% to about 7% of a cellulose encapsulate comprising a UVB sunscreen active agent, about 1% to about 3% of a polyquaternium, and a soap base. In other aspects of this embodiment, a sunscreen soap composition disclosed herein comprises about 6% of a cellulose encapsulate comprising about 65% of a broad spectrum UVA/UVB sunscreen active agent and about 35% of a UVA sunscreen active agent, about 6% of a cellulose encapsulate comprising a UVB sunscreen active agent, about 2% of a polyquaternium, and a soap base.

In aspects of this embodiment, a sunscreen soap composition disclosed herein comprises about 1% to about 12% of a cellulose encapsulate comprising about 50% to about 80% of an octocrylene and about 20% to about 50% of a dibenzoylmethane, about 1% to about 12% of a cellulose encapsulate comprising a cinnamate derivative, about 0.1% to about 10% of a polyquaternium, and a soap base. In other aspects of this embodiment, a sunscreen soap composition disclosed herein comprises about 2% to about 10% of a cellulose encapsulate comprising about 55% to about 75% of an octocrylene and about 25% to about 45% of a dibenzoylmethane, about 2% to about 10% of a cellulose encapsulate comprising a cinnamate derivative, about 0.25% to about 8% of a polyquaternium, and a soap base. In yet other aspects of this embodiment, a sunscreen soap composition disclosed herein about 3% to about 9% of a cellulose encapsulate comprising about 60% to about 70% of an octocrylene and about 30% to about 40% of a dibenzoylmethane, about 3% to about 9% of a cellulose encapsulate comprising a cinnamate derivative, about 0.5% to about 5% of a polyquaternium, and a soap base. In still other aspects of this embodiment, a sunscreen soap composition disclosed herein comprises about 5% to about 7% of a cellulose encapsulate comprising about 63% to about 68% of an octocrylene and about 33% to about 37% of a dibenzoylmethane, about 5% to about 7% of a cellulose encapsulate comprising a cinnamate derivative, about 1% to about 3% of a polyquaternium, and a soap base. In other aspects of this embodiment, a sunscreen soap composition disclosed herein comprises about 6% of a cellulose encapsulate comprising about 65% of an octocrylene and about 35% of a dibenzoylmethane, about 6% of a cellulose encapsulate comprising a cinnamate derivative, about 2% of a polyquaternium, and a soap base.

In aspects of this embodiment, a sunscreen soap composition disclosed herein comprises about 1% to about 12% of a cellulose encapsulate comprising about 50% to about 80% of an octocrylene and about 20% to about 50% of avobenzone, about 1% to about 12% of a cellulose encapsulate comprising octinoxate, about 0.1% to about 10% of a polyquaternium 16, and a soap base. In other aspects of this embodiment, a sunscreen soap composition disclosed herein comprises about 2% to about 10% of a cellulose encapsulate comprising about 55% to about 75% of an octocrylene and about 25% to about 45% of avobenzone, about 2% to about 10% of a cellulose encapsulate comprising octinoxate, about 0.25% to about 8% of a polyquaternium 16, and a soap base. In yet other aspects of this embodiment, a sunscreen soap composition disclosed herein comprises about 3% to about 9% of a cellulose encapsulate comprising about 60% to about 70% of an octocrylene and about 30% to about 40% of avobenzone, about 3% to about 9% of a cellulose encapsulate comprising octinoxate, about 0.5% to about 5% of a polyquaternium 16, and a soap base. In still other aspects of this embodiment, a sunscreen soap composition disclosed herein comprises about 5% to about 7% of a cellulose encapsulate comprising about 63% to about 68% of an octocrylene and about 33% to about 37% of avobenzone, about 5% to about 7% of a cellulose encapsulate comprising octinoxate, about 1% to about 3% of a polyquaternium 16, and a soap base. In other aspects of this embodiment, a sunscreen soap composition disclosed herein comprises about 6% of a cellulose encapsulate comprising about 65% of an octocrylene and about 35% of avobenzone, about 6% of a cellulose encapsulate comprising octinoxate, about 2% of a polyquaternium 16, and a soap base.

In another embodiment, a sunscreen soap composition disclosed herein comprises a cellulose encapsulate comprising a broad spectrum UVA/UVB sunscreen active agent and a UVA sunscreen active agent and further comprises a photostabilizing agent. In aspects of this embodiment, the sunscreen soap composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In aspects of this embodiment, the sunscreen soap composition disclosed herein comprises about 1% to about 12%, about 2% to about 10%, about 3% to about 9%, about 5% to about 7% or about 6% of a photostabilizing agent with a concomitant reduction in the amount of a broad spectrum UVA/UVB sunscreen active agent of equal value. In other aspects of this embodiment, the sunscreen soap composition disclosed herein comprises about 0.1% to about 8%, about 0.25% to about 6%, about 0.5% to about 4%, about 1% to about 3% or about 2% of a photostabilizing agent. In yet other aspects of this embodiment, the sunscreen soap composition disclosed herein comprises about 0.25% to about 8%, about 0.5% to about 6%, about 1% to about 5%, about 2% to about 4% or about 3% of a first photostabilizing agent and about 0.25% to about 8%, about 0.5% to about 6%, about 1% to about 5%, about 2% to about 4% or about 3% of a second photostabilizing agent with a concomitant reduction in the amount of a broad spectrum UVA/UVB sunscreen active agent of equal value. In still other aspects of this embodiment, the sunscreen soap composition disclosed herein comprises about 0.25% to about 5%, about 0.5% to about 3.5%, about 1% to about 3%, about 1.5% to about 2.5% or about 2% of a first photostabilizing agent, about 0.25% to about 5%, about 0.5% to about 3.5%, about 1% to about 3%, about 1.5% to about 2.5% or about 2% of a second photostabilizing agent and about 0.25% to about 5%, about 0.5% to about 3.5%, about 1% to about 3%, about 1.5% to about 2.5% or about 2% of a third photostabilizing agent with a concomitant reduction in the amount of a broad spectrum UVA/UVB sunscreen active agent of equal value. In other aspects of this embodiment, the sunscreen soap composition disclosed herein comprises trimethoxybenzylidene pentanedione (SYNOXYL® HSS), ethylhexyl methoxycrylene (SOLASTAY® 51) and/or a bis-methoxycrylene/octyldodecyl adipic acid/methylpropanediol copolymer (SOLASTAY® P1) as a photostabilizing agent.

In another embodiment, a sunscreen soap composition disclosed herein further comprises a film former. In aspects of this embodiment, a sunscreen soap composition disclosed herein comprises about 1% to about 6%, about 1.5% to about 4.5%, about 2% to about 4%, about 2.5% to about 3.5% or about 3% of a film former. In other aspects of this embodiment, the sunscreen soap composition disclosed herein comprises an acrylate copolymer as a film former. In yet other aspects of this embodiment, the sunscreen soap composition disclosed herein an acrylate copolymer is DERMACRYL® AQF.

In another embodiment, a sunscreen soap composition disclosed herein further comprises a film former as well as a cellulose encapsulate comprising a broad spectrum UVA/UVB sunscreen active agent and a UVA sunscreen active agent and further comprises a photostabilizing agent. In aspects of this embodiment, a sunscreen soap composition disclosed herein comprises about 0.25% to about 5%, about 0.5% to about 3.5%, about 1% to about 3%, about 1.5% to about 2.5% or about 2% of a photostabilizing agent with a concomitant reduction in the amount of a broad spectrum UVA/UVB sunscreen active agent of equal value. In other aspects of this embodiment, a sunscreen soap composition disclosed herein comprises trimethoxy benylidene pentanedione as a photostabilizing agent. In aspects of this embodiment, the sunscreen soap composition disclosed herein comprises about 1% to about 6%, about 1.5% to about 4.5%, about 2% to about 4%, about 2.5% to about 3.5% or about 3% of a film former. In other aspects of this embodiment, the sunscreen soap composition disclosed herein comprises an acrylate copolymer as a film former. In yet other aspects of this embodiment, the sunscreen soap composition disclosed herein an acrylate copolymer is DERMACRYL® AQF.

In another embodiment, a sunscreen soap composition disclosed herein comprises a cellulose encapsulate comprising a broad spectrum UVA/UVB sunscreen active agent and a UVA sunscreen active agent, optionally one or more photostabilizing agent and/or film formers and further comprises one or more cellulose encapsulates comprising one or more arachnid/insect repellents. In aspects of this embodiment, a sunscreen soap composition disclosed herein comprises one or more cellulose derived encapsulates comprising an arachnid/insect repellent comprise about 8% to about 20%, about 10% to about 18%, about 11% to about 17%, about 13% to about 15% or about 14% by weight of the total composition of a cellulose encapsulate comprising an arachnid/insect repellent. In other aspects of this embodiment, a sunscreen soap composition disclosed herein comprises one or more cellulose derived encapsulates comprising an arachnid/insect repellent comprise about 14% to about 26%, about 16% to about 24%, about 17% to about 23%, about 19% to about 21% or about 20% by weight of the total composition. In yet other aspects of this embodiment, the one or more cellulose encapsulates disclosed herein comprises about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent. In yet other aspects of this embodiment, the one or more cellulose encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent. In other aspects of this embodiment, an arachnid/insect repellent comprises DEET, IR-3535, lemon eucalyptus oil, eucalyptus oil, peppermint oil, geranium oil and clove oil.

In another embodiment, a sunscreen soap composition disclosed herein further comprises additional surfactants. In aspects of this embodiment, a sunscreen soap composition disclosed herein comprises about 20% to about 50% of additional surfactants. In aspects of this embodiment, additional surfactants include additional cationic surfactants, anionic surfactants, non-ionic surfactants, zwitterionic surfactants, amphoteric surfactants, or any combination thereof.

In aspects of this embodiment, a sunscreen soap composition disclosed herein comprises about 14% to about 26% of a cellulose encapsulate comprising about 40% to about 50% of a first arachnid/insect repellent and about 40% to about 50% of a second arachnid/insect repellent, about 1% to about 10% of a polymer, about 0.25% to about 8% of a film former and about 0.25% to about 8% fragrance. In other aspects of this embodiment, a sunscreen soap composition disclosed herein comprises about 16% to about 24% of a cellulose encapsulate comprising about 42% to about 50% of a first arachnid/insect repellent and about 42% to about 50% of a second arachnid/insect repellent, about 3% to about 9% of a polymer, about 0.5% to about 6% of a film former and about 0.5% to about 6% fragrance. In yet other aspects of this embodiment, a sunscreen soap composition disclosed herein comprises about 17% to about 23% of a cellulose encapsulate comprising about 44% to about 49% of a first arachnid/insect repellent and about 44% to about 49% of a second arachnid/insect repellent, about 4% to about 8% of a polymer, about 1% to about 5% of a film former and about 1% to about 5% fragrance. In still other aspects of this embodiment, a sunscreen soap composition disclosed herein comprises about 19% to about 21% of a cellulose encapsulate comprising about 46% to about 48% of a first arachnid/insect repellent and about 46% to about 48% of a second arachnid/insect repellent, about 5% to about 7% of a polymer, about 2% to about 4% of a film former and about 2% to about 4% fragrance. In other aspects of this embodiment, a sunscreen soap composition disclosed herein comprises about 20% of a cellulose encapsulate comprising about 47% of a first arachnid/insect repellent and about 47% of a second arachnid/insect repellent, about 6% of a polymer, about 3% of a film former and about 3% fragrance.

In aspects of this embodiment, a sunscreen soap composition disclosed herein comprises about 14% to about 26% of a cellulose encapsulate comprising about 40% to about 50% of lemon eucalyptus oil and about 40% to about 50% of IR-3535, about 1% to about 10% of a polymer, about 0.25% to about 8% of DERMACRYL® AQF and about 0.25% to about 8% fragrance. In other aspects of this embodiment, a sunscreen soap composition disclosed herein comprises about 16% to about 24% of a cellulose encapsulate comprising about 42% to about 50% of lemon eucalyptus oil and about 42% to about 50% of IR-3535, about 3% to about 9% of a polymer, about 0.5% to about 6% of DERMACRYL® AQF and about 0.5% to about 6% fragrance. In yet other aspects of this embodiment, a sunscreen soap composition disclosed herein comprises about 17% to about 23% of a cellulose encapsulate comprising about 44% to about 49% of lemon eucalyptus oil and about 44% to about 49% of IR-3535, about 4% to about 8% of a polymer, about 1% to about 5% of DERMACRYL® AQF and about 1% to about 5% fragrance. In still other aspects of this embodiment, a sunscreen soap composition disclosed herein comprises about 19% to about 21% of a cellulose encapsulate comprising about 46% to about 48% of lemon eucalyptus oil and about 46% to about 48% of IR-3535, about 5% to about 7% of a polymer, about 2% to about 4% of DERMACRYL® AQF and about 2% to about 4% fragrance. In other aspects of this embodiment, a sunscreen soap composition disclosed herein comprises about 20% of a cellulose encapsulate comprising about 47% of lemon eucalyptus oil and about 47% of IR-3535, about 6% of a polymer, about 3% of DERMACRYL® AQF and about 3% fragrance.

In aspects of this embodiment, a sunscreen soap composition disclosed herein comprises about 14% to about 26% of a cellulose encapsulate comprising about 88% to about 100% of an arachnid/insect repellent, about 1% to about 10% of a polymer, about 0.25% to about 8% of a film former and about 0.25% to about 8% fragrance. In other aspects of this embodiment, a sunscreen soap composition disclosed herein comprises about 16% to about 24% of a cellulose encapsulate comprising about 90% to about 98% of an arachnid/insect repellent, about 3% to about 9% of a polymer, about 0.5% to about 6% of a film former and about 0.5% to about 6% fragrance. In yet other aspects of this embodiment, a sunscreen soap composition disclosed herein comprises about 17% to about 23% of a cellulose encapsulate comprising about 91% to about 97% of an arachnid/insect repellent, about 4% to about 8% of a polymer, about 1% to about 5% of a film former and about 1% to about 5% fragrance. In still other aspects of this embodiment, a sunscreen soap composition disclosed herein comprises about 19% to about 21% of a cellulose encapsulate comprising about 93% to about 95% of an arachnid/insect repellent, about 5% to about 7% of a polymer, about 2% to about 4% of a film former and about 2% to about 4% fragrance. In other aspects of this embodiment, a sunscreen soap composition disclosed herein comprises about 20% of a cellulose encapsulate comprising about 94% of an arachnid/insect repellent, about 6% of a polymer, about 3% of a film former and about 3% fragrance.

In aspects of this embodiment, a sunscreen soap composition disclosed herein comprises about 14% to about 26% of a cellulose encapsulate comprising about 88% to about 100% of lemon eucalyptus oil, about 1% to about 10% of a polymer, about 0.25% to about 8% of DERMACRYL® AQF and about 0.25% to about 8% fragrance. In other aspects of this embodiment, a sunscreen soap composition disclosed herein comprises about 16% to about 24% of a cellulose encapsulate comprising about 90% to about 98% of lemon eucalyptus oil, about 3% to about 9% of a polymer, about 0.5% to about 6% of DERMACRYL® AQF and about 0.5% to about 6% fragrance. In yet other aspects of this embodiment, a sunscreen soap composition disclosed herein comprises about 17% to about 23% of a cellulose encapsulate comprising about 91% to about 97% of lemon eucalyptus oil, about 4% to about 8% of a polymer, about 1% to about 5% of DERMACRYL® AQF and about 1% to about 5% fragrance. In still other aspects of this embodiment, a sunscreen soap composition disclosed herein comprises about 19% to about 21% of a cellulose encapsulate comprising about 93% to about 95% of lemon eucalyptus oil, about 5% to about 7% of a polymer, about 2% to about 4% of DERMACRYL® AQF and about 2% to about 4% fragrance. In other aspects of this embodiment, a sunscreen soap composition disclosed herein comprises about 20% of a cellulose encapsulate comprising about 94% of lemon eucalyptus oil, about 6% of a polymer, about 3% of DERMACRYL® AQF and about 3% fragrance.

In aspects of this embodiment, a sunscreen soap composition disclosed herein comprises about 8% to about 20% of a cellulose encapsulate comprising about 88% to about 100% of an arachnid/insect repellent, about 14% to about 26% one or more plant oils, about 1% to about 10% of a polymer, about 0.25% to about 8% of a film former and about 0.1% to about 6% fragrance. In aspects of this embodiment, a sunscreen soap composition disclosed herein comprises about 10% to about 18% of a cellulose encapsulate comprising about 90% to about 98% of an arachnid/insect repellent, about 16% to about 24% one or more plant oils, about 3% to 9% of a polymer, about 0.5% to about 6% of a film former and about 0.2% to about 5% fragrance. In aspects of this embodiment, a sunscreen soap composition disclosed herein comprises about 11% to about 17% of a cellulose encapsulate comprising about 91% to about 97% of an arachnid/insect repellent, about 17% to about 23% one or more plant oils, about 4% to 8% of a polymer, about 1% to about 5% of a film former and about 0.3% to about 4% fragrance. In aspects of this embodiment, a sunscreen soap composition disclosed herein comprises about 13% to about 15% of a cellulose encapsulate comprising about 93% to about 95% of an arachnid/insect repellent, about 19% to about 21% one or more plant oils, about 5% to 7% of a polymer, about 2% to about 4% of a film former and about 0.5% to about 2% fragrance. In aspects of this embodiment, a sunscreen soap composition disclosed herein comprises about 14% of a cellulose encapsulate comprising about 94% of an arachnid/insect repellent, about 20% one or more plant oils, about 6% of a polymer, about 3% of a film former and about 1% fragrance.

In aspects of this embodiment, a sunscreen soap composition disclosed herein comprises about 8% to about 20% of a cellulose encapsulate comprising about 88% to about 100% of lemon eucalyptus oil, about 14% to about 26% geraniol, about 1% to 10% of a polymer, about 0.25% to about 8% of DERMACRYL® E and about 0.1% to about 6% fragrance. In aspects of this embodiment, a sunscreen soap composition disclosed herein comprises about 10% to about 18% of a cellulose encapsulate comprising about 90% to about 98% of lemon eucalyptus oil, about 16% to about 24% geraniol, about 3% to 9% of a polymer, about 0.5% to about 6% of DERMACRYL® E and about 0.2% to about 5% fragrance. In aspects of this embodiment, a sunscreen soap composition disclosed herein comprises about 11% to about 17% of a cellulose encapsulate comprising about 91% to about 97% of lemon eucalyptus oil, about 17% to about 23% geraniol, about 4% to 8% of a polymer, about 1% to about 5% of DERMACRYL® E and about 0.3% to about 4% fragrance. In aspects of this embodiment, a sunscreen soap composition disclosed herein comprises about 13% to about 15% of a cellulose encapsulate comprising about 93% to about 95% of lemon eucalyptus oil, about 19% to about 21% geraniol, about 5% to 7% of a polymer, about 2% to about 4% of DERMACRYL® E and about 0.5% to about 2% fragrance. In aspects of this embodiment, a sunscreen soap composition disclosed herein comprises about 14% of a cellulose encapsulate comprising about 94% of lemon eucalyptus oil, about 20% geraniol, about 6% of a polymer, about 3% of DERMACRYL® E and about 1% fragrance.

A composition disclosed herein is useful to provide protection against UV radiation, both naturally-occurring UV radiation and man-made UV radiation. In an embodiment, application of a composition disclosed herein can occur during washing in a suitable or effective amount, with application over part or the whole body. A shampoo or conditioner, gel, soap, hand sanitizer, cream, may be applied to hair, though in an embodiment, the shampoo combination product may be rinsed over part or the whole body, with a sunscreen composition adhering to the skin and hair. A selected amount of a combination product may be applied directly to the skin, for instance, without limitation, a lotion, spray or bodywash or may be used through intermediate application to a washcloth, pad, sponge, or other applicator. After lathering, dirt and sloughed-off skin may be washed away by rinsing with water leaving behind one or more of the sunscreen active agents, and in an embodiment, without limitation, a sunscreen active agent encapsulated in a cellulose derived capsule.

A composition disclosed herein is also useful in the treatment of a skin condition. A skin condition includes, without limitation, Seborrheic dermatitis, eczema, xerosis, infestation, dyschromia, keratosis pilaris, acne, anti-aging, sensitive skin, ephilidies, solar lentigines, photo sensitive disease, skin cancer, melisma, autoimmune disorder, alopecia, fungal, bacterial, and viral infections, protect colored or treated hair, bromhidrosis, malodor, dandruff, wound healing, arachnid/insect repellent, pet shampoo/skin care, lindane or similar conditions.

In an embodiment, sunscreen composition that is encapsulated in a cellulose derived capsule are used in paints. In a further embodiment, a paint including an encapsulated sunscreen composition includes one or more additional agents, including, without limitation, HALS.

In an embodiment, a sunscreen composition that is encapsulated in a cellulose derived capsule are used in products used by the military, police or other governmental or non-governmental force. In an embodiment, a product used by the by the military, police or other governmental or non-governmental force includes, without limitation, sunscreen, paint, clothes, weapons, including, without limitation, weapons containing composite or other synthetic parts, and other by the military, police or other governmental or non-governmental force products. In an embodiment, a sunscreen composition that is encapsulated in a cellulose derived capsule used for by the military, police or other governmental or non-governmental force includes a reflective agent and/or an agent capable of preventing the detection of infrared radiation by an individual or equipment.

A composition disclosed herein can be applied once per day, applied two, three, four or more times per day, applied every other day or applied about 10, 8, 7, 6, 5, 4, 3, 2 or 1 time per week. In aspects of this embodiment, the present invention discloses that a sunscreen can be applied to wet skin and/or hair or applied to dry skin and/or hair.

In an embodiment, methods for protection of skin from sunlight include, applying a combination product containing a sunscreen active agent disclosed herein, wherein after application of the combination product to an individual's outer surface, including, without limitation, an individual's skin, the skin is protected from sunlight with an average SPF of at least about 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more. In a further embodiment, the skin is protected from sunlight with an average SPF of at least about 2. In a further embodiment, the skin is protected from sunlight with an average SPF of at least about 5. In a further embodiment, the skin is protected from sunlight with an average SPF of at least about 10. In a further embodiment, the skin is protected from sunlight with an average SPF of at least about 15. In a further embodiment, the combination product is applied more than once; in these cases, the SPF may be cumulative and can increase with the second wash to, e.g., an average of more than 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more. In a further embodiment, the individual rinses off after application of a combination product, with the SPF following rinsing at least about 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more. In an additional embodiment, a combination product is applied once per day. In a further embodiment, a combination product is applied more than once per day, for example, 2, 3, 4, or more than 4 times per day. In an additional embodiment, a combination product is applied about every other day. In a further embodiment, the combination product is applied about 10, 8, 7, 6, 5, 4, 3, 2 or 1 time per week.

In an embodiment, a sunscreen composition has an inner refractive index of 1.5-1.7, 1.5-1.9, 1.5-2.2, 1.5-2.4 or 1.5-2.6. In a further embodiment, a sunscreen composition has a non-sunscreen active agent with an inner refractive index of 1.5-2.7. In a further embodiment, a sunscreen composition has a non-organic dispersed with organic sunscreen active agent with an inner refractive index of 1.5-2.7. In a further embodiment, a sunscreen composition has cellulose derived capsules of different sizes with an inner refractive index of 1.5-2.7. In a further embodiment, a sunscreen composition has a mixture of cellulose derived capsules containing different cellulose derivatives with an inner refractive index of 1.5-2.7. In an embodiment, a sunscreen composition has an overall refractive index of 1.4-2.

Aspects of the present specification can also be described as follows:

1. A sunscreen composition comprising, consisting essentially of or consisting of one or more flexible cellulose-derived encapsulates comprising, consisting essentially of or consisting of one or more sunscreen active agents and one or more photostabilizing agents.

2. The sunscreen composition of embodiment 1, wherein the one or more sunscreen active agents include a para-amino benzoate or derivative or salt thereof, a salicylate or derivative or salt thereof, a cinnamate or derivative or salt thereof, a benzophenone or derivative or salt thereof, an anthralinate or derivative or salt thereof, dibenzoylmethane or derivative or salt thereof, a camphor or derivative or salt thereof, a naphtholsulfonate or derivative or salt thereof, a coumarin or derivative or salt thereof, a diazole or derivative or salt thereof, a biphenyldisulfonate or derivative or salt thereof, a hydrocarbon or derivative or salt thereof, a quinolone or derivative or salt thereof, a quinine salt, a miscellaneous organic sunscreen active agent or any combination thereof.

3. The sunscreen composition of embodiments 1 or 2, wherein the one or more sunscreen active agents comprise one or more broad spectrum UVA/UVB sunscreen active agents, one or more UVA sunscreen active agents, one or more UVB sunscreen active agents, or any combination thereof.

4. The sunscreen composition of any one of embodiments 1-3, wherein the one or more sunscreen active agents comprise a broad spectrum UVA/UVB sunscreen active agent and a UVA sunscreen active agent or comprise a broad spectrum UVA/UVB sunscreen active agent, a UVA sunscreen active agent and a UVB sunscreen active agent or comprise a UVA sunscreen active agent and two different UVB sunscreen active agents.

5. The sunscreen composition of any one of embodiments 1-4, comprising, consisting essentially of or consisting of a first flexible cellulose-derived encapsulate comprising, consisting essentially of or consisting of one or more sunscreen active agents and one or more photostabilizing agents and a second flexible cellulose-derived encapsulate comprising, consisting essentially of or consisting of one or more sunscreen active agents and one or more photostabilizing agents.

6. The sunscreen composition of any one of embodiments 1-5, comprising, consisting essentially of or consisting of a first flexible cellulose-derived encapsulate comprising, consisting essentially of or consisting of one or more broad spectrum UVA/UVB sunscreen active agents, one or more UVA sunscreen active agents, one or more UVB sunscreen active agents, or any combination thereof.

7. The sunscreen composition of embodiment 6, wherein the first flexible cellulose-derived encapsulate comprises a broad spectrum UVA/UVB sunscreen active agent and a UVA sunscreen active agent or comprises a broad spectrum UVA/UVB sunscreen active agent, a UVA sunscreen active agent and a UVB sunscreen active agent or comprises a UVA sunscreen active agent and two different UVB sunscreen active agents.

8. The sunscreen composition of any one of embodiments 1-7, comprising, consisting essentially of or consisting of a second flexible cellulose-derived encapsulate comprising, consisting essentially of or consisting of one or more broad spectrum UVA/UVB sunscreen active agents, one or more UVA sunscreen active agents, one or more UVB sunscreen active agents, or any combination thereof.

9. The sunscreen composition of embodiment 8, wherein the second flexible cellulose-derived encapsulate comprises a broad spectrum UVA/UVB sunscreen active agent and a UVA sunscreen active agent or comprises a broad spectrum UVA/UVB sunscreen active agent, a UVA sunscreen active agent and a UVB sunscreen active agent or comprises a UVA sunscreen active agent and two different UVB sunscreen active agents.

10. The sunscreen composition of any one of embodiments 1-9, wherein the one or more cellulose derived encapsulates includes a cellulose derived encapsulate comprising, consisting essentially of or consisting of about 2% to about 14% by weight of the total composition of a cellulose derived encapsulate comprising, consisting essentially of or consisting of a UVB sunscreen active agent, about 4% to about 12% by weight of the total composition of a cellulose encapsulate comprising, consisting essentially of or consisting of a UVB sunscreen active agent, about 5% to about 11% by weight of the total composition of a cellulose encapsulate comprising, consisting essentially of or consisting of a UVB sunscreen active agent, about 7% to about 9% by weight of the total composition of a cellulose encapsulate comprising, consisting essentially of or consisting of a UVB sunscreen active agent or about 8% by weight of the total composition of a cellulose encapsulate comprising, consisting essentially of or consisting of a UVB sunscreen active agent.

11. The sunscreen composition of any one of embodiments 1-9, wherein the one or more cellulose derived encapsulates includes about 1% to about 12% by weight of the total composition of a cellulose derived encapsulate comprising, consisting essentially of or consisting of a UVB sunscreen active agent, about 2% to about 10% by weight of the total composition of a cellulose encapsulate comprising, consisting essentially of or consisting of a UVB sunscreen active agent, about 3% to about 9% by weight of the total composition of a cellulose encapsulate comprising, consisting essentially of or consisting of a UVB sunscreen active agent, about 5% to about 7% by weight of the total composition of a cellulose encapsulate comprising, consisting essentially of or consisting of a UVB sunscreen active agent or about 6% by weight of the total composition of a cellulose encapsulate comprising, consisting essentially of or consisting of a UVB sunscreen active agent.

12. The sunscreen composition of any one of embodiments 1-11, wherein the one or more cellulose derived encapsulates includes about 9% to about 21% by weight of the total composition of a cellulose encapsulate comprising, consisting essentially of or consisting of a first UVB sunscreen active agent, a UVA sunscreen active agent and a second UVB sunscreen active agent, about 11% to about 19% by weight of the total composition of a cellulose encapsulate comprising, consisting essentially of or consisting of a first UVB sunscreen active agent, a UVA sunscreen active agent and a second UVB sunscreen active agent, about 12% to about 18% by weight of the total composition of a cellulose encapsulate comprising, consisting essentially of or consisting of a first UVB sunscreen active agent, a UVA sunscreen active agent and a second UVB sunscreen active agent, about 14% to about 16% by weight of the total composition of a cellulose encapsulate comprising, consisting essentially of or consisting of a first UVB sunscreen active agent, a UVA sunscreen active agent and a second UVB sunscreen active agent or about 15% by weight of the total composition of a cellulose encapsulate comprising, consisting essentially of or consisting of a first UVB sunscreen active agent, a UVA sunscreen active agent and a second UVB sunscreen active agent.

13. The sunscreen composition of any one of embodiments 1-11, wherein the one or more cellulose derived encapsulates includes about 9% to about 21% by weight of the total composition of a cellulose encapsulate comprising, consisting essentially of or consisting of a broad spectrum UVA/UVB sunscreen active agent, a UVA sunscreen active agent and a UVB sunscreen active agent, about 11% to about 19% by weight of the total composition of a cellulose encapsulate comprising, consisting essentially of or consisting of a broad spectrum UVA/UVB sunscreen active agent, a UVA sunscreen active agent and a UVB sunscreen active agent, about 12% to about 18% by weight of the total composition of a cellulose encapsulate comprising, consisting essentially of or consisting of a broad spectrum UVA/UVB sunscreen active agent, a UVA sunscreen active agent and a UVB sunscreen active agent, about 14% to about 16% by weight of the total composition of a cellulose encapsulate comprising, consisting essentially of or consisting of a broad spectrum UVA/UVB sunscreen active agent, a UVA sunscreen active agent and a UVB sunscreen active agent, about 15% by weight of the total composition of a cellulose encapsulate comprising, consisting essentially of or consisting of a broad spectrum UVA/UVB sunscreen active agent or a UVA sunscreen active agent and a UVB sunscreen active agent.

14. The sunscreen composition of any one of embodiments 1-11, wherein the one or more cellulose derived encapsulates includes about 5% to about 17% by weight of the total composition of a cellulose encapsulate comprising, consisting essentially of or consisting of a broad spectrum UVA/UVB sunscreen active agent and a UVA sunscreen active agent, about 7% to about 15% by weight of the total composition of a cellulose encapsulate comprising, consisting essentially of or consisting of a broad spectrum UVA/UVB sunscreen active agent and a UVA sunscreen active agent, about 8% to about 14% by weight of the total composition of a cellulose encapsulate comprising, consisting essentially of or consisting of a broad spectrum UVA/UVB sunscreen active agent and a UVA sunscreen active agent, about 10% to about 12% by weight of the total composition of a cellulose encapsulate comprising, consisting essentially of or consisting of a broad spectrum UVA/UVB sunscreen active agent and a UVA sunscreen active agent or about 11% by weight of the total composition of a cellulose encapsulate comprising, consisting essentially of or consisting of a broad spectrum UVA/UVB sunscreen active agent and a UVA sunscreen active agent, 15. The sunscreen composition of any one of embodiments 1-11, wherein the one or more cellulose derived encapsulates includes about 2% to about 14% by weight of the total composition of a cellulose encapsulate comprising, consisting essentially of or consisting of a broad spectrum UVA/UVB sunscreen active agent and a UVA sunscreen active agent, about 4% to about 12% by weight of the total composition of a cellulose encapsulate comprising, consisting essentially of or consisting of a broad spectrum UVA/UVB sunscreen active agent and a UVA sunscreen active agent, about 5% to about 11% by weight of the total composition of a cellulose encapsulate comprising, consisting essentially of or consisting of a broad spectrum UVA/UVB sunscreen active agent and a UVA sunscreen active agent, about 7% to about 9% by weight of the total composition of a cellulose encapsulate comprising, consisting essentially of or consisting of a broad spectrum UVA/UVB sunscreen active agent and a UVA sunscreen active agent or about 8% by weight of the total composition of a cellulose encapsulate comprising, consisting essentially of or consisting of a broad spectrum UVA/UVB sunscreen active agent and a UVA sunscreen active agent.

16. The sunscreen composition of any one of embodiments 1-11, wherein the one or more cellulose derived encapsulates includes about 1% to about 12% by weight of the total composition of a cellulose encapsulate comprising, consisting essentially of or consisting of a broad spectrum UVA/UVB sunscreen active agent and a UVA sunscreen active agent, about 2% to about 10% by weight of the total composition of a cellulose encapsulate comprising, consisting essentially of or consisting of a broad spectrum UVA/UVB sunscreen active agent and a UVA sunscreen active agent, about 3% to about 9% by weight of the total composition of a cellulose encapsulate comprising, consisting essentially of or consisting of a broad spectrum UVA/UVB sunscreen active agent and a UVA sunscreen active agent, about 5% to about 7% by weight of the total composition of a cellulose encapsulate comprising, consisting essentially of or consisting of a broad spectrum UVA/UVB sunscreen active agent and a UVA sunscreen active agent or about 6% by weight of the total composition of a cellulose encapsulate comprising, consisting essentially of or consisting of a broad spectrum UVA/UVB sunscreen active agent and a UVA sunscreen active agent 17. The sunscreen composition of any one of embodiments 13-16, wherein the broad spectrum UVA/UVB sunscreen active agent is present in an amount of about 45% to about 57%, about 47% to about 55%, about 48% to about 54%, about 50% to about 52% or 51%.

18. The sunscreen composition of any one of embodiments 13-16, wherein the broad spectrum UVA/UVB sunscreen active agent is present in an amount of about 50% to about 80%, about 55% to about 75%, about 60% to about 70%, about 63% to about 68% or 65%.

19. The sunscreen composition of any one of embodiments 12-18, wherein the UVA sunscreen active agent is present in an amount of about 7% to about 19%, about 9% to about 17%, about 10% to about 16%, about 12% to about 14% or about 13%.

20. The sunscreen composition of any one of embodiments 12-18, wherein the UVA sunscreen active agent is present in an amount of about 20% to about 50%, about 25% to about 45%, about 30% to about 40%, about 33% to about 37% or about 35%.

21. The sunscreen composition of any one of embodiments 10-20, wherein the UVB sunscreen active agent is present in an amount of about 18% to about 30%, about 20% to about 28%, about 21% to about 27%, about 23% to about 25% or about 24%.

22. The sunscreen composition of any one of embodiments 3-9 or 13-18, wherein the broad spectrum UVA/UVB sunscreen active agent includes bemotrizinol (Tinosorb S), benzophenones 1-12, dioxybenzone, drometrizole trisiloxane (Mexoryl XL), Iscotrizinol (Uvasorb HEB), octocrylene, oxybenzone (Eusolex 4360), sulisobenzone, bisoctrizole (Tinosorb M), titanium dioxide, or zinc oxide.

23. The sunscreen composition of any one of embodiments 3-9, 12-16, 19, 20 or 22, wherein the UVA sunscreen active agent includes avobenzone (butyl methoxydibenzoylmethane or Parsol 1789), bisdisulizole disodium (Neo Heliopan AP), diethylamino hydroxybenzoyl hexyl benzoate (Uvinul A Plus), ecamsule (Mexoryl SX) or menthyl anthranilate, 24. The sunscreen composition of any one of embodiments 3-13 or 21-23, wherein the UVB sunscreen active agent includes amiloxate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), Padimate O (Escalol 507), phenylbenzimidazole sulfonic acid (Ensulizole), polysilicone-15 (Parsol SLX) or trolamine salicylate.

25. The sunscreen composition of any one of embodiments 1-24, wherein the one or more photostabilizing agents are present in an amount of about 0.25% to about 5%, about 0.5% to about 3.5%, about 1% to about 3%, about 1.5% to about 2.5% or about 2%.

26. The sunscreen composition of any one of embodiments 1-24, wherein the one or more photostabilizing agents are present in an amount of about 1% to about 12%, about 2% to about 10%, about 3% to about 9%, about 5% to about 7% or about 6%.

27. The sunscreen composition of any one of embodiments 1-24, wherein the one or more photostabilizing agents are present in an amount of about 0.1% to about 8%, about 0.25% to about 6%, about 0.5% to about 4%, about 1% to about 3% or about 2%.

28. The sunscreen composition of any one of embodiments 1-24, wherein the one or more photostabilizing agents are present in an amount of about 0.1% to about 8%, about 0.25% to about 6%, about 0.5% to about 4%, about 1% to about 3% or about 2%.

29. The sunscreen composition of any one of embodiments 1-24, wherein a first photostabilizing agent of the one or more photostabilizing agents is present in an amount of about 0.25% to about 5%, about 0.5% to about 3.5%, about 1% to about 3%, about 1.5% to about 2.5% or about 2%.

30. The sunscreen composition of any one of embodiments 1-24 or 29, wherein a second photostabilizing agent of the one or more photostabilizing agents is present in an amount of about 0.25% to about 5%, about 0.5% to about 3.5%, about 1% to about 3%, about 1.5% to about 2.5% or about 2%.
31. The sunscreen composition of any one of embodiments 1-24, 29 or 30, wherein a third photostabilizing agent of the one or more photostabilizing agents is present in an amount of about 0.25% to about 5%, about 0.5% to about 3.5%, about 1% to about 3%, about 1.5% to about 2.5% or about 2%.
32. The sunscreen composition of any one of embodiments 1-31, further comprising, consisting essentially of or consisting of one or more flexible cellulose-derived encapsulates comprising, consisting essentially of or consisting of one or more oils.
33. The sunscreen composition of embodiment 32, wherein the one or more oils are present in an amount of about 0.01% to about 7%, about 0.025% to about 5%, about 0.05% to about 2%, about 0.1% to about 1%, about 0.2% or about 0.15%.
34. The sunscreen composition of embodiment 32 or 33, wherein the one or more oils include a silicone oil, a shea oil or both.
35. The sunscreen composition of embodiment 34, wherein the silicone oil is present in an amount of about 0.01% to about 7%, about 0.025% to about 5%, about 0.05% to about 2%, about 0.1% to about 1%, about 0.2% or about 0.15%.
36. The sunscreen composition of embodiment 34 or 35, wherein the shea oil is present in an amount of about 0.01% to about 7%, about 0.025% to about 5%, about 0.05% to about 2%, about 0.1% to about 1%, about 0.2% or about 0.15%.
37. The sunscreen composition of any one of embodiments 1-35, further comprising, consisting essentially of or consisting of one or more emollients.
38. The sunscreen composition of embodiment 37, wherein the one or more emollients are present in an amount of about 0.25% to about 10%, about 0.5% to about 8%, about 1% to about 6%, about 2% to about 5% or about 3.4%.
39. The sunscreen composition of embodiment 37, wherein the one or more emollients are present in an amount of about 6% to about 18%, about 8% to about 16%, about 9% to about 15%, about 11% to about 13% or about 12% by weight of the total composition.
40. The sunscreen composition of any one of embodiment 37-39, wherein the one or more emollients includes a fatty acid, a fatty alcohol, an oil, an emollient ester, an emollient ether or any combination thereof.
41. The sunscreen composition of embodiment 40, wherein the fatty acids includes oleic acid or stearic acid.
42. The sunscreen composition of embodiment 40 or 41, wherein the fatty alcohol includes s-cetyl, or hexadecyl (ENJAY).
43. The sunscreen composition of any one of embodiments 40-42, wherein the emollient esters includes diisopropyl adipate, benzoic acid esters of $C_9$-$C_{15}$ alcohols, or isononyl iso-nonanoate.
44. The sunscreen composition of any one of embodiments 40-43, wherein the oil includes mineral oil, silicone oil, shea oil or cocoa butter.
45. The sunscreen composition of any one of embodiments 40-44, wherein the emollient ether includes a polyoxypropylene butyl ether or a polyoxypropylene cetyl ether.
46. The sunscreen composition of any one of embodiments 40-45, wherein the one or more emollients includes glycerine, cocoa butter, alovera, Vitamin A, Vitamin C, Vitamin D or capryllic capric triglyceride.
47. The sunscreen composition of any one of embodiments 1-46, further comprising, consisting essentially of or consisting of one or more thickening agents.
48. The sunscreen composition of embodiment 47, wherein the one or more thickening agents are present in an amount of about 0.5% to about 12%, about 1% to about 10%, about 1.5% to about 8.5%, about 2.5% to about 6.5% or about 4.5% by weight of the total composition.
49. The sunscreen composition of embodiment 47, wherein a first thickening agent of the one or more thickening agents is present in an amount of about 0.1% to about 9%, about 0.2% to about 7%, about 0.5% to about 5%, about 0.5% to about 3.5% or about 2% by weight of the total composition.
50. The sunscreen composition of embodiment 47 or 49, wherein a second thickening agent of the one or more thickening agents is present in an amount of about 0.1% to about 9%, about 0.2% to about 7%, about 0.5% to about 5%, about 0.5% to about 3.5% or about 2% by weight of the total composition.
51. The sunscreen composition of embodiment 47, wherein a first thickening agent of the one or more thickening agents is present in an amount of about 0.1% to about 9%, about 0.2% to about 7%, about 0.5% to about 5%, about 1% to about 4% or about 2.5% by weight of the total composition.
52. The sunscreen composition of any one of embodiments 47, 49 or 51, wherein a second thickening agent of the one or more thickening agents is present in an amount of about 0.1% to about 9%, about 0.2% to about 7%, about 0.5% to about 5%, about 1% to about 4% or about 2.5% by weight of the total composition.
53. The sunscreen composition of any one of embodiments 47-52, wherein one or more thickening agents comprise one or more silicone elastomer thickening agents, one or more sodium acrylate-sodium acryloyldimethyl taurate copolymer-based thickening agents, one or more polyacrylate-polyalkenyl ether polymer-based thickening agents (CARBOPOL™ 934, 971, 974, 980 or 981), one or more polyacrylate-divinyl glycol polymer-based thickening agents (NOVENN® AA1), one or more polyacrylate-methacrylate polymer-based thickening agents (PEMULEN™ TR-1 or TR-2), one or more polyacrylic acids, one or more humectants, propylene glycol or one or more essential plant oils.
54. The sunscreen composition of embodiment 53, wherein the one or more silicone elastomer thickening agents include a dimethicone-vinyldimethyl trimethylsiloxysilicate-dimethicone crosspolymer.
55. The sunscreen composition according to embodiment 53, wherein the one or more sodium acrylate-sodium acryloyldimethyl taurate copolymer-based thickening agents include an acrylate-sodium acryloyldimethyl taurate copolymer-based thickening agent comprising, consisting essentially of or consisting of isohexadecane and polysorbate 80.
56. The sunscreen composition according to embodiment 53, wherein the one or more humectants include glycerin, sorbitol, hexanetriol, propylene glycol, hexylene glycol, urea, guanidine, glycolic acid, D-panthenol, hyaluronic acid, lactamide monoethanolamine or acetamide monoethanolamine.
57. The sunscreen composition of any one of embodiments 1-24, further comprising, consisting essentially of or consisting of one or more film formers.
58. The sunscreen composition of embodiment 57, wherein the one or more film formers are present in an amount of about 1% to about 6%, about 1.5% to about 4.5%, about 2% to about 4%, about 2.5% to about 3.5%, about 3% or about 2.5% by weight of the total composition.
59. The sunscreen composition of embodiment 57, wherein the one or more film formers are present in an amount of about 0.25% to about 8%, about 0.5% to about 6%, about 1% to about 5%, about 2% to about 4% or about 3% by weight of the total composition.
60. The sunscreen composition of embodiment 57, wherein the one or more film formers are present in an amount of about 19% to about 31%, about 21% to about 29%, about 22% to about 28%, about 24% to about 26% or about 25% by weight of the total composition.
61. The sunscreen composition of any one of embodiments 58-60, wherein the one or more film formers include petroleum, an acrylate copolymer (DERMACRYL® 2.0, DERMACRYL® 79, DERMACRYL® AQF, DERMACRYL® C, DERMACRYL® E), a synthetic wax of branched polyalpha olefin polymers (PERFORMA® V 103, 260, 343, 825, 6038), a $C_{28}$-$C_{52}$ olefin/undecylenic acid copolymer (PERFORMA® V 6112) or MOISTUREGUARD™ (Engelhard), a film former comprising, consisting essentially of or consisting of petrolatum, dimethicone, stearamidopropyl dimethylamine, stearate and tocopheryl acetate.
62. The sunscreen composition of any one of embodiments 1-61, further comprising, consisting essentially of or consisting of one or more polyquaterniums.
63. The sunscreen composition of embodiment 62, wherein the one or more polyquaterniums are present in an amount of about 0.1% to about 10%, about 0.2% to about 8%, about 0.4% to about 6%, about 0.6% to about 5%, about 2.5% by weight of the total composition.
64. The sunscreen composition of embodiment 62, wherein the one or more polyquaterniums are present in an amount of about 0.1% to about 10%, about 0.25% to about 8%, about 0.5% to about 5%, about 1% to about 3% or about 2% by weight of the total composition.
65. The sunscreen composition of embodiment 62, wherein the one or more polyquaterniums are present in an amount of about 0.1% to about 7%, about 0.1% to about 5%, about 0.1% to about 3%, about 0.25% to about 2.5% or about 0.5% by weight of the total composition.
66. The sunscreen composition of any one of embodiments 62-65, wherein the one or more polyquaterniums polyquaternium-1, polyquaternium-2, polyquaternium-4 (CELQUAT L-200), polyquaternium-5, polyquaternium-6, polyquaternium-7, polyquaternium-10, polyquaternium-11, polyquaternium-15, polyquaternium-16, polyquaternium-22, polyquaternium-28, polyquaternium-32, polyquaternium-37, polyquaternium-39, polyquaternium-40, polyquaternium-41, polyquaternium-42, polyquaternium-44, polyquaternium-45, polyquaternium-46, polyquaternium-47, polyquaternium-64 or any combination thereof.
67. The sunscreen composition of any one of embodiments 1-66, further comprising, consisting essentially of or consisting of one or more surfactants.
68. The sunscreen composition of embodiment 67, wherein the one or more surfactant are present in an amount of about 0.1% to about 10%, about 0.25% to about 8%, about 0.5% to about 5%, about 1% to about 3%, about 1.6% by weight of the total composition.
69. The sunscreen composition of embodiment 67, wherein the one or more surfactant are present in an amount of about 3% to about 17%, about 5% to about 15%, about 7% to about 13%, about 9% to about 11% or about 10% by weight of the total composition.
70. The sunscreen composition of embodiment 67, wherein the one or more surfactant are present in an amount of about 2% to about 18%, about 3% to about 15%, about 4% to about 13%, about 5% to about 12% or about 6% to about 11% by weight of the total composition.
71. The sunscreen composition of embodiment 67, wherein the one or more surfactant are present in an amount of about 1% to about 20%, about 4% to about 14%, about 7% to about 11%, about 8% to about 10% or about 8.8% by weight of the total composition.
72. The sunscreen composition of any one of embodiments 67-71, wherein the one or more surfactants include one or more cationic surfactants, one or more anionic surfactants, one or more non-ionic surfactants, one or more zwitterionic surfactants, one or more amphoteric surfactants, or any combination thereof
73. The sunscreen composition of any one of embodiments 67-71, wherein the one or more surfactants include one or more anionic surfactants present in an amount of about 0.5% to about 15%, about 2% to about 12%, about 4% to about 10%, about 6% to about 8% or about 7% by weight of the total composition.
74. The sunscreen composition of any one of embodiments 67-71, wherein the one or more surfactants include one or more anionic surfactants present in an amount of about 1% to about 16%, about 1% to about 12%, about 3% to about 9%, about 5% to about 7% or about 5.6% by weight of the total composition.
75. The sunscreen composition of any one of embodiments 72-74, wherein the one or more anionic surfactants include one or more sulfated monoglyceride surfactants, one or more olefin sulfonate surfactants, one or more alkylbenzene sulfonate surfactants, one or more alkane sulfonate surfactants, one or more alkyl sulfosuccinate surfactants, one or more acyl isethionate surfactants or any combination thereof.
76. The sunscreen composition of embodiment 75, wherein the one or more alkyl sulfosuccinate surfactants include disodium N-octadecylsulfosuccinamate, diammonium lauryl sulfosuccinate, disodium laureth sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid and dioctyl esters of sodium sulfosuccinic acid; sodium dodecyl sulfate (or sodium lauryl sulfate), sodium laureth sulfate, ammonium lauryl sulfate, or any combination thereof.
77. The sunscreen composition of embodiment 75, wherein the one or more acyl isethionate surfactants include an alkylglyceryl ether sulfonate, a sodium cocoglyceryl ether sulfonate, a sulfonated fatty acid, a sulfonated methyl ester, an acyl glutamate, an alkanoyl sarcosinate, an alkyl ether carboxylate, an acyl lactylate, a carboxylate, a saponified soap, or any combination thereof.
78. The sunscreen composition of embodiment 75, wherein the one or more acyl isethionate surfactants ammonium cocoyl isethionate, sodium cocoyl isethionate, sodium lauroyl isethionate, sodium lauroyl sarcosinate, lauroyl sarcosine, sodium cocoyl sarcosinate, ammonium lauroyl sarcosinate, sodium laureth carboxylate, sodium cocoyl lactylate, sodium lauroyl carboxylate, sodium cocoyl carboxylate, ammonium lauroyl carboxylate, sodium laurate, sodium myristate, sodium palmitate, sodium stearate, sodium tallowate, cocoate or any combination thereof.
79. The sunscreen composition of any one of embodiments 67-72, wherein the one or more surfactants include one or more amphoteric surfactants present in an amount of about 0.1% to about 9%, about 0.25% to about 7%, about 0.5% to about 5%, about 2% to about 4%, about 3% by weight of the total composition.

80. The sunscreen composition of any one of embodiments 67-72, wherein the one or more surfactants include one or more amphoteric surfactants present in an amount of about 0.1% to about 5%, about 0.25% to about 4%, about 0.5% to about 3%, about 0.75% to about 2.5% or about 1% to about 2% by weight of the total composition.

81. The sunscreen composition of any one of embodiments 67-72, wherein the one or more surfactants include one or more amphoteric surfactants present in an amount of about 0.1% to about 10%, about 0.25% to about 8%, about 0.5% to about 5%, about 1% to about 3% or about 1.6% by weight of the total composition.

82. The sunscreen composition of any one of embodiments 79-81, wherein the one or more amphoteric surfactants include one or more betaines, one or more sultaines, one or more hydroxysultaines, one or more alkyliminoacetates, one or more iminodialkanoates, one or more aminoalkanoates or any combination thereof.

83. The sunscreen composition of any one of embodiments 79-81, wherein the one or more betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, oleyl betaine, cocamidopropyl betaine, an amidobetaine, an amidosulfobetaine or any combination thereof.

84. The sunscreen composition of any one of embodiments 67-72, wherein the one or more surfactants include one or more acyl taurate surfactants present in an amount of about 0.1% to about 5%, about 0.25% to about 4%, about 0.5% to about 3%, about 0.75% to about 2.5% or about 1% to about 2% by weight of the total composition.

85. The sunscreen composition of embodiment 84, wherein the one or more acyl taurate surfactants include sodium methyl cocoyl taurate and sodium methyl oleoyl taurate, taurine, a N-alkyltaurine or any combination thereof.

86. The sunscreen composition of any one of embodiments 1-85, further comprising, consisting essentially of or consisting of one or more flexible cellulose-derived encapsulates comprising, consisting essentially of or consisting of one or more arachnid/insect repellents.

87. The sunscreen composition of embodiment 86, wherein the one or more cellulose derived encapsulates comprising, consisting essentially of or consisting of one or more arachnid/insect repellent comprises about 8% to about 20%, about 10% to about 18%, about 11% to about 17%, about 13% to about 15% or about 14% by weight of the total composition.

88. The sunscreen composition of embodiment 86, wherein the one or more cellulose derived encapsulates comprising, consisting essentially of or consisting of one or more arachnid/insect repellent comprises about 14% to about 26%, about 16% to about 24%, about 17% to about 23%, about 19% to about 21% or about 20% by weight of the total composition.

89. The sunscreen composition of embodiment 86, wherein the one or more cellulose derived encapsulates comprising, consisting essentially of or consisting of a first arachnid/insect repellent and a second arachnid/insect repellent comprises about 14% to about 26%, about 16% to about 24%, about 17% to about 23%, about 19% to about 21% or about 20% by weight of the total composition.

90. The sunscreen composition of embodiment 87 or 88, wherein the arachnid/insect repellent is present in an amount of about 88% to about 100%, about 90% to about 98%, about 91% to about 97%, about 93% to about 95% or about 94%.

91. The sunscreen composition of embodiment 87 or 88, wherein the arachnid/insect repellent is present in an amount of about 40% to about 54%, about 42% to about 52%, about 44% to about 50%, about 46% to about 48% or about 47%.

92. The sunscreen composition of embodiment 89, wherein the first arachnid/insect repellent is present in an amount of about 40% to about 50%, about 42% to about 50%, about 44% to about 49%, about 46% to about 48% or about 47%.

93. The sunscreen composition of embodiment 89 or 92, wherein the second arachnid/insect repellent is present in an amount of about 40% to about 50%, about 42% to about 50%, about 44% to about 49%, about 46% to about 48% or about 47%.

94. The sunscreen composition of embodiment 89, wherein the first arachnid/insect repellent is present in an amount of about 17% to about 30%, about 19% to about 28%, about 21% to about 26%, about 23% to about 24% or about 23.5%.

95. The sunscreen composition of any one of embodiments 89, 92 or 94, wherein the first arachnid/insect repellent is present in an amount of about 17% to about 30%, about 19% to about 28%, about 21% to about 26%, about 23% to about 24% or about 23.5%.

96. The sunscreen composition of any one of embodiments 86-95, wherein the first arachnid/insect repellent includes DEET, IR3535, lemon eucalyptus oil, eucalyptus oil, peppermint oil, geranium oil and clove oil.

97. The sunscreen composition of any one of embodiments 1-96, further comprising, consisting essentially of or consisting of one or more polymers.

98. The sunscreen composition of embodiment 97, wherein the one or more polymers are present in an amount of about 1% to about 10%, about 3% to about 9%, about 4% to about 8%, about 5% to about 7% or about 6% by weight of the total composition.

99. The sunscreen composition of any one of embodiments 1-98, further comprising, consisting essentially of or consisting of one or more fragrances.

100. The sunscreen composition of embodiment 99, wherein the one or more fragrances are present in an amount of about 0.25% to about 8%, about 0.5% to about 6%, about 1% to about 5%, about 2% to about 4% or about 3% by weight of the total composition.

101. The sunscreen composition of embodiment 99, wherein the one or more fragrances are present in an amount of about 0.1% to about 6%, about 0.2% to about 5%, about 0.3% to about 4%, about 0.5% to about 2% or about 1% by weight of the total composition.

102. The sunscreen composition of any one of embodiments 1-101, further comprising, consisting essentially of or consisting of one or more plant oils.

103. The sunscreen composition of embodiment 102, wherein the one or more plant oils are present in an amount of about 14% to about 26%, about 16% to about 24%, about 17% to about 23%, about 19% to about 21% or about 20% by weight of the total composition.
104. The sunscreen composition of any one of embodiments 1-103, wherein the SPF value is at least 35.
105. The sunscreen composition of any one of embodiments 1-104, wherein the sunscreen composition is a body wash, an after shower body lotion, a shampoo, a conditioner, a soap, a gel, a hand sanitizer, a cream, a spray, a mouse, a lotion, an ointment, a make-up product, a lip balm, a hair spray product, an arachnid/insect repellent or a medicinal product.

Aspects of the present specification can also be described as follows:

1. A sunscreen lotion composition comprises: about 0.01% to about 7% by total weight of the composition of a first cellulose encapsulate comprising, consisting essentially of or consisting of a silicone oil, about 0.01% to about 7% by total weight of the composition of a second cellulose encapsulate comprising, consisting essentially of or consisting of a shea oil, about 5% to about 17% by total weight of the composition of a third cellulose encapsulate comprising, consisting essentially of or consisting of about 50% to about 80% of a broad spectrum UVA/UVB sunscreen active agent, about 20% to about 50% of a UVA sunscreen active agent and about 0.25% to about 5% by total weight of the composition of a photostabilizing agent, about 2% to about 14% by total weight of the composition of a fourth cellulose encapsulate comprising, consisting essentially of or consisting of a UVB sunscreen active agent, about 0.25% to about 10% by total weight of the composition of one or more emollients and about 0.5% to about 12% by total weight of the composition of one or more thickening agents.
2. The sunscreen lotion composition according to embodiment 1, wherein the amount of the first cellulose encapsulate is about 0.025% to about 5% by total weight of the composition.
3. The sunscreen lotion composition according to embodiment 2, wherein the amount of the first cellulose encapsulate is about 0.05% to about 2% by total weight of the composition.
4. The sunscreen lotion composition according to embodiment 3, wherein the amount of the first cellulose encapsulate is about 0.1% to about 1% by total weight of the composition.
5. The sunscreen lotion composition according to any one of embodiments 1-4, wherein the amount of the second cellulose encapsulate is about 0.025% to about 5% by total weight of the composition.
6. The sunscreen lotion composition according to embodiment 5, wherein the amount of the second cellulose encapsulate is about 0.5% to about 2% by total weight of the composition.
7. The sunscreen lotion composition according to embodiment 6, wherein the amount of the second cellulose encapsulate is about 0.1% to about 1% by total weight of the composition.
8. The sunscreen lotion composition according to any one of embodiments 1-7, wherein the amount of the third cellulose encapsulate is about 7% to about 15% by total weight of the composition.
9. The sunscreen lotion composition according to embodiment 8, wherein the amount of the third cellulose encapsulate is about 8% to about 14% by total weight of the composition.
10. The sunscreen lotion composition according to embodiment 9, wherein the amount of the third cellulose encapsulate is about 10% to about 12% by total weight of the composition.
11. The sunscreen lotion composition according to any one of embodiments 1-10, wherein the amount of the fourth cellulose encapsulate is about 4% to about 12% by total weight of the composition.
12. The sunscreen lotion composition according to embodiment 11, wherein the amount of the fourth cellulose encapsulate is about 5% to about 11% by total weight of the composition.
13. The sunscreen lotion composition according to embodiment 12, wherein the amount of the fourth cellulose encapsulate is about 7% to about 9% by total weight of the composition.
14. The sunscreen lotion composition according to any one of embodiments 1-13, wherein the broad spectrum UVA/UVB sunscreen active agent is an octocrylene.
15. The sunscreen lotion composition according to any one of embodiments 1-14, wherein the UVA sunscreen active agent is a dibenzoylmethane.
16. The sunscreen lotion composition according to embodiment 15, wherein the dibenzoylmethane includes avobenzone.
17. The sunscreen lotion composition according to any one of embodiments 1-16, wherein the UVA sunscreen active agent is a cinnamate derivative.
18. The sunscreen lotion composition according to embodiment 17, wherein the cinnamate derivative includes octinoxate
19. The sunscreen lotion composition according to any one of embodiments 1-18, wherein the photostabilizing agent includes trimethoxy benylidene pentanedione.
20. The sunscreen lotion composition according to any one of embodiments 1-19, wherein the third cellulose encapsulate comprises about 55% to about 75% of a broad spectrum UVA/UVB sunscreen active agent, about 25% to about 45% of a UVA sunscreen active agent and about 0.5% to about 3.5% by total weight of the composition of a photostabilizing agent.
21. The sunscreen lotion composition according to embodiment 20, wherein the third cellulose encapsulate comprises about 60% to about 70% of a broad spectrum UVA/UVB sunscreen active agent, about 40% to about 40% of a UVA sunscreen active agent and about 1% to about 3% by total weight of the composition of a photostabilizing agent.
22. The sunscreen lotion composition according to embodiment 21, wherein the third cellulose encapsulate comprises about 63% to about 68% of a broad spectrum UVA/UVB sunscreen active agent, about 33% to about 37% of a UVA sunscreen active agent and about 1.5% to about 2.5% by total weight of the composition of a photostabilizing agent.
23. The sunscreen lotion composition according to any one of embodiments 1-22, wherein the one or more emollients comprise capryllic capric triglyceride.
24. The sunscreen lotion composition according to any one of embodiments 1-23, wherein the thickening agents comprise one or more silicone elastomer thickening agents and one or more sodium acrylate-sodium acryloyldimethyl taurate copolymer-based thickening agents.
25. The sunscreen lotion composition according to embodiment 24, wherein the one or more silicone elastomer thickening agents include a dimethicone-vinyldimethyl trimethylsiloxysilicate-dimethicone crosspolymer.

26. The sunscreen lotion composition according to embodiment 24, wherein the one or more sodium acrylate-sodium acryloyldimethyl taurate copolymer-based thickening agents include an acrylate-sodium acryloyldimethyl taurate copolymer-based thickening agent comprising, consisting essentially of or consisting of isohexadecane and polysorbate 80.

27. The sunscreen lotion composition according to any one of embodiments 1-26, further comprising, consisting essentially of or consisting of a film former.

28. The sunscreen lotion composition according to embodiment 27, wherein the film former is in an amount of about 1% to about 6% by total weight of the composition.

29. The sunscreen lotion composition according to embodiment 27, wherein the film former includes an acrylate copolymer.

30. The sunscreen lotion composition according to any one of embodiments 1-29, wherein the SPF value is at least 35.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the sunscreen compositions, methods or uses pertaining to sunscreen compositions.

Example 1: SPF Testing of Sunscreen Body Wash Compositions

Sunscreen body wash compositions disclosed herein were tested to determine their SPF value using the static, rinse/lather/rinse/rub and/or water immersion (40 or 80 minute) assays using the methods described in FDA Final Monograph, "Labelling and Effectiveness Testing; Sunscreen Drug Products for Over-the Counter Human Use", Final Rule, 21 C.F.R. §§ 201 and 310. To conduct this test, a 50 cm² square area on the back of an individual (application site) was wetted with 10 mL of water delivered with a syringe. The test sunscreen composition was then applied to the application site in amounts as specified in the FDA monograph. To perform the static assay, the applied composition was allowed to dry for 15 minutes and then exposed to a fixed dose of UV radiation having a continuous emission spectrum from 290 nm to 400 nm with a limit of 1,500 W/m² using a solar simulator as specified in the FDA monograph. To perform the rinse/lather/rinse/rub assay, the applied composition was worked into a lather for two minutes and then the application site was rinsed for two minutes with 20 mL water, pat dried and then rubbed using moderate pressure for 20 seconds. The application site was then exposed to a fixed dose of UV radiation having a continuous emission spectrum from 290 nm to 400 nm with a limit of 1,500 W/m² using a solar simulator as specified in the FDA monograph. To perform the water immersion assay, the applied composition was allowed to dry for 15 minutes and then the application site immersed into a whirlpool bath for either 40 or 80 minutes. The application site was then exposed to a fixed dose of UV radiation having a continuous emission spectrum from 290 nm to 400 nm with a limit of 1,500 W/m² using a solar simulator as specified in the FDA monograph.

Table 1 shows the test results of a sunscreen body wash composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquaternium, and one or more surfactants. In particular, a sunscreen body wash composition comprising about 11% of a cellulose encapsulate including a mixture of about 65% of an octocrylene and about 35% of avobenzone, about 8% of a cellulose encapsulate comprising octinoxate, about 2.5% of a polyquaternium, 10, about 3.5% sodium laureth sulfate, about 3.5% sodium lauryl sulfate and about 2.8% cocamido propylbetaine was tested. The results indicate that the disclosed sunscreen body wash composition had an average SPF value of 38.07 based on the static assay (Table 1). Interestingly, even after the rinse/lather/rinse/rub assay the average SPF value was still over 33 which represents only a 13% loss in SPF protection after a modified applied water method (Table 1).

TABLE 1

Evaluation of Sunscreen Body Wash Composition by SPF Determination (FDA) - Static and Rinse/Lather/Rinse/Rub Assays

| Subject No. | Gender | MED[b]/Hr | I[a] (Amps) | Skin Type | MED I (J/m²) | MED II (J/m²) | STD[c] | SPF Values Static | RLR/RUB[d] |
|---|---|---|---|---|---|---|---|---|---|
| 62-0539 | F | 127.3 | 6.0 | I | 30.33 | 30.33 | 16.30 | 39.60 | 34.50 |
| 48-9212 | F | 129.2 | 6.0 | II | 46.20 | 46.20 | 18.75 | 39.60 | 34.50 |
| 78-4159 | M | 127.1 | 6.0 | II | 46.20 | 46.20 | 16.30 | 34.50 | 30.00 |
| 78-4237 | M | 128.4 | 6.0 | II | 46.20 | 46.20 | 18.75 | 39.60 | 34.50 |
| 72-7479 | M | 128.1 | 6.0 | II | 46.20 | 46.20 | 18.75 | 34.50 | 30.00 |
| 76-0164 | M | 125.9 | 6.0 | II | 46.20 | 46.20 | 18.75 | 39.60 | 34.50 |
| 54-1578 | F | 127.1 | 5.4 | II | 46.20 | 46.20 | 16.30 | 39.60 | 34.50 |
| 58-3948 | M | 128.4 | 6.0 | II | 46.20 | 46.20 | 16.30 | 34.50 | 30.00 |
| 70-8402 | F | 126.9 | 5.9 | III | 46.20 | 46.20 | 18.75 | 39.60 | 34.50 |
| 56-5529 | F | 125.4 | 6.0 | II | 30.33 | 30.33 | 16.30 | 39.60 | 34.50 |
| Mean (x) | | | | | | | 17.53 | 38.07 | 33.15 |
| Standard Deviation(s) | | | | | | | 1.29 | 2.46 | 2.17 |
| Standard Error | | | | | | | 0.41 | 0.78 | 0.69 |
| Standard Error % of Mean | | | | | | | 2.34 | 2.05 | 2.08 |
| N | | | | | | | 10 | 10 | 10 |

TABLE 1-continued

Evaluation of Sunscreen Body Wash Composition by SPF Determination
(FDA) - Static and Rinse/Lather/Rinse/Rub Assays

| Subject | | $I^a$ | Skin | MED I | MED II | | SPF Values | |
|---|---|---|---|---|---|---|---|---|
| No. | Gender | $MED^b/Hr$ (Amps) | Type | $(J/m^2)$ | $(J/m^2)$ | $STD^c$ | Static | $RLR/RUB^d$ |
| | | Upper 5% t Dist. | | | | 2.2622 | 1.8331 | 1.8331 |
| | | A Values | | | | 0.9228 | 1.4260 | 1.2579 |
| | | Label SPF | | | | 16 | 36 | 31 |

[a] I is Intensity of Light Source.
[b] MED is Minimal Erythemal Dose: 1 MED = 200 $J/m^2$ -eff.
[c] 7% PadO/3% Oxyb.
[d] Rinse/Lather/Rinse/Rub assay.

Tables 2 and 3 show similar results. The sunscreen body wash compositions exhibited an average SPF value of 34.5 based on the static assay (Tables 2 and 3). However, even after an 80 water immersion assay, the UV radiation protective capabilities of these compositions were still maintained to an average SPF value of 34.5 (Table 2) and 32.25 (Tables 2 and 3). These results show that the disclose sunscreen body wash compositions demonstrate a significant increase in UV radiation protection and very good water resistant properties.

encapsulate comprising a UVB sunscreen active agent, a polyquaternium, and one or more surfactants. In particular, a sunscreen body wash composition comprising about 11% of a cellulose encapsulate including about 65% of an octocrylene and about 35% of avobenzone, about 8% of a cellulose encapsulate comprising octinoxate, about 2.5% of a polyquaternium, 10, about 4% disodium laureth sulfosuccinate, about 1.6% sodium cocoyl isethionate, about 1.6% cocamidopropyl betaine and about 1.6% sodium methyl cocoyl taurate was tested. The results indicate that the

TABLE 2

Evaluation of Sunscreen Body Wash Composition by SPF Determination
(FDA) - Static and 80 Minute Water Immersion Assays

| Subject | | | $I^a$ | Skin | MED I | MED II | | WR | SPF Values | |
|---|---|---|---|---|---|---|---|---|---|---|
| No. | Gender | $MED^b/Hr$ | (Amps) | Type | $(J/m^2)$ | $(J/m^2)$ | $STD^c$ | Control | Static | $WR^d$ |
| 78-4159 | M | 127.1 | 6.0 | II | 46.20 | 46.20 | 16.30 | 15.00 | 34.50 | 34.50 |
| 72-7479 | M | 128.1 | 6.0 | II | 46.20 | 46.20 | 18.75 | 18.00 | 34.50 | 34.50 |
| | | Mean (x) | | | | | 17.53 | 16.50 | 34.50 | 34.50 |
| | | Standard Deviation(s) | | | | | 1.73 | 2.12 | 0.00 | 0.00 |
| | | Standard Error | | | | | 1.23 | 1.50 | 0.00 | 0.00 |
| | | Standard Error % of Mean | | | | | 7.02 | 9.09 | 0.00 | 0.00 |
| | | N | | | | | 2 | 2 | 2 | 2 |

[a] I is Intensity of Light Source.
[b] MED is Minimal Erythemal Dose: 1 MED = 200 $J/m^2$ -eff.
[c] 7% PadO/3% Oxyb.
[d] Water Resistance based on water immersion assay.

TABLE 3

Evaluation of Sunscreen Body Wash Composition by SPF Determination (FDA) -
Static and 80 Minute Water Immersion Assays

| Subject | | | $I^a$ | Skin | MED I | MED II | | WR | SPF Values | |
|---|---|---|---|---|---|---|---|---|---|---|
| No. | Gender | $MED^b/Hr$ | (Amps) | Type | $(J/m^2)$ | $(J/m^2)$ | $STD^c$ | Control | Static | $WR^d$ |
| 78-4159 | M | 126.7 | 5.8 | II | 46.20 | 46.20 | 16.30 | 18.00 | 34.50 | 34.50 |
| 48-1671 | F | 126.2 | 6.0 | II | 30.33 | 30.33 | 18.75 | 15.00 | 34.50 | 30.00 |
| | | Mean (x) | | | | | 17.53 | 16.50 | 34.50 | 32.25 |
| | | Standard Deviation(s) | | | | | 1.73 | 2.12 | 0.00 | 3.18 |
| | | Standard Error | | | | | 1.23 | 1.50 | 0.00 | 2.25 |
| | | Standard Error % of Mean | | | | | 7.02 | 9.09 | 0.00 | 6.98 |
| | | N | | | | | 2 | 2 | 2 | 2 |

[a] I is Intensity of Light Source.
[b] MED is Minimal Erythemal Dose: 1 MED = 200 $J/m^2$-eff.
[c] 7% PadO/3% Oxyb.
[d] Water Resistance based on water immersion assay.

Table 4 shows the test results of a sunscreen body wash composition disclosed herein comprises a cellulose encapsulate comprising a broad spectrum UVA/UVB sunscreen active agent and a UVA sunscreen active agent, a cellulose disclosed sunscreen body wash composition had an average SPF value of 36.54 based on the static assay (Table 4). Interestingly, even after the rinse/lather/rinse/rub assay the average SPF value was still over 33 (Table 4).

TABLE 4

Evaluation of Sunscreen Body Wash Composition by SPF Determination (FDA) - Static and Rinse/Lather/Rinse/Rub Assays

| Subject No. | Gender | MED[b]/Hr | I[a] (Amps) | Skin Type | MED I (J/m$^2$) | MED II (J/m$^2$) | STD[c] | SPF Values Static | SPF Values RLR/RUB[d] |
|---|---|---|---|---|---|---|---|---|---|
| 62-0539 | F | 127.3 | 6.0 | I | 30.33 | 30.33 | 16.30 | 34.50 | 34.50 |
| 48-9212 | F | 129.2 | 6.0 | II | 46.20 | 46.20 | 18.75 | 34.50 | 34.50 |
| 78-4159 | M | 127.1 | 6.0 | II | 46.20 | 46.20 | 16.30 | 34.50 | 30.00 |
| 78-4237 | M | 128.4 | 6.0 | II | 46.20 | 46.20 | 18.75 | 39.60 | 34.50 |
| 72-7479 | M | 128.1 | 6.0 | II | 46.20 | 46.20 | 18.75 | 34.50 | 34.50 |
| 76-0164 | M | 125.9 | 6.0 | II | 46.20 | 46.20 | 18.75 | 39.50 | 34.50 |
| 54-1578 | F | 127.1 | 5.4 | II | 46.20 | 46.20 | 16.30 | 34.50 | 34.50 |
| 58-3948 | M | 128.4 | 6.0 | II | 46.20 | 46.20 | 16.30 | 34.50 | 30.00 |
| 70-8402 | F | 126.9 | 5.9 | III | 46.20 | 46.20 | 18.75 | 39.60 | 34.50 |
| 56-5529 | F | 125.4 | 6.0 | II | 30.33 | 30.33 | 16.30 | 39.60 | 34.50 |
| Mean (x) | | | | | | | 17.53 | 36.54 | 33.60 |
| Standard Deviation(s) | | | | | | | 1.29 | 2.63 | 1.90 |
| Standard Error | | | | | | | 0.41 | 0.83 | 0.60 |
| Standard Error % of Mean | | | | | | | 2.34 | 2.27 | 1.79 |
| N | | | | | | | 10 | 10 | 10 |
| Upper 5% t Dist. | | | | | | | 2.2622 | 1.8331 | 1.8331 |
| A Values | | | | | | | 0.9228 | 1.5246 | 1.1014 |
| Label SPF | | | | | | | 16 | 35 | 32 |

[a]I is Intensity of Light Source.
[b]MED is Minimal Erythemal Dose: 1 MED = 200 J/m$^2$-eff.
[c]7% PadO/3% Oxyb.
[d]Rinse/Lather/Rinse/Rub assay.

Tables 5 and 6 show similar results. The sunscreen body wash compositions exhibited an average SPF value of 34.5 based on the static assay (Tables 5 and 6). However, even after an 80 water immersion assay, the UV radiation protective capabilities of these compositions were still maintained to an average SPF value of 30.0 (Table 5 and 6). These results show that the disclose sunscreen body wash compositions demonstrate very water resistant properties.

TABLE 5

Evaluation of Sunscreen Body Wash Composition by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | SPF Values WR[d] |
|---|---|---|---|---|---|---|---|---|---|---|
| 78-4159 | M | 127.1 | 6.0 | II | 46.20 | 46.20 | 16.30 | 15.00 | 34.50 | 30.00 |
| 72-7479 | M | 128.1 | 6.0 | II | 46.20 | 46.20 | 18.75 | 18.00 | 34.50 | 30.00 |
| Mean (x) | | | | | | | 17.53 | 16.50 | 34.50 | 30.00 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a]I is Intensity of Light Source.
[b]MED is Minimal Erythemal Dose: 1 MED = 200 J/m$^2$-eff.
[c]7% PadO/3% Oxyb.
[d]Water Resistance based on water immersion assay.

TABLE 6

Evaluation of Sunscreen Body Wash Composition by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | SPF Values WR[d] |
|---|---|---|---|---|---|---|---|---|---|---|
| 78-4159 | M | 126.7 | 5.8 | II | 46.20 | 46.20 | 16.30 | 18.00 | 34.50 | 30.00 |
| 48-1671 | F | 126.2 | 6.0 | II | 30.33 | 30.33 | 18.75 | 15.00 | 34.50 | 30.00 |
| Mean (x) | | | | | | | 17.53 | 16.50 | 34.50 | 30.00 |
| Standard Deviation(s) | | | | | | | 1.73 | 2.12 | 0.00 | 0.00 |

TABLE 6-continued

Evaluation of Sunscreen Body Wash Composition by SPF Determination (FDA) - Static and 80 Minute Water Immersion Assays

| Subject | | | | | | | | | SPF Values | |
|---|---|---|---|---|---|---|---|---|---|---|
| No. | Gender | MED[b]/Hr | I[a] (Amps) | Skin Type | MED I (J/m²) | MED II (J/m²) | STD[c] | WR Control | Static | WR[d] |
| | | Standard Error | | | | | 1.23 | 1.50 | 0.00 | 0.00 |
| | | Standard Error % of Mean | | | | | 7.02 | 9.09 | 0.00 | 0.00 |
| | | N | | | | | 2 | 2 | 2 | 2 |

[a] I is Intensity of Light Source.
[b] MED is Minimal Erythemal Dose: 1 MED = 200 J/m²-eff.
[c] 7% PadO/3% Oxyb.
[d] Water Resistance based on water immersion assay.

Example 2: SPF Testing of Sunscreen Lotion Compositions

Sunscreen lotion compositions disclosed herein were tested to determine their SPF value using the static and water immersion (40 or 80 minute) assays as described in Example 1.

Experiments were conducted with a sunscreen lotion composition comprising a photostabilizing agent. Table 7 shows the test results of a sunscreen lotion composition disclosed herein comprises a cellulose encapsulate comprising a broad spectrum UVA/UVB sunscreen active agent, a UVA sunscreen active agent and a photostabilizing agent, a cellulose encapsulate comprising a UVB sunscreen active agent, a cellulose encapsulate comprising a silicone oil, a cellulose encapsulate comprising a comprising a shea oil, one or more emollients and one or more thickening agents. In particular, a sunscreen lotion composition comprising about 0.15% of a cellulose encapsulate comprising a silicone oil, about 0.2% of a cellulose encapsulate comprising a shea oil, about 11% of a cellulose encapsulate comprising about 63% of an octocrylene, about 35% of avobenzone and about 2% trimethoxy benylidene pentanedione, about 8% of a cellulose encapsulate comprising octinoxate, about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (DERMACYL® AFQ) was tested. The results indicate that the disclosed sunscreen lotion composition had an average SPF value of 64.50 based on the static assay (Table 7). However, even after a 40 water immersion assay, the UV radiation protective capabilities of this composition was maintained, dropping only to an average SPF value of 30.0 (Table 7).

TABLE 7

Evaluation of Sunscreen Lotion Composition Comprising Photostabilizing Agent by SPF Determination (FDA) - Static and 40 Minute Water Immersion Assays

| Subject No. | Gender | MED[b]/Hr | I[a] (Amps) | Skin Type | MED I (J/m²) | MED II (J/m²) | STD[c] | WR Control | SPF Values Static | WR[d] |
|---|---|---|---|---|---|---|---|---|---|---|
| 74-5879 | M | 126.9 | 6.0 | III | 35.55 | 35.55 | 18.75 | 18.00 | 60.00 | <45.60 |
| 56-5529 | F | 128.5 | 6.5 | II | 28.44 | 28.44 | 18.75 | 15.00 | 69.00 | 30.00 |
| | | Mean (x) | | | | | 18.75 | 16.50 | 64.50 | 30.00 |
| | | Standard Deviation(s) | | | | | 0.00 | 2.12 | 6.36 | N/A |
| | | Standard Error | | | | | 0.00 | 1.50 | 4.50 | N/A |
| | | Standard Error % of Mean | | | | | 0 | 9.09 | 6.98 | N/A |
| | | N | | | | | 2 | 2 | 2 | 1 |

[a] I is Intensity of Light Source.
[b] MED is Minimal Erythemal Dose: 1 MED = 200 J/m²-eff.
[c] 7% PadO/3% Oxyb.
[d] Water Resistance based on water immersion assay.

Table 8 shows similar results. The disclosed sunscreen lotion composition exhibited an average SPF value of 69.0 based on the static assay (Table 8). However, even after an 80 water immersion assay, the UV radiation protective capabilities of this composition was maintained, dropping only to an average SPF value of 52.2 (Table 8). These results indicate that a photostabilizing agent significantly increases the UV radiation protective capabilities of a sunscreen composition, and that this enhanced protective effect appears to be maintained even exposure to water immersion.

TABLE 8

Evaluation of Sunscreen Lotion Composition Comprising Photostabilizing Agent by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 66 0787 | F | 127.4 | 6.0 | II | 28.44 | 28.44 | 16.30 | 15.00 | 69.00 | 52.20 |
| 56 2197 | F | 128.4 | 6.5 | II | 35.55 | 35.55 | 18.75 | 18.00 | 69.00 | 52.20 |
| Mean (x) | | | | | | | 17.53 | 16.50 | 69.00 | 52.20 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

Experiments were conducted with a sunscreen lotion composition comprising a film former. Table 9 shows the test results of a sunscreen lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a cellulose encapsulate comprising a silicone oil, a cellulose encapsulate comprising a comprising a shea oil, a film former, one or more emollients and one or more thickening agents. In particular, a sunscreen lotion composition comprising about 0.15% of a cellulose encapsulate comprising a silicone oil, about 0.2% of a cellulose encapsulate comprising a shea oil, about 11% of a cellulose encapsulate comprising about 65% of an octocrylene and about 35% of avobenzone, about 8% of a cellulose encapsulate comprising octinoxate, about 3% of an acrylate copolymer (DERMACRYL® AQF), about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (SIMLGEL® EG) was tested. The results indicate that the disclosed sunscreen lotion composition had an average SPF value of 57.5 based on the static assay (Table 9). However, even after a 40 water immersion assay, the UV radiation protective capabilities of this composition was maintained, dropping only to an average SPF value of 43.5 (Table 9).

TABLE 9

Evaluation of Sunscreen Lotion Composition Comprising Film Former by SPF Determination (FDA) - Static and 40 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 46 4829 | F | 127.3 | 6.4 | II | 35.55 | 35.55 | 18.75 | 18.00 | 57.50 | 43.50 |
| 74 0656 | F | 126.2 | 6.5 | I | 28.44 | 28.44 | 16.30 | 18.00 | 57.50 | 43.50 |
| Mean (x) | | | | | | | 17.53 | 18.00 | 57.50 | 43.50 |
| Standard Deviation(s) | | | | | | | 1.73 | 0.00 | 0.00 | 0.00 |
| Standard Error | | | | | | | 1.22 | 0.00 | 0.00 | 0.00 |
| Standard Error % of Mean | | | | | | | 6.96 | 0 | 0 | 0 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

Table 10 shows similar results. The disclosed sunscreen lotion composition exhibited an average SPF value of 53.75 based on the static assay (Table 10). However, even after an 80 water immersion assay, the UV radiation protective capabilities of this composition was maintained, dropping only to an average SPF value of 43.5 (Table 10). These results indicate that a film former significantly increases the UV radiation protective capabilities of a sunscreen composition, and that this enhanced protective effect appears to be maintained even exposure to water immersion.

TABLE 10

Evaluation of Sunscreen Lotion Composition Comprising Film Former by SPF Determination (FDA) - Static and 80 Minute Water Immersion Assays

| Subject No. | Gender | MED[b]/Hr | I[a] (Amps) | Skin Type | MED I (J/m²) | MED II (J/m²) | STD[c] | WR Control | SPF Values Static | WR[d] |
|---|---|---|---|---|---|---|---|---|---|---|
| 58 5653 | F | 128.3 | 6.0 | II | 28.44 | 28.44 | 18.75 | 18.00 | 57.50 | 43.50 |
| 68 4430 | F | 129.9 | 6.5 | I | 35.55 | 35.55 | 16.30 | 15.00 | 50.00 | 43.50 |
| Mean (x) | | | | | | | 17.53 | 16.50 | 53.75 | 43.50 |
| Standard Deviation(s) | | | | | | | 1.73 | 2.12 | 5.30 | 0.00 |
| Standard Error | | | | | | | 1.23 | 1.50 | 3.75 | 0.00 |
| Standard Error % of Mean | | | | | | | 7.02 | 9.09 | 6.98 | 0.00 |
| N | | | | | | | 2 | 2 | 2 | 2 |

[a]I is Intensity of Light Source.
[b]MED is Minimal Erythemal Dose: 1 MED = 200 J/m²-eff.
[c]7% PadO/3% Oxyb.
[d]Water Resistance based on water immersion assay.

Experiments were conducted with a sunscreen lotion composition comprising a photostabilizing agent and a film former. Table 11 shows the test results of a sunscreen lotion composition disclosed herein comprises a cellulose encapsulate comprising a broad spectrum UVA/UVB sunscreen active agent, a UVA sunscreen active agent and a photostabilizing agent, a cellulose encapsulate comprising a UVB sunscreen active agent, a cellulose encapsulate comprising a silicone oil, a cellulose encapsulate comprising a comprising a shea oil, a film former, one or more emollients and one or more thickening agents. In particular, a sunscreen lotion composition comprising about 0.15% of a cellulose encapsulate comprising a silicone oil, about 0.2% of a cellulose encapsulate comprising a shea oil, about 8% of a cellulose encapsulate comprising about 63% of an octocrylene, about 35% of avobenzone and about 2% trimethoxy benylidene pentanedione, about 6% of a cellulose encapsulate comprising octinoxate, about 3% of an acrylate copolymer (DERMACRYL® AQF), about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (SIMLGEL® EG) was tested. The results indicate that the disclosed sunscreen lotion composition had an average SPF value of 69.0 based on the static assay (Table 11). In addition, even after an 80 water immersion assay, the UV radiation protective capabilities of this composition was maintained, dropping only to an average SPF value of 52.2 (Table 11). These results indicate that while a photostabilizing agent significantly increases the UV radiation protective capabilities of a sunscreen composition, the addition of a film former appears to maintain this enhanced protective effect after exposure to water immersion.

TABLE 11

Evaluation of Sunscreen Lotion Composition Comprising Photostabilizing Agent and Film Former by SPF Determination (FDA) - Static and 80 Minute Water Immersion Assays

| Subject No. | Gender | MED[b]/Hr | I[a] (Amps) | Skin Type | MED I (J/m²) | MED II (J/m²) | STD[c] | WR Control | SPF Values Static | WR[d] |
|---|---|---|---|---|---|---|---|---|---|---|
| 66 0787 | F | 127.4 | 6.0 | II | 28.44 | 28.44 | 16.30 | 15.00 | 69.00 | 52.20 |
| 56 2197 | F | 128.4 | 6.5 | II | 35.55 | 35.55 | 18.75 | 18.00 | 69.00 | 52.20 |
| Mean (x) | | | | | | | 17.53 | 16.50 | 69.00 | 52.20 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a]I is Intensity of Light Source.
[b]MED is Minimal Erythemal Dose: 1 MED = 200 J/m²-eff.
[c]7% PadO/3% Oxyb.
[d]Water Resistance based on water immersion assay.

Example 3: SPF Testing of Sunscreen Soap Compositions

Sunscreen soap compositions disclosed herein were tested to determine their SPF value using the static and water immersion (40 minute) assays as described in Example 1, except that prior to application, the sunscreen soap composition was dissolve in water, such that it was diluted to a 50% concentration and the prepared solution was then delivered to the test site at a dosage of 4.0 mg/cm².

Table 12 shows the test results of a sunscreen soap composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquaternium mixed into a soap base. In particular, a sunscreen soap composition comprising about 8% of a cellulose encapsulate comprising about 65% of an octocrylene and about 35% of avobenzone, about 6% of a cellulose encapsulate comprising octinoxate and about 2% of polyquaternium 16 mixed into a soap base was tested. The results indicate that the disclosed sunscreen lotion composition had an average SPF value of 25.3 based on the static assay (Table 12). However, after a 40 water immersion assay, the UV radiation protective capabilities of this composition was not maintained (Table 12).

TABLE 12

Evaluation of Sunscreen Soap Composition by SPF Determination (FDA) - Static and 40 Minute Water Immersion Assays

| Subject No. | Gender | MED[b]/Hr | I[a] (Amps) | Skin Type | MED I (J/m²) | MED II (J/m²) | STD[c] | WR Control | SPF Values Static | WR[d] |
|---|---|---|---|---|---|---|---|---|---|---|
| 74 5198 | M | 129.3 | 6.4 | II | 28.44 | 28.44 | 18.75 | 18.00 | 25.30 | <16.72 |
| 52 3527 | F | 126.6 | 6.5 | II | 44.44 | 44.44 | 16.30 | 15.00 | 25.30 | 15.00 |
| Mean (x) | | | | | | | 17.53 | 16.50 | 25.30 | 15.00 |
| Standard Deviation(s) | | | | | | | 1.73 | 2.12 | 0.00 | N/A |
| Standard Error | | | | | | | 1.22 | 1.50 | 0.00 | N/A |
| Standard Error % of Mean | | | | | | | 6.96 | 9.09 | 0 | N/A |
| N | | | | | | | 2 | 2 | 2 | 1 |

[a]I is Intensity of Light Source.
[b]MED is Minimal Erythemal Dose: 1 MED = 200 J/m²-eff.
[c]7% PadO/3% Oxyb.
[d]Water Resistance based on water immersion assay.

Example 4: SPF Testing of Sunscreen after Shower Body Lotion Compositions

Sunscreen after shower body lotion compositions disclosed herein were tested to determine their SPF value using the static assay as described in Example 1.

Table 13 shows the test results of a sunscreen after shower body lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a cellulose encapsulate comprising a silicone oil, a cellulose encapsulate comprising shea oil, a polyquaternium, a film former and one or more surfactants. In particular, a sunscreen after shower body lotion composition comprising about 11% of a cellulose encapsulate comprising about 65% of an octocrylene and about 35% of avobenzone, about 8% of a cellulose encapsulate comprising octinoxate, about 0.15% of a cellulose encapsulate comprising a silicone oil, about 0.2% of a cellulose encapsulate comprising a shea oil, about 2.5% of polyquaternium 4 or polyquaternium 10, about 2.5% of an acrylate copolymer (DERMACRYL® AQF), about 2.0% acrylate-sodium acryloyldimethyl taurate copolymer-based thickening agent including isohexadecane and polysorbate 80 (SIMLGEL® EG) and about 1.5% cocamidopropyl betaine was tested. The results indicate that the disclosed sunscreen after shower body lotion composition had an average SPF value of 46 based on the static assay (Table 13).

Example 5: SPF Testing of Sunscreen Lotion Compositions

Sunscreen lotion compositions disclosed herein were tested to determine their SPF value using the static assay as described in Example 1.

Experiments were conducted with a sunscreen lotion composition comprising a polyquaternium and a film former. Table 14 shows the test results of a sunscreen lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquaternium and a film former. In particular, a sunscreen lotion composition comprising about 13.5% of a cellulose encapsulate comprising about 65% of an octocrylene and about 35% of avobenzone, about 13.5% of a cellulose encapsulate comprising octinoxate, about 0.7% of polyquaternium 4 and about 2% of an acrylate copolymer (DERMACRYL® AQF) was tested. The results indicate that the disclosed sunscreen lotion composition had an average SPF value of 37.05 based on the static assay (Table 14).

TABLE 13

Evaluation of Sunscreen After Shower Body Lotion Composition by SPF Determination (FDA) - Static Assay

| Subject No. | Gender | MED[b]/Hr | I[a] (Amps) | Skin Type | MED I (J/m²) | MED II (J/m²) | STD[c] | SPF Values |
|---|---|---|---|---|---|---|---|---|
| 54 2436 | F | 128.4 | 6.0 | II | 30.33 | 30.33 | 16.30 | 46 |
| 48 5699 | M | 125.7 | 6.0 | II | 30.33 | 30.33 | 16.30 | 46 |
| Mean (x) | | | | | | | 16.30 | 46 |
| Standard Deviation(s) | | | | | | | 0 | 0 |
| Standard Error | | | | | | | 0 | 0 |
| Standard Error % of Mean | | | | | | | 0 | 0 |
| N | | | | | | | 2 | 2 |

[a]I is Intensity of Light Source.
[b]MED is Minimal Erythemal Dose: 1 MED = 200 J/m²-eff.
[c]7% PadO/3% Oxyb.

TABLE 14

Evaluation of Sunscreen Lotion Composition by SPF Determination (FDA) - Static Assay

| Subject No. | Gender | MED[b]/Hr | I[a] (Amps) | Skin Type | MED I (J/m$^2$) | MED II (J/m$^2$) | STD[c] | SPF Values |
|---|---|---|---|---|---|---|---|---|
| 58 7412 | F | 127.4 | 6.0 | II | 46.20 | 46.20 | 16.30 | 34.50 |
| 70 6353 | F | 126.5 | 6.4 | II | 30.33 | 30.33 | 18.75 | 39.60 |
| Mean (x) | | | | | | | 17.53 | 37.05 |
| Standard Deviation(s) | | | | | | | 1.73 | 3.61 |
| Standard Error | | | | | | | 1.23 | 2.55 |
| Standard Error % of Mean | | | | | | | 7.02 | 6.88 |
| N | | | | | | | 2 | 2 |

[a] I is Intensity of Light Source.
[b] MED is Minimal Erythemal Dose: 1 MED = 200 J/m$^2$-eff.
[c] 7% PadO/3% Oxyb.

Experiments were conducted with a sunscreen lotion composition comprising a polyquaternium, a film former and an arachnid/insect repellent. Table 15 shows the test results of a sunscreen lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquaternium, a film former and an arachnid/insect repellent. In particular, a sunscreen lotion composition comprising about 13.5% of a cellulose encapsulate comprising about 65% of an octocrylene and about 35% of avobenzone, about 13.5% of a cellulose encapsulate comprising octinoxate, about 0.7% of polyquaternium 4, about 2% of an acrylate copolymer (DERMACRYL® AQF) and about 5% citronella was tested. The results indicate that the disclosed sunscreen lotion composition had an average SPF value of 37.05 based on the static assay (Table 15).

Experiments were conducted with a sunscreen lip balm composition comprising a polyquaternium and a film former. Table 16 shows the test results of a sunscreen lip balm composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquaternium and a film former. In particular, a sunscreen lip balm composition comprising about 15% of a cellulose encapsulate comprising about 51% homosalate, about 24% octyl salicylate, about 13% avobenzone, about 6% trimethoxybenzylidene pentanedione (SYNOXYL® HSS) and about 5% of a polymer, 25% petroleum and 12% cocoa butter was tested. The results indicate that the disclosed sunscreen lip balm composition had an average SPF value of 44.20 based on the static assay (Table 16). In addition, even after an 80 water immersion assay, the UV radiation protective capabilities of this composition was maintained, dropping only to an average SPF value of 43.60 (Table 16). These results show that the disclose sunscreen lip balm compositions demonstrate a significant increase in UV radiation protection and very good water resistant properties.

TABLE 15

Evaluation of Sunscreen Lotion Composition by SPF Determination (FDA) - Static Assay

| Subject No. | Gender | MED[b]/Hr | I[a] (Amps) | Skin Type | MED I (J/m$^2$) | MED II (J/m$^2$) | STD[c] | SPF Values |
|---|---|---|---|---|---|---|---|---|
| 58 7412 | F | 127.4 | 6.0 | II | 46.20 | 46.20 | 16.30 | 34.50 |
| 70 6353 | F | 126.5 | 6.4 | II | 30.33 | 30.33 | 18.75 | 39.60 |
| Mean (x) | | | | | | | 17.53 | 37.05 |
| Standard Deviation(s) | | | | | | | 1.73 | 3.61 |
| Standard Error | | | | | | | 1.23 | 2.55 |
| Standard Error % of Mean | | | | | | | 7.02 | 6.88 |
| N | | | | | | | 2 | 2 |

[a] I is Intensity of Light Source.
[b] MED is Minimal Erythemal Dose: 1 MED = 200 J/m$^2$-eff.
[c] 7% PadO/3% Oxyb.

Example 6: SPF Testing of Sunscreen Lip Balm Compositions

A sunscreen lip balm compositions disclosed herein were tested to determine their SPF value using the static and water immersion (80 minute) assays as described in Example 1.

TABLE 16

Evaluation of Sunscreen Lip Balm Composition by SPF Determination (FDA) -
Static and 80 Minute Water Immersion Assays

| Subject No. | Gender | MED[b]/Hr | I[a] (Amps) | Skin Type | MED I (J/m²) | MED II (J/m²) | STD[c] | WR Control | SPF Values Static | WR[d] |
|---|---|---|---|---|---|---|---|---|---|---|
| 74 2314 | M | 126.1 | 6.1 | III | 44.44 | 44.44 | 16.30 | 18.00 | 46.00 | 46.00 |
| 82 8976 | F | 127.1 | 6.1 | III | 55.55 | 55.55 | 16.30 | 15.00 | 46.00 | 46.00 |
| 86 0336 | F | 125.5 | 6.3 | I | 28.44 | 28.44 | 16.30 | 18.00 | 46.00 | 46.00 |
| 56 9343 | F | 127.7 | 6.1 | II | 44.44 | 44.44 | 16.30 | 15.00 | 46.00 | 40.00 |
| 54 5854 | M | 127.1 | 6.1 | II | 44.44 | 44.44 | 18.75 | 18.00 | 46.00 | 46.00 |
| 52 0005 | M | 127.6 | 6.0 | II | 28.44 | 28.44 | 16.30 | 15.00 | 40.00 | 40.00 |
| 62 0069 | M | 127.3 | 6.0 | II | 35.55 | 35.55 | 16.30 | 18.00 | 46.00 | 46.00 |
| 76 5957 | F | 126.4 | 6.2 | II | 35.55 | 35.55 | 18.75 | 15.00 | 40.00 | 40.00 |
| 54 4669 | F | 126.3 | 6.0 | III | 55.55 | 55.55 | 18.75 | 18.00 | 40.00 | 40.00 |
| 52 6776 | F | 128.3 | 6.3 | II | 44.44 | 44.44 | 16.30 | 15.00 | 46.00 | 46.00 |
| Mean (x) | | | | | | | 17.04 | 16.50 | 44.20 | 43.60 |
| Standard Deviation(s) | | | | | | | 1.18 | 1.58 | 2.90 | 3.10 |
| Standard Error | | | | | | | 0.37 | 0.50 | 0.92 | 0.98 |
| Standard Error % of Mean | | | | | | | 2.17 | 3.03 | 2.08 | 2.25 |
| N | | | | | | | 10 | 10 | 10 | 10 |

[a]I is Intensity of Light Source.
[b]MED is Minimal Erythemal Dose: 1 MED = 200 J/m²-eff.
[c]7% PadO/3% Oxyb.
[d]Water Resistance based on water immersion assay.

Alternatively, testing can be done on a sunscreen lip balm composition comprising about 15% of a cellulose encapsulate comprising about 51% homosalate, about 24% octyl salicylate, about 13% avobenzone, about 3% ethylhexyl methoxycrylene (SOLASTAY® 51) and about 3% of a bis-methoxycrylene/octyldodecyl adipic acid/methylpropanediol copolymer (SOLASTAY® P1), 25% petroleum and 12% cocoa butter. Similar SPF results are expected.

Alternatively, testing can be done on a sunscreen lip balm composition comprising about 15% of a cellulose encapsulate comprising about 51% homosalate, about 24% octyl salicylate, about 13% avobenzone, about 2% trimethoxybenzylidene pentanedione (SYNOXYL® HSS), about 2% ethylhexyl methoxycrylene (SOLASTAY® 51) and about 2% of a bis-methoxycrylene/octyldodecyl adipic acid/methylpropanediol copolymer (SOLASTAY® P1), 25% petroleum and 12% cocoa butter. Similar SPF results are expected.

Example 7: Skin Penetration Experiments

An experiment was conducted to demonstrate that sunscreen active agents contained within the presently claimed cellulose derived capsules prevent absorption of the sunscreen active agents into the skin. Two sunscreen compositions were prepared. Sunscreen Composition 1 (Sun Comp 1) was a commercially available sunscreen formulation that contained 4.5% octylmethoxy cinnamate (unencapsulated or free) and was spiked with 0.2% Nile Red fluorescent dye. Sunscreen Composition 2 (Sun Comp 2) contained flexible cellulose derived capsules containing 4.5% octylmethoxy cinnamate and 0.2% Nile Red fluorescent dye.

Previously frozen (−80° C.) deidentified human breast skin (n=5) from a common donor were prepared by cleaning the skin surface with 70% ethanol and air dried for 5 minutes to remove superficial fluids that might impact absorption. Each sunscreen composition was then applied to a separate region of the surface of the prepared samples by spreading the composition with a plastic pipet tip to form an even layer with a minimum 5 mm margin of untreated surface at the cut edges. Each skin sample received a total dose of 5 mg/cm² of each sunscreen composition. After dosing samples were incubated on a 35° C. flat surface with the inner sides of the samples kept hydrated with PBS buffer. Data was acquired for incubation times of 30 minutes and 90 minutes for each product type. After incubation, skin samples were blotted with absorbent paper to remove superficial sunscreen, then cleaned twice with fresh paper moistened with deionized water. Samples were mounted on a Vivascope 1500 fluorescence microscope fitted with a 658 nm, 531 nm, and 488 nm laser. Sample height and suitable topography were identified and imaged using 658 nm illumination in reflectance mode, and a co-registered fluorescence image stack was acquired at 10 μm depth steps using 488 nm illumination and a 607 nm filter set. Regions of Interest (ROI) of 100 by 100 pixels were identified in the 658 nm stack, confirmed in the 488 nm stack, and image intensity information was analyzed using ImageJ software (NIH) for each depth profile.

FIG. 1 indicates that dye penetration into skin is dramatically reduced (70%-80%) in the encapsulated formulation of Sunscreen Composition 2 relative to identically spiked commercial formulation of Sunscreen Composition 1, reflecting a strong reduction of octylmethoxy cinnamate absorption. In addition, no significant change in the overall concentration is observed between 30 and 90 minute time points, reflecting approximately steady-state flux, as the high surface concentration diffuses in to a relatively large volume of skin.

Figure 2:
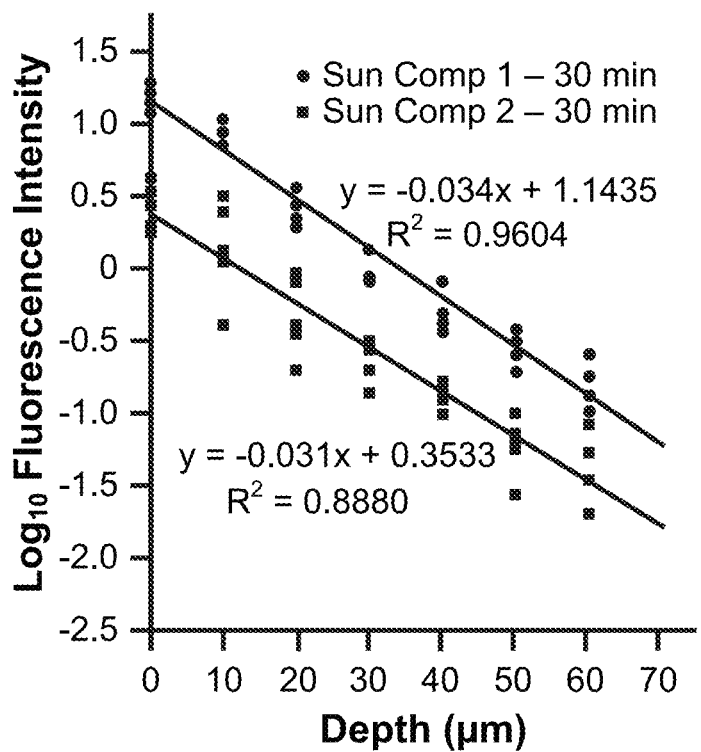
FIG. 2 shows a graph of dye penetration into human skin using $log_{10}$ fluorescence intensity of dye verus penetration depth of dye. Data from the 30 minutes after application of a composition were used.

Replotting the fluorescence data using the 30 minute time point on a log scale indicated that the intensity drops with depth in an approximately linear fashion (FIG. 2). This is consistent with the idea that the diffusion rate for the octylmethoxy cinnamate/Nile Red dye solution should be constant in the skin independent of the formulation. The intercept however, shows that the penetration of the octylmethoxy cinnamate/Nile Red dye solution at the skin surface is substantially reduced for the encapsulated formulation of Sunscreen Composition 2. This finding indicates that encapsulated octylmethoxy cinnamate of the encapsulated formulation of Sunscreen Composition 2 prevented the skin from becoming saturated with this sunscreen active agent.

FIGS. 3A-C visually shows that the vast majority of the fluorescent dye containing cellulose derived capsules remained on the skin surface (compare 10 μm skin depth photograph of FIG. 3A with 50 µm skin depth photograph of FIG. 3B and 90 µm skin depth photograph of FIG. 3C). For example, at 10 µm the stratum corneum is high reflective and appears bright. However, in deep locations, there is no bright appearance. Quantitation of the fluorescence indicate that very little penetration of the fluorescent dye occurred below 10 µm from the skin surface (FIG. 3D). In comparison to the commercial formulation of Sunscreen Composition 1, these results indicate that there is an 80% reduction in skin penetration of the florescent dye when using Sunscreen Composition 2.

Thus, in summary, these experimental results show that the encapsulated formulation of Sunscreen Composition 2 reduced the concentration of sunscreen at the skin surface by 80%, reduced the sunscreen active agent dose absorbed into the live layers of the epidermis by 80% and reduced sunscreen active agent availability to the skin surface so that SPF cannot diffuse into the skin.

Example 8: Product Comparison

Figure 4:
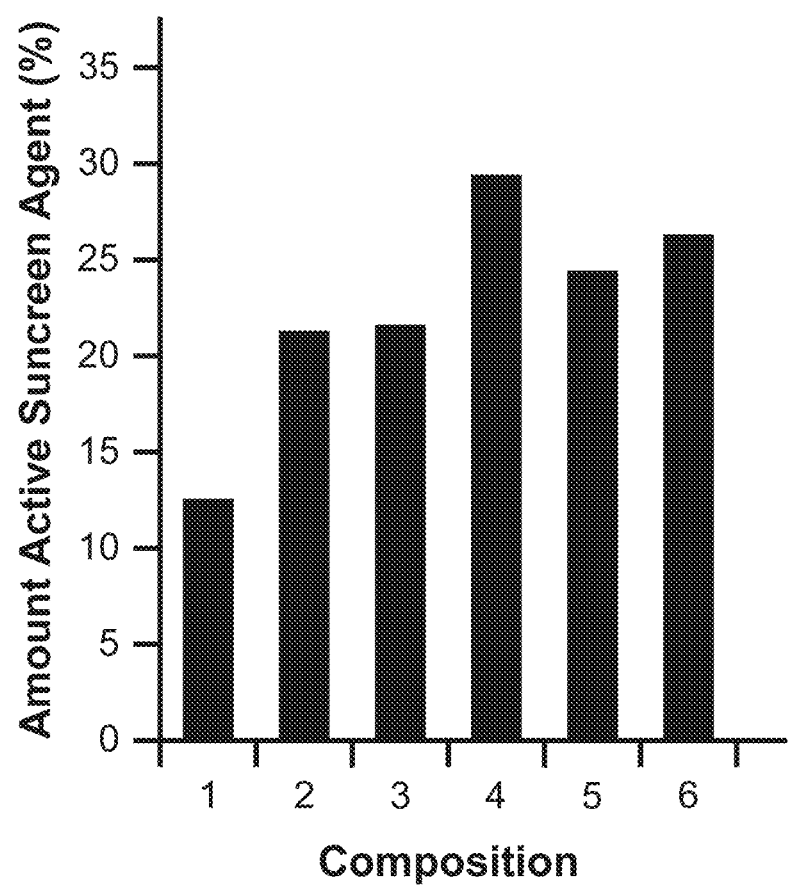
FIG. 4 shows a bar graph comparing the amount of sunscreen active agent needed to achieve an SPF value of 50.

An assessment was conducted to determine the amount of active sunscreen agent needed in a sunscreen compositions to achieve an average SPF value of 50. Six sunscreen compositions were assessed. Composition 1 was a sunscreen lotion composition disclosed herein comprising about 0.15% of a cellulose encapsulate comprising a silicone oil, about 0.2% of a cellulose encapsulate comprising a shea oil, about 11% of a cellulose encapsulate comprising about 65% of an octocrylene and about 35% of avobenzone, about 8% of a cellulose encapsulate comprising octinoxate, about 3% of an acrylate copolymer (DERMACRYL® AQF), about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (SIMLGEL® EG). Compositions 2-6 were commercially available sunscreen products having an SPF 50 value. Analysis of all six compositions revealed that to achieve an SPF 50, Composition 1 required about 13% by weight active sunscreen agents in an encapsulated form (FIG. 4). On the other hand, Compositions 2-6 required from about 22% to about 29% by weight active sunscreen agents to achieve a SPF value of 50 (FIG. 4). These results indicate that the sunscreen composition disclosed herein increases the efficacy of a UV absorber by at least 70%.

Example 9: Arachnid and Insect Repellancy Assay

Experiments were conducted to assess the mosquito repellency of compositions disclosed herein using two different assays.

To conduct a tick repellent assay, a 4 cm×8 cm basket with a 4 cm×4 cm opening in the bottom is suspended over a petri dish containing 10 *Rhipicephalus sanguineus* (Brown Dog Tick). A 4 cm×4 cm filer paper is attached to a 4 cm×8 cm paper and placed at the bottom of the basket so that the 4 cm×4 cm filer paper cover the 4 cm×4 cm opening located in the basket's bottom. A sample of blood is placed within the 4 cm×4 cm area of the filter paper. For the control composition, the filter paper is moistened with water and the number and of ticks attached to the bottom of the basket and the location distance from the 4 cm×4 cm filter paper was assessed during a 10 minute time period at 3 minutes, 5 minutes and 10 minutes. For the test compositions, the filter paper is treated by gently applying a roll-on applicator containing the test composition and the number and of ticks attached to the bottom of the basket and the location distance from the 4 cm×4 cm filter paper was assessed during a 10 minute time period at 3 minutes, 5 minutes and 10 minutes. Test composition 110216 is a lotion composition comprising about 14% of a cellulose encapsulate comprising about 94% Lemon Eucalyptus oil and about 6% of a polymer, 20% geraniol, 3% of a film former (DERMACRYL® E), about 1% fragrance and about 32% water. The data is shown in Table 17. The test composition shows a significant repellent activity compared to the control. Alternatively, tick repellency testing can be done using Test composition 100316 or Test composition 113016Z discussed below.

TABLE 17

| Tick Repellent Assay | | | | | |
|---|---|---|---|---|---|
| | | | Repellency | | |
| Composition | N | 3 min | 5 min | 10 min | Mean |
| Control | 7 | 63% | 42% | 47% | 51% |
| Test 110216 | 7 | 94% | 95% | 96% | 95% |

Assay for each compsition was repeated four times.

To conduct an AEDSAE 16 assay, a mosquito cage is set up with 25 female *Aedes aegypti* mosquitoes. The top lid of the cage has a 2.5" by 6" opening in the center. A collagen membrane is place over the opening and is used as the test surface because it mimics human skin. A test subject's forearm is then positioned over the opening. Mesh is placed on the top side of the test surface to prevent direct contact of the test surface with the test subject's arm and disposable wood spacers are placed on top of the top cover to elevate the test subject's arm from the test substance and to prevent the mosquitoes from being able to feed on the test subject. Pre-treatment landing and probing numbers were obtained by counting the number of mosquitos that landed and probed the collagen membrane during a 5 minute time period. Treatment landing and probing numbers were obtained as follows: for the control composition, the collagen membrance is moistened with water and landing and probing numbers were obtained by counting the number of mosquitos that landed and probed the treated collagen membrane during a 5 minute time period; for the test compositions, the collagen membrane is treated by gently applying a roll-on applicator containing the test composition and landing and probing numbers were obtained by counting the number of mosquitos that landed and probed the treated collagen membrane during a 5 minute time period. Test composition 100316 is a lotion composition comprising about 20% of a cellulose encapsulate comprising about 47% Lemon Eucalyptus oil, about 47% IR3535 and about 6% of a polymer, 3% of a film former (DERMACRYL® AQF), about 3% fragrance and about 40% water. Test composition 113016Z is a lotion composition comprising about 20% of a cellulose encapsulate comprising about 94% Lemon Eucalyptus oil and about 6% of a polymer, 3% of a film former (DERMACRYL® AQF), about 1% fragrance and about 44% water. Landing and probing numbers were collected at 1 hour, 2 hours and 4 hours after treatment of the collagen membrane. The percent landing and probing numbers were calculated by comparing the number of landing and probes during the pre-treatment evaluation to the number of landing and probes during the treatment evaluation at all three time intervals. The data is shown in Table 18. Both test compositions show a significant repellent activity compared to the control. Alternatively, mosquito repellency testing can be done using Test composition 110216 discussed above.

TABLE 18

Mosquito Repellent Assay

| Com-position | Post-Treatment Time (1 hr) | | Post-Treatment Time (2 hr) | | Post-Treatment Time (4 hr) | |
|---|---|---|---|---|---|---|
| | Landings | Probes | Landings | Probes | Landings | Probes |
| Control | −13% | −10% | −25% | −14% | −13% | −11% |
| Test 100316 | 100% | 100% | 99% | 100% | 91% | 99% |
| Test 113016Z | 100% | 100% | 94% | 99% | 96% | 100% |

Assay for each test composition was repeated four times.
Assay for the control composition was repeated twice.

Alternatively, arachnid/insect repellency testing can be done on a sunscreen/insect repellent composition comprising about 15% of a cellulose encapsulate comprising about 25.5% homosalate, about 12% octyl salicylate, about 6.5% avobenzone, about 1.5% ethylhexyl methoxycrylene (SOLASTAY® 51), about 1.5% of a bis-methoxycrylene/octyldodecyl adipic acid/methylpropanediol copolymer (SOLASTAY® P1), about 23.5% Lemon Eucalyptus oil, about 23.5% IR3535 and about 3% of a polymer, 3% of a film former (DERMACRYL® AQF) and about 3% fragrance. Similar SPF and repellency results are expected.

Alternatively, arachnid/insect repellency testing can be done on a sunscreen sunscreen/insect repellent composition comprising about 15% of a cellulose encapsulate comprising about 25.5% homosalate, about 12% octyl salicylate, about 6.5% avobenzone, about 1.5% trimethoxybenzylidene pentanedione (SYNOXYL® HSS), about 1.5% ethylhexyl methoxycrylene (SOLASTAY® 51), about 1.5% of a bis-methoxycrylene/octyldodecyl adipic acid/methylpropanediol copolymer (SOLASTAY® P1), about 47% Lemon Eucalyptus oil and about 4.5% of a polymer, 3% of a film former (DERMACRYL® AQF) and about 1% fragrance. Similar SPF and repellency results are expected.

Alternatively, arachnid/insect repellency testing can be done on a sunscreen sunscreen/insect repellent composition comprising about 15% of a cellulose encapsulate comprising about 25.5% homosalate, about 12% octyl salicylate, about 6.5% avobenzone, about 1.5% trimethoxybenzylidene pentanedione (SYNOXYL® HSS), about 1.5% ethylhexyl methoxycrylene (SOLASTAY® 51), about 1.5% of a bis-methoxycrylene/octyldodecyl adipic acid/methylpropanediol copolymer (SOLASTAY® P1), about 47% Lemon Eucalyptus oil and about 3% of a polymer, 20% geraniol, 3% of a film former (DERMACRYL® E) and about 1% fragrance. Similar SPF and repellency results are expected.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification.

It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A sunscreen composition comprising:
a first flexible cellulose derived capsule, the first flexible cellulose derived capsule comprising:
a) one or more UVA sunscreen active agents, each of the one or more UVA sunscreen active agents being in an amount of 3% or less of the total weight of the sunscreen composition,
b) one or more UVB sunscreen active agents, each of the one or more UVB sunscreen active agents being in an amount of 15% or less of the total weight of the sunscreen composition, and
c) one or more photostabilizing agents,
wherein the first flexible cellulose derived capsule comprises a flexible shell consisting essentially of cellulose, or a salt thereof; or a cellulose derivative, and
wherein the cellulose derivative is selected from the group consisting of: 1) ethyl cellulose, hydroxypropyl cellulose, hydroxypropylmethyl cellulose, hydroxyethyl ethyl cellulose, carboxymethyl cellulose, combinations thereof and salts thereof and 2) a derivative of hydroxypropylcellulose, hydroxypropylmethyl cellulose, ethyl cellulose, carboxymethyl cellulose, combinations thereof and salts thereof.

2. The sunscreen composition according to claim 1, wherein the one or more UVA sunscreen active agent includes a dibenzoylmethane.

3. The sunscreen composition according to claim 2, wherein the dibenzoylmethane includes Avobenzone.

4. The sunscreen composition according to claim 1, wherein the one or more UVB sunscreen active agents includes a salicylate.

5. The sunscreen composition according to claim 4, wherein the salicylate includes Homosalate and/or Octyl Salicylate.

6. The sunscreen composition according to claim 1, wherein the one or more photostabilizing agents is in an amount of about 0.1% to about 5.0% of the total weight of the sunscreen composition.

7. The sunscreen composition according to claim 1, wherein the one or more photostabilizing agents comprise a 4-methylbenzylidene camphor, a hindered amine light stabilizer, or a 2,2,6,6-tetramethyl piperidine-based compound.

8. The sunscreen composition according to claim 1, wherein the first flexible cellulose derived capsule further comprises a polyamide polymer.

9. The sunscreen composition according to claim 1, wherein the first flexible cellulose derived capsule is in an amount of about 10% to about 40% of the total weight of the composition.

10. The sunscreen composition according to claim 1, further comprising a second flexible cellulose derived capsule in an amount of about 0.01% to about 7% of the total weight of the composition, the second flexible cellulose derived capsule comprising a water-insoluble emollient comprising fatty acids,
  wherein the second flexible cellulose derived capsule comprises a flexible shell consisting essentially of cellulose, or a salt thereof; or a cellulose derivative, and
  wherein the cellulose derivative is selected from the group consisting of: 1) ethyl cellulose, hydroxypropyl cellulose, hydroxypropylmethyl cellulose, hydroxyethyl ethyl cellulose, carboxymethyl cellulose, combinations thereof and salts thereof and 2) a derivative of hydroxypropylcellulose, hydroxypropylmethyl cellulose, ethyl cellulose carboxymethyl cellulose, combinations thereof and salts thereof.

11. The sunscreen composition according to claim 1, further comprising a second flexible cellulose derived capsule in an amount of about 0.01% to about 7% of the total weight of the composition, the second flexible cellulose derived capsule comprising a silicone oil,
  wherein the second flexible cellulose derived capsule comprises a flexible shell consisting essentially of cellulose, or a salt thereof; or a cellulose derivative, and
  wherein the cellulose derivative is selected from the group consisting of: 1) ethyl cellulose, hydroxypropyl cellulose, hydroxypropylmethyl cellulose, hydroxyethyl ethyl cellulose, carboxymethyl cellulose, combinations thereof and salts thereof and 2) a derivative of hydroxypropylcellulose, hydroxypropylmethyl cellulose, ethyl cellulose, carboxymethyl cellulose, combinations thereof and salts thereof.

12. The sunscreen composition according to claim 1, further comprising:
  a) a flexible second cellulose derived capsule in an amount of about 0.01% to about 7% of the total weight of the composition, the second flexible cellulose derived capsule comprising a water-insoluble emollient comprising fatty acids,
  wherein the second flexible cellulose derived capsule comprises a flexible shell consisting essentially of cellulose, or a salt thereof; or a cellulose derivative, and
  wherein the cellulose derivative is selected from the group consisting of: 1) ethyl cellulose, hydroxypropyl cellulose, hydroxypropylmethyl cellulose, hydroxyethyl ethyl cellulose, carboxymethyl cellulose, combinations thereof and salts thereof and 2) a derivative of hydroxypropylcellulose, hydroxypropylmethyl cellulose, ethyl cellulose, carboxymethyl cellulose, combinations thereof and salts thereof; and
  b) a third flexible cellulose derived capsule in an amount of about 0.01% to about 7% of the total weight of the composition, the third flexible cellulose derived capsule comprising a silicone oil,
  wherein the third flexible cellulose derived capsule comprises a flexible shell consisting essentially of cellulose, or a salt thereof; or a cellulose derivative, and
  wherein the cellulose derivative is selected from the group consisting of: 1) ethyl cellulose, hydroxypropyl cellulose, hydroxypropylmethyl cellulose, hydroxyethyl ethyl cellulose, carboxymethyl cellulose, combinations thereof and salts thereof and 2) a derivative of hydroxypropylcellulose, hydroxypropylmethyl cellulose, ethyl cellulose, carboxymethyl cellulose, combinations thereof and salts thereof.

13. The sunscreen composition according to claim 1, further comprising a film former, the film former being in an amount of about 1% to about 6% of the total weight of the composition.

14. The sunscreen composition according to claim 13, wherein the film former includes a polyquaternium.

15. The sunscreen composition according to claim 1, further comprising one or more emollients, each of the one or more emollients being in an amount of about 0.25% to about 10% of the total weight of the composition.

16. The sunscreen composition according to claim 1, further comprising one or more antioxidant agents and/or one or more non-polar waxes.

17. The sunscreen composition according to claim 1, further comprising one or more thickening agents, each of the one or more thickening agents being in an amount of about 0.5% to about 12% of the total weight of the composition.

18. The sunscreen composition according to claim 1, wherein the sunscreen composition is a lotion, a lip balm, a bodywash, a shampoo, a conditioner, a soap, a gel, a hand sanitizer, a cream, a spray, a mousse, a make-up, or a hair spray.

19. The sunscreen composition according to claim 1, wherein the first flexible cellulose derived capsule has a mean diameter of about 200 nm to about 700 nm.

* * * * *